(12) United States Patent
Lunyak

(10) Patent No.: US 9,617,514 B2
(45) Date of Patent: Apr. 11, 2017

(54) DOWNREGULATION OF SINE/ALU RETROTRANSPOSON TRANSCRIPTION TO INDUCE OR RESTORE PROLIFERATIVE CAPACITY AND/OR PLURIPOTENCY TO A STEM CELL

(75) Inventor: Victoria V. Lunyak, Novato, CA (US)

(73) Assignee: BUCK INSTITUTE FOR RESEARCH ON AGING, Novato, CA (US)

(*) Notice: Subject to any disclaimer, the term of this patent is extended or adjusted under 35 U.S.C. 154(b) by 0 days.

(21) Appl. No.: 13/880,969

(22) PCT Filed: Oct. 20, 2011

(86) PCT No.: PCT/US2011/057140
§ 371 (c)(1),
(2), (4) Date: Sep. 6, 2013

(87) PCT Pub. No.: WO2012/058097
PCT Pub. Date: May 3, 2012

(65) Prior Publication Data
US 2013/0344603 A1     Dec. 26, 2013

Related U.S. Application Data

(60) Provisional application No. 61/455,808, filed on Oct. 26, 2010, provisional application No. 61/406,954, filed on Oct. 26, 2010.

(51) Int. Cl.
*C12N 5/00* (2006.01)
*C12N 15/11* (2006.01)
*C12N 5/074* (2010.01)
*C12N 5/0775* (2010.01)

(52) U.S. Cl.
CPC ......... *C12N 5/0607* (2013.01); *C12N 5/0667* (2013.01); *C12N 5/0696* (2013.01); *C12N 2310/531* (2013.01); *C12N 2501/65* (2013.01); *C12N 2510/00* (2013.01)

(58) Field of Classification Search
None
See application file for complete search history.

(56) References Cited

U.S. PATENT DOCUMENTS

2006/0177825 A1    8/2006    McDonald
2009/0099060 A1    4/2009    Bondarev et al.
2010/0221827 A1    9/2010    Jaenisch et al.

FOREIGN PATENT DOCUMENTS

WO    WO/2012/058097    5/2012

OTHER PUBLICATIONS

Bamazai et al., Stem Cells, 2012; 30:2603-2611.*
PCT International Search Report and Written Opinion dated Feb. 16, 2012 issued in PCT/US2011/057140.
PCT International Preliminary Report on Patentability dated Apr. 30, 2013 issued in PCT/US2011/057140.
Russian Office Action dated Nov. 19, 2015 issued in RU 2013119440 [with Translation].

* cited by examiner

*Primary Examiner* — Doug Schultz
(74) *Attorney, Agent, or Firm* — Tom Hunter; Weaver Austin Villeneuve & Sampson LLP

(57) ABSTRACT

In certain embodiments methods are provided for inducing and/or restoring and/or maintaining a non-senescent phenotype, or aspects thereof (e.g., proliferative capacity and/or pluripotency) in a mammalian cell. The methods typically involve reducing the level or activity of SINE/Alu retrotransposon transcripts in the cell in an amount sufficient to induce or restore proliferative capacity and/or pluripotency to said mammalian cell.

13 Claims, 42 Drawing Sheets

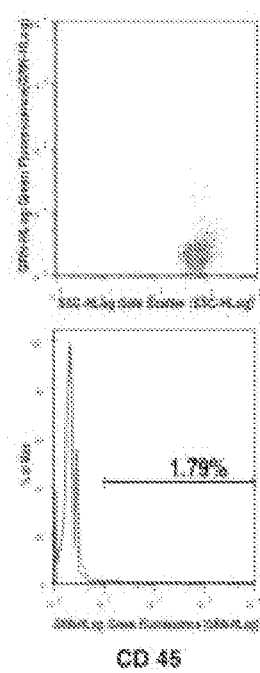
*Fig. 7A, cont'd.*
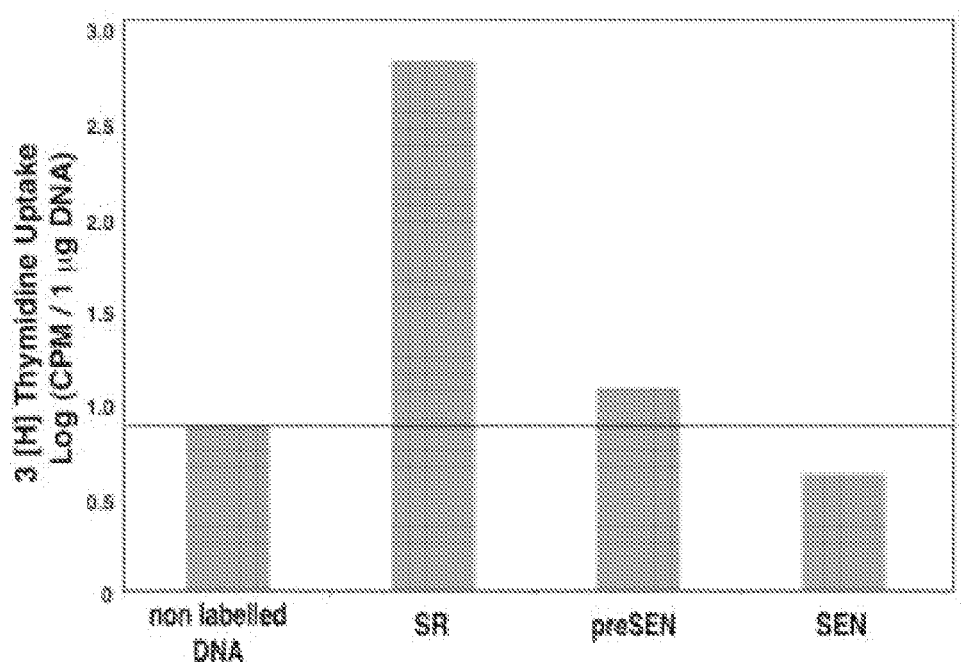
*Fig. 7B*

Methods for generation of iPSCs

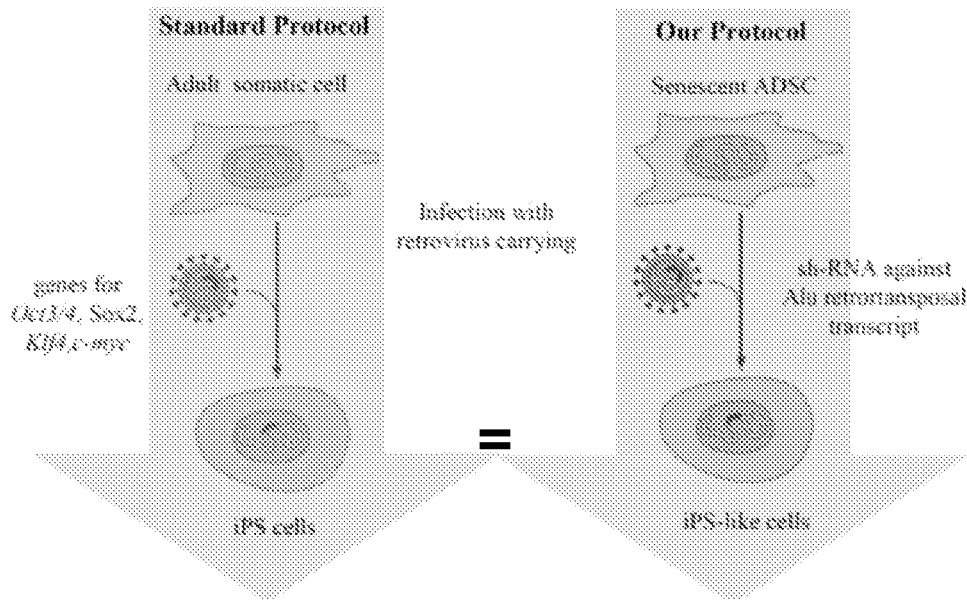

Conclusions

- We challenge the dogma that cellular senescence, and ultimately cellular aging is an irreversible process.
- We demonstrate the functional significance of SINE/Alu Retrotransposons in the mechanisms of ex vivo aging of human adult stem cells.
- We provide functional data demonstrating that the stable knockdown of generic SINE/Alu transcripts in senescent human adult stem cells reverses the aging phenotype, restores the capacity for self-renewal, and surprisingly increases stem cells pluripotency (iPS-like phenotye).

*Fig. 18*

293T cells culture 2 days after infection with sh-132 Alu

Formation of multilayer adherent networks (MAN)

Colony formation 7 days after single colony isolation and desegregation into individual cells (ES medium supplemented with LIF)

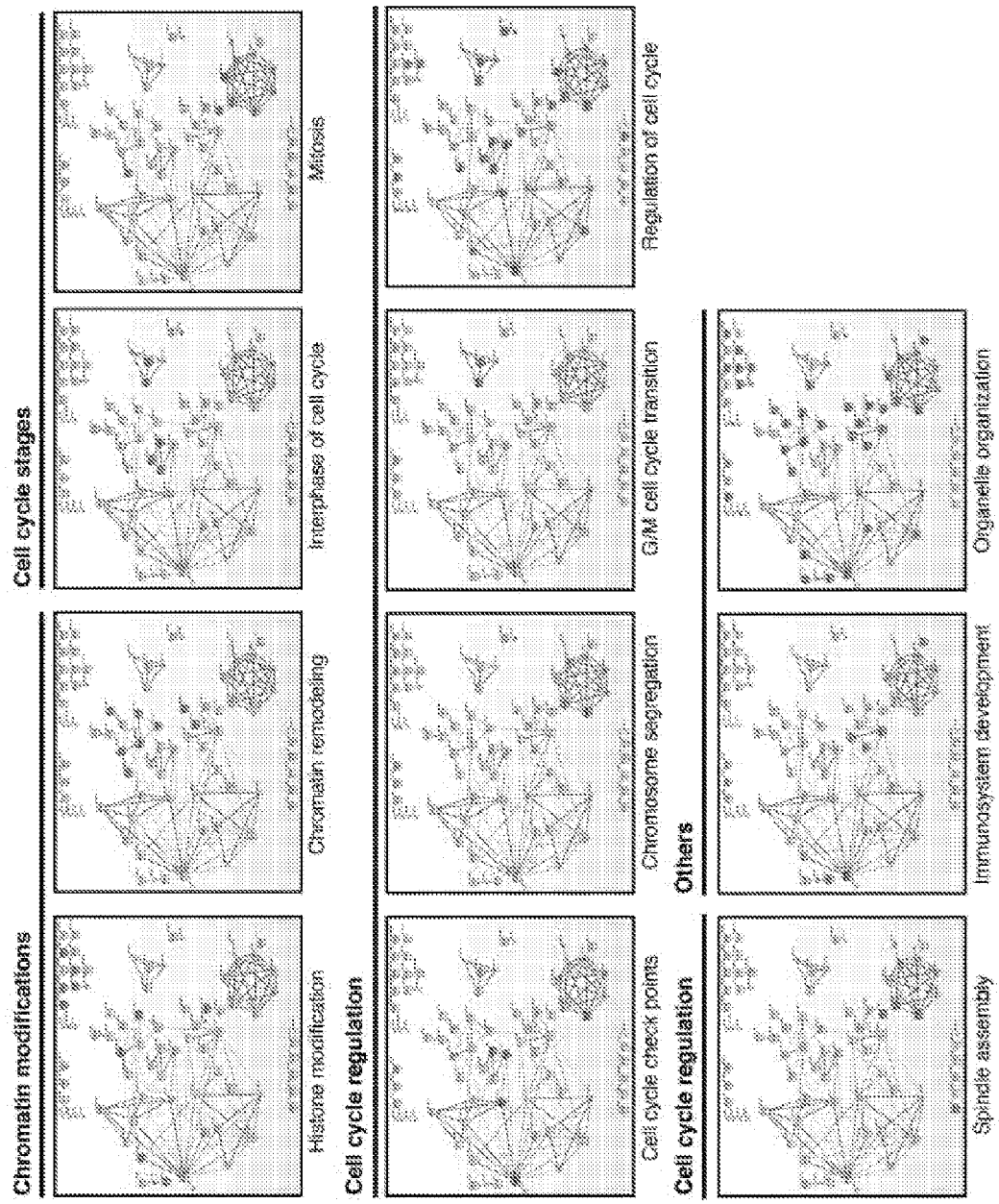
Fig. 25, cont'd.

DOWNREGULATION OF SINE/ALU RETROTRANSPOSON TRANSCRIPTION TO INDUCE OR RESTORE PROLIFERATIVE CAPACITY AND/OR PLURIPOTENCY TO A STEM CELL

CROSS-REFERENCE TO RELATED APPLICATIONS

This application is a 371 National Phase of PCT/US2011/057140, filed on Oct. 20, 2011, which claims priority to and benefit of U.S. Ser. No. 61/406,954, filed on Oct. 26, 2010 and to U.S. Ser. No. 61/455,808, filed on Oct. 26, 2010 both of which are incorporated herein by reference in their entirety for all purposes.

STATEMENT OF GOVERNMENTAL SUPPORT

This invention was made with government support under Grant No: DE019608 awarded by the by the National Institutes of Health. The government has certain rights in this invention.

BACKGROUND

Adult stem cells are extremely important for long-term tissue homeostasis throughout life. Their self-renewing proliferative capacity involves numerous tightly coordinated processes to ensure preservation of genome integrity during cell division. The regulatory mechanisms underlying their aging are less well defined. Nonetheless, global gene expression studies of stem cells purified from young and old mice have implicated the involvement of epigenetic regulation in higher-order chromatin dynamics. These studies have suggested coordinated age-dependent regulation of chromosomal regions, chromatin remodeling activities and lineage specification genes (Chambers et al. (2007) *PLoS Biol.*, 5: e201; Rossi et al. (2007) *Exp. Gerontol.*, 42: 385-390; Rossi et al. (2005) *Proc. Natl. Acad. Sci. USA*, 102: 9194-9199).

All cells are constantly challenged by exogenous and endogenous sources of DNA damage; depending on the nature of the damage, they activate different DNA damage repair mechanisms (Sinclair et al. (2004) *Am. Nat.*, 164: 396-414). In parallel, cells also activate checkpoint pathways, which delay cell cycle progression until genome integrity has been restored (Shiloh (2001) *Curr. Opin. Genet. Dev.*, 11: 71-77). One aspect of the stem cell hypothesis of aging postulates that the gradual and coordinated age-related loss of DNA damage repair capacity results in DNA damage accumulation over time. This damage would pose a significant threat to adult stem cell survival by altering proliferation and differentiation patterns, ultimately triggering cellular senescence. Therefore, the ability of adult stem cells to monitor and faithfully repair DNA damage is key to the prevention of aging and neoplastic transformations.

Little is known about the precise relationship between chromatin and DNA-repair factors. More than 50% of the human genome consists of retrotransposons (Lander et al. (2001) *Nature*, 409: 860-921). Their epigenetic makeup is poorly understood and inadequately annotated at the genomic level, due to a high degree of sequence conservation. In fact, many retrotransposons are derived from ancestral RNA genes and might represent genetically active sequences that encode different types of RNA with yet unknown functions (McClintock (1956) *Cold Spring Harb. Symp. Quant. Biol.*, 21: 197-216). However, clear evidence exists that the retrotransposal portion of the genome profoundly influences the organization, integrity, and evolution of the host's genome and transcriptome (Han et al. (2004) *Nature*, 429: 268-274; Kazazian (2004) *Science*, 303: 1626-1632). A growing body of evidence demonstrates that, during mammalian evolution, a large number of ancient retroelements acquired regulatory or structural functions.

The majority of retrotransposons are expressed in extraordinarily complex patterns in a cell- or tissue-specific manner, and potentially provide a rich source of non-protein coding RNAs to guide the trajectories of cellular differentiation and multicellular development (Amaral et al. (2008) *Science* 319: 1787-1789; Birney et al. (2007) *Nature*, 447: 799-816; Denoeud et al. (2007) *Genome Res.*, 17: 746-759; Dinger et al. (2008) *Genome Res.*, 18: 1433-1445; Dinger et al. (2008) *J. Mol. Endocrinol.*, 40: 151-159; Emanuelsson et al. (2007) *Genome Res.*, 17: 886-897; Faulkner et al. (2009) *Nat. Genet.*, 41: 563-571; Lowe et al. (2007) *Proc. Natl. Acad. Sci. USA*, 104: 8005-8010; Mattick et al., (2009) *Bioessays*, 31: 51-59; Mercer et al. (2008) *Proc. Natl. Acad. Sci. USA*, 105: 716-721; Mikkelsen et al., ed. (2007) *Genome-wide maps of chromatin state in pluripotent and lineage-committed cells*; Rozowsky et al. (2007) *Genome Res.*, 17: 732-745; Trinklein et al. (2007) *Genome Res.*, 17: 720-731). Recent studies have proven that retrotransposon transcriptional activities trigger and guide the processes of (i) assembly of centromeric chromatin, (ii) gene transcription, (iii) compartmentalization of chromatin and, (iv) nuclear organization of chromatin insulation during X-chromosome inactivation. Retrotransposons also serve a distinct function in non-random chromosomal translocations in tumors (Allen et al. (2004) *Nat. Struct. Mol. Biol.*, 11: 816-821; Chueh et al. (2005) *Hum. Mol. Genet.*, 14: 85-93; Lei and Corces (2006) *Cell*, 124: 886-888; Lei and Corces (2006) *Nat. Genet.*, 38: 936-941; Lin et al. (2009) *Cell*, 139: 1069-1083; Lunyak (2008) *Curr. Opin. Cell Biol.*, 20: 281-287; Lunyak et al. (2007) *Science*, 317: 248-251; Mattick et al. (2009) *Bioessays*, 31: 51-59; Navarro et al. (2009) *Epigenetics Chromatin* 2: 8).

There is also a considerable amount of tissue-specific, development-specific, and disease-related variability in DNA methylation and covalent modifications of chromatin within the retrotransposal portion of the genome (Kondo and Issa (2003) *J. Biol. Chem.* 278: 27658-27662; Estecio et al. (2007) *PLoS ONE* 2: e399). A genome-wide study by Martens (Martens et al. (2005) *EMBO J.*, 24: 800-812) demonstrates that LINEs, SINE/Alus, and other interspersed retrotransposons have variable degrees of H3K9, H3K27, and H4K20 histone methylation, raising the possibility that posttranscriptional modifications (PTM) of retrotransposal chromatin can influence diverse cellular processes.

SUMMARY

Efficient repair of DNA double-strand breaks and authentic genome maintenance at the chromatin level are fundamental to faithful human adult stem cell self-renewal. Stem cell aging can be linked to deficiencies in these two processes. In one example, we report that ~65% of naturally occurring repairable damage in self-renewing adult stem cells occurs in transposable elements. Upregulation of transcriptional activity from SINE/Alu retrotransposons interferes with the recruitment of condensin I and cohesin complexes in pericentric chromatin, resulting in the loss of efficient DNA repair and, in turn, senescence. Stable knockdown of generic SINE/Alu transcripts in senescent human adult stem cells reinstates the cells self-renewing properties and unexpectedly increases their plasticity as manifested by upregulation of Nanog and Oct4. Our results demonstrate the functional significance of SINE/Alu retrotransposons and provide mechanistic insight into their novel role in mediating crosstalk between chromatin, DNA repair and aging of human adult stem cells.

In certain embodiments, methods are provided for restoring a non-senescent phenotype, or aspects of a non-senescent phenotype to a senescent cell (e.g., a senescent adult stem cell). In certain embodiments, methods are provided for maintaining a non-senescent phenotype, or aspects of a non-senescent phenotype in a cell (e.g., a senescent adult stem cell). In certain embodiments methods are provided for inducing and/or restoring and/or maintaining a non-senescent phenotype, or aspects thereof (e.g., proliferative capacity and/or pluripotency) in a mammalian cell. The methods typically involve reducing the level or activity of SINE/Alu retrotransposon transcripts in the cell in an amount sufficient to induce or restore proliferative capacity and/or pluripotency to said mammalian cell.

In certain embodiments methods of transdifferentiating a mammalian cell from a first cell type or lineage into a second cell type or lineage are provided. The method typically involves transforming a differentiated cell into a pluripotent cell (or restoring pluripotency to a stem cell or a progenitor cell) by one of the methods described herein (e.g., by reducing the level or activity of SINE/Alu retrotransposon transcripts in the cell); culturing the cell under conditions that induce or permit differentiation of the cell; selecting cells that have differentiated into the second cell type or lineage; and culturing the cells of said second cell type or lineage. In certain embodiments the first cell type is a mesodermal cell type. In certain embodiments the first cell type is an ectodermal cell type. In certain embodiments the first cell type is an endodermal cell type. In certain embodiments the first cell type or lineage is a mesodermal cell type and the second cell type or lineage is a neuroectodermal cell type. In certain embodiments the first cell type is an ectodermal cell type and the second lineage is a mesodermal or an endodermal cell type. In certain embodiments, the first cell type is an endodermal cell type and the second lineage is an ectodermal or mesodermal cell type. In certain embodiments the first cell type is an adipocyte or a bone marrow cell. In certain embodiments the second cell type is a cell type selected from the group consisting of a blood cell, a fetal cell, an epithelial cell, an adipocyte, a smooth muscle cell, a nerve cell, a pancreatic beta cell, and a cardiomyocyte. In certain embodiments the culturing the cell under conditions that induce or permit differentiation of said cell comprises culturing said cells in a medium lacking or having a reduced quantity of leukemia inhibitory factor (LIF) and/or contacting (or culturing) the cell with one or more reagents (e.g., retinoic acid, PDGF, insulin, Arctigenin, ATRA (vitamin A), boswellic acid, bromelain and other proteolytic enzymes, CAPE, flavonoids (including apigenin, luteolin, quercetin, genistein, and daidzein), emodin, EPA and DHA, monoterpenes, resveratrol, 1,25-D3 (vitamin D3)) that induce differentiation.

DEFINITIONS

Micro-RNAs are single-stranded RNAs of typically 22-nucleotides that are processed from ~70-nucleotide hairpin RNA precursors by the Rnase III nuclease, Dicer. Similar to siRNAs, miRNAs can silence gene activity through destruction of homologous mRNA in plants or blocking its translation in plants and animals.

shRNA or short hairpin RNA is an RNA molecule that contains a sense strand, antisense strand, and a short loop sequence between the sense and antisense fragments. Due to the complementarity of the sense and antisense fragments in their sequence, such RNA molecules tend to form hairpin-shaped double-stranded RNA (dsRNA). shRNA is cloned into a vector, allowing for expression by a pol III type promoter. The expressed shRNA is then exported into the cytoplasm where it is processed by dicer into siRNA which then get incorporated into the siRNA induced silencing complex (RISC).

Small Interfering RNA (siRNA) are typically 21-23 nucleotide double-stranded RNA molecules. Once incorporated into the RNA-induced silencing complex (RISC) they facilitate the cleavage and degradation of its recognized mRNA.

Piwi-interacting RNA (piRNA) is class of small non-coding RNA molecules that is expressed in, or can be introduced into animal cells (see, e.g., Seto et al. (2007) *Molecular Cell*, 26(5): 603-609; Siomi et al. (2011) *Nat. Rev. Mol. Cell. Biol.*, 12:246-258). piRNAs form RNA-protein complexes through interactions with piwi proteins. These piRNA complexes have been linked to both epigenetic and post-transcriptional gene silencing of retrotransposons and other genetic elements.

By "pluripotency" and "pluripotent stem cells" it is meant that such cells have the ability to differentiate into all types of cells in an organism. Pluripotent cells are characterized by the expression of one or more pluripotency markers known by one of ordinary skill in the art. Such markers include, but are not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In certain embodiments pluripontent cells are capable of forming or contributing to ectoderm, mesoderm, or endoderm tissues in a living organism.

The terms "primary cells", "primary cell lines", and "primary cultures" are used interchangeably herein to refer to cells and cell cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage. Typically, the primary adipose cells of the present invention are maintained for fewer than 10 passages in vitro prior to use.

The terms "individual," "subject," "host," and "patient," are used interchangeably herein and refer to any mammalian subject for whom diagnosis, treatment, or therapy is desired, particularly humans.

By "adipose" is meant any fat tissue. The adipose tissue may be brown or white adipose tissue, derived from subcutaneous, omental/visceral, mammary, gonadal, or other adipose tissue site. In certain embodiments the adipose is subcutaneous white adipose tissue or visceral adipose tissue or a lipoaspirate sample. The adipose tissue may be from any organism having fat tissue. Preferably, the adipose tissue is mammalian, most preferably the adipose tissue is human. A convenient source of adipose tissue is from liposuction surgery, however, the source of adipose tissue need not be so limited.

BRIEF DESCRIPTION OF THE DRAWINGS

FIG. 1A: Representative cumulative long term growth curve. Three distinct states are shown:

SR—self-renewing (population doubling <17); preSEN—presenescent (population doubling 29-38); SEN—senescent (population doubling >39). FIG. 1B: Immunohistochemical detection of senescence-associated β-galactosidase (SA-β-Gal) activity and 5"-bromo-2"deoxyuridine (BrdU) incorporation. Examples of hADSCs' morphological changes (10× magnification) shown in inserts. Bar graphs correspond to percentage of SA-β-Gal positive cells (left) and BrdU positive cells (right) with progressive ex-vivo hADSC expansion, based on three independent experiments. Error bars are standard deviations from the mean. FIG. 1C: DNA damage response (DDR) in senescent hADSCs. Representative immunostaining for persistent γH2AX (green)/53BP1 (red) foci formation upon senescence of hADSCs. Quantification of γH2AX/53BP1 foci formation upon ex-vivo expansion of hADSCs is given in FIG. 8.

FIG. 2A: Schematic flow-chart for nucleosomal ChIP-seq analysis using SOLiD (ABI) platform. FIG. 2B: Relative chromosomal distributions of γH2AX tags in self-renewing and senescent cells illustrated for chromosomes 10 and 21. γH2AX tag enrichment levels, calculated as the log 2 ratio of position-specific tag counts normalized by the genomic background, are shown for self-renewing and senescent cells. Relative differences in γH2AX tag enrichment levels between cells, calculated as the absolute values of the differences in cell stage specific enrichment levels, are shown below the individual cell tracks. Below the difference tracks, the chromosomal locations of large clusters of γH2AX modified sites are shown for the self-renewing and senescent cell types. FIG. 2C: Differences in the relative γH2AX enrichment levels for self-renewing (SR) versus senescent (SEN) cells across various genomic features. The absolute values of the normalized differences in γH2AX tag counts between cell types are shown on the y-axis. Blue bars show genomic features that have higher fractions in SR cells, and red bars show genomic features that have higher fractions in SEN cells. FIG. 2D: Scatter plots showing the relationship between gene density and γH2AX tag density for human chromosomes in self-renewing (SR) and senescent cells (SEN). The slopes and intercepts of the linear trends are shown (y-value) along with Spearman's rank correlation coefficients (R-value) and statistical significance levels (P-value). FIG. 2E: Scatter plots showing the relationship between GC content and γH2AX tag density for human chromosomes in self-renewing (SR) and senescent cells (SEN). The slopes and intercepts of the linear trends are shown (y-value) along with Spearman's rank correlation coefficients (R-value) and statistical significance levels (P-value). FIG. 2F: The enrichment levels of γH2AX in promoter regions, surrounding transcriptional start sites (TSS), are shown for self-renewing (blue) and senescent (red) cells. Enrichment levels are calculated as the log 2 ratio of the position-specific tag counts normalized to the genomic background. FIG. 2G: The numbers of genes with γH2AX modified sites in promoter regions, defined as ±2 Kb from transcription start sites, are shown for self-renewing (SR) and senescent (SEN) cells. The number of genes with γH2AX modified promoters found in both cell phenotypes is indicated in the intersection.

FIG. 3A: γH2AX enrichment levels in peritelomeric regions for self-renewing (SR—blue) and senescent (SEN—red) cell lines. Chromosome ends (telomeres) are shown at the origin of the x-axis, which then extends into the chromosome arms. Average γH2AX enrichment levels are calculated as the log 2 ratio of the position-specific tag counts normalized to the genomic background averaged over all chromosome arms. FIG. 3B: γH2AX enrichment levels in pericentric regions for self-renewing (SR—blue) and senescent (SEN—red) cell lines. Centromeres are shown as gap centered on the x-axis, which extends into the chromosome arms in either direction. Average γH2AX enrichment levels are calculated as the log 2 ratio of the position-specific tag counts normalized to the genomic background averaged over all chromosomes. FIG. 3C: Statistical significance of γH2AX accumulation for the peri-telomeric regions of human chromosomes, left and right arms, in self-renewing (SR—blue) and senescent (SEN—red) cells. Significance levels (P-values) are calculated by comparing peritelomeric γH2AX levels to the genomic background and are plotted as −ln P, where −ln P=3 (horizontal line) corresponds roughly to the 95% confidence interval. FIG. 3D: Statistical significance of γH2AX accumulation for the pericentric regions of human chromosomes in self-renewing (SR—blue) and senescent (SEN—red) cells. Significance levels (P-values) are calculated by comparing pericentric γH2AX levels to the genomic background and are plotted as −ln P, where −ln P=3 (green line) corresponds roughly to the 95% confidence interval. FIG. 3E: Differences in the numbers of large γH2AX clusters in pericentric regions between senescent versus self-renewing cells. The absolute values of the normalized differences for γH2AX clusters between cell phenotypes are shown on the y-axis. Blue bars show chromosomes that have more large clusters in SR cells, and red bars show chromosomes that have more large clusters in SEN cells.

FIG. 6A: Model of SINE/Alu retrotransposon. Secondary structure of generic SINE/Alu RNA (SEQ ID NO:1). Regions for shRNA design are shaded. FIG. 6B: Representative example of the efficiency of lentiviral transduction of hADSCs depicted by GFP. FIG. 6C: Northern blot hybridization of the RNA recovered from hADSCs cells stably expressing sh-RNA against SINE/Alu. Senescent hADSCs were infected with lentiGFP sh-193Alu, lentiGFP sh-132Alu or control no shRNA insert lentiGFP. RNA was isolated after 24 hrs post transduction and Northern hybridization was performed with a SINE/Alu specific oligonucleotide. Senescent hADSCs stably expressing sh-132Alu show near complete knockdown of the SINE/Alu transcripts. FIG. 6D: Proliferative properties of senescent hADSCs were reinstated in the cells upon stable knockdown of SINE/Alu transcripts. $^3[H]$ thymidine uptake is shown. Senescent cells (wt) or senescent cells transduced with lentiGFP (control) or lentiGFP sh-132Alu were pulse-labeled with 1 $\mu$Ci of $^3[H]$ thymidine for 24 hrs either 24 or 96 hrs post infection. Data shown are mean±SEM for triplicate measurements. FIG. 6E: Expression of pluripotency markers Nanog and Oct4 was measured by qPCR analysis in senescent hADSCs (wt) and in hADSC with reversed-senescent phenotype upon stable knockdown of SINE/Alu transcription (lentiGFP sh-132Alu). RNA was isolated from the cells 96 hrs post infection. Results are expressed as relative quantity (DCt). Samples were normalized against $\beta$-actin. Data are shown as mean±SEM. (n=3) ***p=6.98e05, *p=0.03. FIG. 6F: Morphological changes in the reversed-senescence hADSCs with stable knockdown of SINE/Alu transcripts. After 7 days in culture without feed cells form GFP-positive cell aggregates stained positive for the pluripotency marker alkaline phosphatase (AP). FIG. 6G: Model of SINE/Alu transcriptional interference in triggering persistent DDR causing senescence of human adult mesenchymal stem cells.

FIGS. 7A-7B show FACS analysis and proliferative properties of hADSCs. FIG. 7A: FACS analysis of hADSCs. Early PD hADSCs were stained with FITC (CD 31, CD44 and CD 45) or AlexaFlour-488 (CD105) conjugated antibodies against cell surface markers and subjected to flow cytometric analysis. The cells were positive for CD 105 and CD 45, and negative for CD 34 and CD 44. The cell populations are shown as fluorescence to side scatter graphs (top), and the histograms (bottom) of stained cells (blue line) compared to un-stained cells (red line); with percentage of positive cells indicated. FIG. 7B: Replication capacity of hADSCs declines with ex-vivo aging. Proliferation in self-renewing (SR), pre-senescent (preSEN) and senescent cells (SEN) hADSCs was measured by $^3[H]$-thymidine uptake: 1 $\mu$Ci was added to 10,000 cells in 2 ml DMEM/F12 medium. After a 24-hr incubation, the cells were harvested, DNA was isolated, and radioactivity was measured by liquid scintillation counting. Results are presented as the amount of $^3[H]$-thymidine (cpm) incorporated during DNA synthesis per 1 $\mu$g of isolated DNA. DNA from cells not exposed to $^3[H]$-thymidine was used as background radiation control.

FIG. 11A: Frequency distributions for $\gamma$H2AX modified genomic positions in self-renewing (SR) and senescent (SEN) hADSCs. Mono-nucleosomal sized positions dominate the distributions. Accordingly, the frequencies of mid-size and large $\gamma$H2AX modified nucleosome clusters are enlarged and shown as insets for clarity. FIG. 11B: Percentages of genomic features occupied by $\gamma$H2AX modified mono-nucleosomes and large clusters of $\gamma$H2AX modified nucleosomes. FIG. 11C: Relative entropy was calculated as a measure of the difference between the SR versus SEN $\gamma$H2AX cluster size frequency distributions (see panel FIG. 11A). The relationship between relative entropy and cluster lengths was used to calculate a threshold (7,400 nt) between mid-size and large clusters as described in Supplemental Methods.

FIG. 15A schematically illustrates a protocol for stably knocking-down Alu transcripts using an shRNA delivered by a lentiviral vector. FIG. 15B illustrates the delivery vector, transfected cells and a Northern blot showing the results of transfection.

FIG. 18 shows a comparison between "standard" protocols for the generation of induced pluripotent stem cells (iPSCs) and one of the protocols described herein.

FIG. 19A illustrates the differentiation of ADSCs into neuroblasts. FIG. 19B illustrates the use of the methods described herein to transdifferentate cells into numerous other pathways/lineages.

FIG. 20A illustrates HEK 293T cells two days after infection with sh-132Alu. FIG. 20B illustrates colony formation 7 days after single colony isolation and desegregation into individual cells (ES medium supplemented with LIF). FIG. 20C shows the expression of pluripotency markers (nanog, oct4, and alkaline phosphatase). FIG. 20D shows the expression of mesodermal markers two days after the formation of embryoid bodies (EB). FIG. 20E shows the expression of osterogenic (osteopontin), adipogenic (lipoprotein lipase), and glial (GAFP) genes 2 days after formation Embryoid bodies (EB).

FIG. 22A (bottom) shows secondary structure of generic full-length Alu RNAv (SEQ ID NO:2). The horizontal highlighted segment represents the highly conserved 7SL-derived portion, while the vertical highlighted segment represents region used for synthetic RNA affinity assay.

DETAILED DESCRIPTION

Figure 1A:
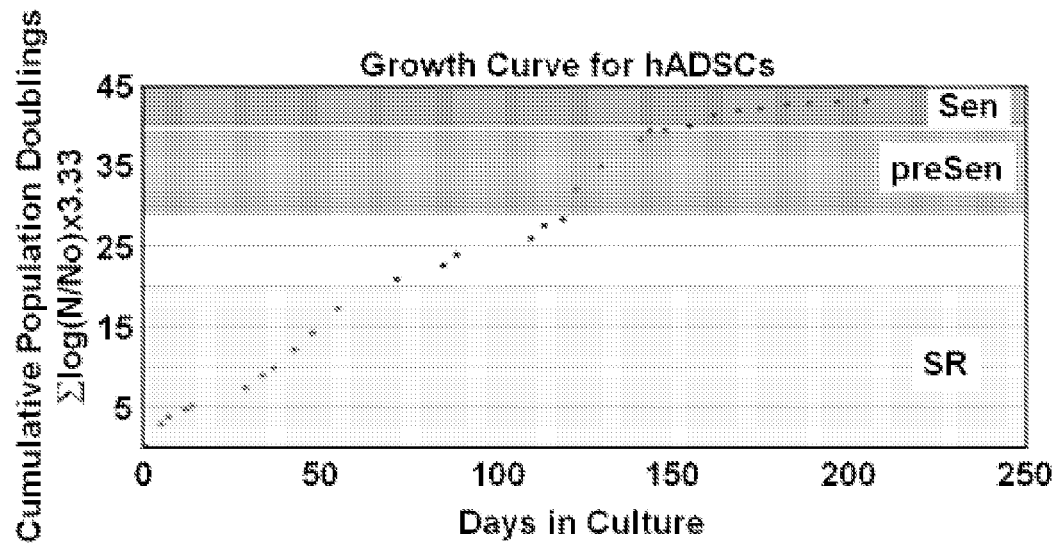
FIGS. 1A-1C illustrate features of the ex-vivo aging properties of hADSCs.

It was discovered that a significant (e.g., ~65% in certain instances) of naturally occurring repairable damage in self-renewing adult stem cells occurs in transposable elements. Upregulation of transcriptional activity from SINE/Alu retrotransposons interferes with the recruitment of condensin I and cohesin complexes in pericentric chromatin, resulting in the loss of efficient DNA repair and, in turn, senescence.

It was demonstrated that stable knockdown of generic SINE/Alu retrotransposon transcripts in senescent human adult stem cells reinstates the cells' self-renewing properties and unexpectedly increases their plasticity (e.g., as manifested by upregulation of the pluripotency markers Nanog and Oct4). The results presented herein demonstrate the functional significance of SINE/Alu retrotransposons and provide mechanistic insight into their novel role in mediating crosstalk between chromatin, DNA repair and aging of human adult stem cells.

In view of this discovery, methods are provided for inducing and/or restoring and/or maintaining proliferative capacity and/or pluripotency in a mammalian cell. More generally, the methods reduce the rate of onset of senescence or prevent senescence, or rescuing a cell from senescence. In various embodiments the methods induce or restore a pluripotent phenotype to a differentiated and/or senescent cell. In various embodiments the methods typically involve downregulating or inhibiting the level or activity of SINE/Alu retrotransposon transcripts in the cell (see, e.g., FIG. 18).

As demonstrated herein, such down regulation/inhibition rescues cells (e.g., adult stem cells) from senescence restoring pluripotency and/or proliferative capacity (see, e.g., FIGS. 6D, 6E 6F, 15, 16, and 17). Such down regulation affords a number of uses. For example, it is believed the viable lifetime of stem cell populations (e.g., stem cell lines) can be extended (perhaps indefinitely) by down regulating (e.g., stably down-regulating) SINE/Alu retrotransposon transcripts in those cells. When/if desired, the stem cells can be induced to differentiate into embryoid bodies, precursors or particular lineages, or terminally differentiated cells according to standard methods well known to those of skill in the art.

Accordingly cells (including previously terminally differentiated mammalian cells, progenitor cells, stem cells, stem cell lines, and induced pluripotent stem cells (iPSCs)) are provided where the cells have SINE/Alu retrotransposon transcripts downregulated. In various embodiments the cells include normal (non-senescent) stem cells, stem cells that have been "rescued" from senescence by downregulating SINE/Alu retrotransposon transcript production or activity, induced pluripotent stem cells (IPSCs) that contain a construct that downregulates SINE/Alu retrotransposon transcript level or activity, embryonic stem cells, and the like. In certain embodiments cells are excluded that have been treated in a manner to form IPSCs (e.g., cells are excluded in which one or more of Nanog, and/or LIN-28, and/or Oct3/4, and/or Sox2, and/or Klf4, and/or c-myc are directly upregulated and/or that contain heterologous constructs that express Oct3/4, and/or Sox2, and/or Klf4, and/or c-myc).

It was also demonstrated that cells in which pluripotency has been induced and/or restored according to the methods described herein (e.g., inhibition of Alu retrotransposon) can be subsequently induced to differentiate using standard methods well known to those of skill in the art (e.g., withdrawal of LIF from culture media) (see, e.g., FIGS. 19A, 19B, and FIGS. 20A-20E). This provides further evidence that the methods described herein induce or restore pluripotency to a cell. Accordingly, in certain embodiments, differentiated cells comprising cells that have been induced to differentiate from pluripotent cells generated according to the methods described herein are contemplated.

In addition, in certain embodiments, methods of transdifferentiating cells are contemplated. The transdifferentiation methods typically comprise inducing or restoring a cell to a pluripotent phenotype according to the methods described herein (e.g., by inhibiting the Alu retrotransposon or other components of the pathway), and then culturing the resulting pluripotent cells under conditions that allow or induce differentiation. Cells that differentiate into a desired cell type (e.g., pancreatic beta cells, motoneurons, hematopoietic progenitor cells, neural cells, dopaminergic neurons, adipocytes, cardiomyocytes, and the like) and/or lineage are then selected and can be subsequently cultured (e.g., expanded in culture) or directly utilized.

In certain embodiments the methods described herein can be used to restore pluripotency and/or proliferative capacity to a cell (e.g., to a cell that has committed to a differentiation pathway). In certain embodiments the methods described herein can be used to restore to a lesser senescent state or to a non-senescent state a cell that shows one or more indications of senescence.

In various embodiments stem cell comprises a cell selected from the group consisting of an embryonic stem cell, a cord blood stem cell, an adult stem cell, and an IPSC.

In various embodiments the mammalian stem cell is a stem cell derived from a tissue selected from the group consisting of human adipose tissue, human bone marrow, human neurological tissue, human smooth muscle, human adipose tissue, human cardiomyocytes, human endothelial tissue, human epithelial tissue, human pancreatic tissue, human bone or cartilage and the like.

In certain embodiments the cell is one that has committed to differentiation to a cell type selected from the group consisting of ectoderm, mesoderm, and endoderm. In certain embodiments the cell is one that has committed to differentiation to a cell type selected from the group consisting of human adipose cells, human blood cells, human nerve cells, human smooth muscle cells, human adipocytes, human chondrocytes, human osteoclasts and hosteoblasts, human cardiomyocytes, human endothelial cells, and human epithelial cells. In certain embodiments the cell comprises a non-renewing progenitor cell. In certain embodiments the mammalian cell comprises a terminally differentiated cell.

Downregulating/Inhibiting SINE/Alu Retrotransposon Transcripts

It was a surprising discovery that inhibition of SINE/Alu retrotransposon transcripts can restore proliferative capacity and/or pluripotency to a senescent stem cell or can maintain proliferative capacity and/or pluripotency in a non-senescent stem cell. Any of a variety of methods to inhibit SINE/Alu retrotransposon transcripts can be used.

In various embodiments SINE/Alu retrotransposon transcripts can be reduced/inhibited using inhibitory RNAs. Suitable inhibitory RNAs include, but are not limited to siRNAs, shRNAs, miRNAs, dicer-substrate 27-mer duplexes, single-stranded interfering RNA, and the like.

siRNAs typically refer to a double-stranded interfering RNA unless otherwise noted. In various embodiments, suitable siRNA molecules to inhibit SINE/Alu retrotransposon transcripts include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can to inhibit SINE/Alu retrotransposon transcripts. Examples of other interfering RNA molecules that can to inhibit SINE/Alu retrotransposon transcripts include, but are not limited to short hairpin RNAs (shRNAs), single-stranded siRNAs, microRNAs (miRNAs), and dicer-substrate 27-mer duplexes. Examples of RNA-like molecules that can to inhibit SINE/Alu retrotransposon transcripts include, but are not limited to siRNA, single-stranded siRNA, microRNA, piwiRNA, and shRNA molecules containing one or more chemically modified nucleotides, one or more non-nucleotides, one or more deoxyribonucleotides, and/or one or more non-phosphodiester linkages. Typically, all RNA or RNA-like molecules that can interact with SINE/Alu retrotransposon transcripts RISC and participate in RISC-related changes in gene expression can be referred to as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

Using the known nucleotide sequences for SINE/Alu retrotransposon transcript(s), suitable siRNAs can readily be produced. In various embodiments siRNA that inhibit SINE/Alu retrotransposon transcripts can comprise partially purified RNA, substantially pure RNA, synthetic RNA, recombinantly produced RNA, as well as altered RNA that differs from naturally-occurring RNA by the addition, deletion, substitution and/or alteration of one or more nucleotides. Such alterations can include, for example, addition of non-nucleotide material, such as to the end(s) of the siRNA or to one or more internal nucleotides of the siRNA, including modifications that make the siRNA resistant to nuclease digestion.

In various embodiments one or both strands of the siRNA can comprise a 3' overhang. As used herein, a "3' overhang" refers to at least one unpaired nucleotide extending from the 3'-end of an RNA strand. Thus in one embodiment, the siRNA comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length.

In an illustrative embodiment in which both strands of the siRNA molecule comprise a 3' overhang, the length of the overhangs can be the same or different for each strand. In certain embodiments the 3' overhang is present on both strands of the siRNA, and is one, two, or three nucleotides in length. For example, each strand of the siRNA can comprise 3' overhangs of dithymidylic acid ("TT") or diuridylic acid ("uu").

In order to enhance the stability of the siRNA, the 3' overhangs can be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNAi degradation. In particular, it is believed the absence of a 2' hydroxyl in the 2'-deoxythymidine can significantly enhance the nuclease resistance of the 3' overhang.

In certain embodiments, the siRNA comprises the sequence AA(N19)TT (SEQ ID NO:3), AA(N21)TT (SEQ ID NO:4), NA(N21) (SEQ ID NO:5), and the like, where N is any nucleotide. In various embodiments these siRNA comprise approximately 30%-70% GC, and preferably comprise approximately 50% G/C. The sequence of the sense siRNA strand corresponds to (N19)TT (SEQ ID NO:6) or N21 (SEQ ID NO:7) (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another illustrative embodiment, the siRNA comprises the sequence NAR(N17)YNN (SEQ ID NO:8), where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In various embodiments the siRNA of the invention can be targeted to any stretch of approximately 10-30, or 15-25, or 19-25 contiguous nucleotides in any of the target mRNA sequences (the "target sequence"). Techniques for selecting target sequences for siRNA are given, for example, in Tuschl et al., "The siRNA User Guide," revised May 6, 2004. The "siRNA User Guide" is available on the world wide web at a website maintained by Dr. Thomas Tuschl, and can be found by accessing the website of Rockefeller University and searching with the keyword "siRNA." In addition, the "siRNA User Guide" can be located by performing a google search for "siRNA User Guide" and can also be found at "www.rockefeller.edu/labheads/tusch1/sirna.html. Techniques for selecting target sequences for siRNA and miRNA can also be found in Sioud (2008) *siRNA and miRNA Gene Silencing: From Bench to Bedside* (*Methods in Molecular Biology*), Humana Press.

In certain embodiments the sense strand of the present siRNA comprises a nucleotide sequence identical to any contiguous stretch of about 19 to about 25 nucleotides in the target SINE/Alu retrotransposon transcript(s).

The SINE/Alu retrotransposon transcript silencing siRNAs can be obtained using a number of techniques known to those of skill in the art. For example, the siRNA can be chemically synthesized or recombinantly produced using methods known in the art, such as the *Drosophila* in vitro system described in U.S. published application US 2002/0086356.

In certain embodiments the siRNAs are chemically synthesized using appropriately protected ribonucleoside phosphoramidites and a conventional DNA/RNA synthesizer. The siRNAs can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Custom siRNA can be obtained from commercial suppliers (see, e.g., Thermo Fisher Scientific, Lafayette Colo.; Qiagen, Valencia, Calif.; Applied Biosystems, Foster City, Calif.; and the like).

In certain embodiments siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the target area(s) in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions. Selection of plasmids suitable for expressing siRNAs, methods for inserting nucleic acid sequences for expressing the siRNA into the plasmid, and methods of delivering the recombinant plasmid to the cells of interest are within the skill in the art (see, e.g., Tuschl (2002) *Nat. Biotechnol.*, 20: 446-448; Brummelkamp et al. (2002) *Science* 296: 550 553; Miyagishi et al. (2002) *Nat. Biotechnol.* 20: 497-500; Paddison et al. (2002) *Genes Dev.* 16: 948-958; Lee et al. (2002) *Nat. Biotechnol.* 20: 500-505; Paul et al. (2002) *Nat. Biotechnol.* 20: 505-508, and the like).

In one illustrative embodiment, a plasmid comprising nucleic acid sequences for expressing an siRNA for inhibiting SINE/Alu retrotransposon transcripts comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid is ultimately intended for use in producing a recombinant adeno-associated viral vector comprising the same nucleic acid sequences for expressing the siRNA.

As used herein, "in operable connection with a polyT termination sequence" means that the nucleic acid sequences encoding the sense or antisense strands are adjacent to the polyT termination signal in the 5' direction or sufficiently close so that during transcription of the sense or antisense sequences from the plasmid, the polyT termination signals act to terminate transcription after the desired product is transcribed.

As used herein, "under the control" of a promoter means that the nucleic acid sequences encoding the sense or antisense strands are located 3' of the promoter, so that the promoter can initiate transcription of the sense or antisense coding sequences.

In certain embodiments the siRNA can be delivered as a small hairpin RNA or short hairpin RNA (shRNA). shRNA is a sequence of RNA that makes a tight hairpin turn that can be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it.

In certain embodiments the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, etc., . . . up to about 19) nucleotides in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. In other words, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule can also comprise a 5'-terminal phosphate group that can be chemically modified. In addition, the loop portion of the shRNA molecule can comprise, for example, nucleotides, non-nucleotides, linker molecules, conjugate molecules, etc.

The shRNA/siRNA/piRNA described herein targets and causes the RNAi-mediated degradation of SINE/Alu retrotransposon transcripts, or alternative splice forms, or participates in genomic silencing via (PIWI RNA pathways). Thus, in certain embodiments, methods are provided for inhibiting SINE/Alu retrotransposon transcripts in a cell, comprising administering an effective amount of an SINE/Alu retrotransposon transcript siRNA/shRNA/piRNA to the cell, such that the target mRNA is degraded.

In various embodiments the siRNA/shRNA/piRNA can be expressed from recombinant viral vectors introduced into the subject cells. The recombinant viral vectors comprise sequences encoding the siRNA/shRNA and any suitable promoter for expressing the siRNA/shRNA/piRNA sequences. Suitable promoters include, but are not limited to, the U6 or H1 RNA pol III promoter sequences and the cytomegalovirus promoter. Selection of other suitable promoters is within the skill in the art. The recombinant viral vectors can also comprise inducible or regulatable promoters for expression of the siRNA/shRNA in a particular tissue or in a particular intracellular environment.

The siRNA/shRNA/piRNA can be expressed from a recombinant viral vector either as two separate, complementary RNA molecules, or as a single RNA molecule with two complementary regions.

Any viral vector capable of accepting the coding sequences for the siRNA/shRNA/piRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector can be pseudotyped with surface proteins from vesicular stomatitis virus (VSV), rabies, Ebola, Mokola, and the like.

Selection of recombinant viral vectors suitable for use in methods for inserting nucleic acid sequences for expressing the siRNA/shRNA/piRNA into the vector, and methods of delivering the viral vector to the cells of interest are within the skill in the art (see, e.g., Domburg (1995) *Gene Therap.* 2: 301-310; Eglitis (1988) *Biotechniques* 6: 608-614; Miller (1990) *Hum. Gene Therap.* 1: 5-14; Anderson (1998) *Nature* 392: 25-30, and the like).

In certain embodiments suitable viral vectors include, but are not limited to lentiviral vectors. In one illustrative embodiment, lentiviral shRNA constructs to knockdown genetic SINE/Alu transcript are designed. The shRNA sense and anti-sense strands are chemically synthesized and the strands are annealed with equal amounts of each other creating restriction site specific overhangs for cloning, and ligated into a vector (e.g., a HindIII and BglII digested, gel purified pENTR/pTER+ vector). Equal amounts of each construct is mixed with pLenti-CMV-GFP DEST vector in LR Clonase reaction to recombine cloned shRNA production elements into a destination vector according to the manufacturer's instructions (Invitrogen). The produced lentiviral plasmid is transformed into *E. coli* Stbl3 cells (Invitrogen) for amplification.

In certain embodiments suitable viral vectors include those derived from AV and AAV. In one illustrative embodiment, the siRNA/shRNA/piRNA is expressed as two separate, complementary single-stranded RNA molecules from a recombinant AAV vector comprising, for example, either the U6 or H1 RNA promoters, or the cytomegalovirus (CMV) promoter. A suitable AV vector for expressing the siRNA, a method for constructing the recombinant AV vector, and a method for delivering the vector into target cells, are described in Xia et al. (2002) *Nat. Biotech.* 20: 1006 1010.

Suitable AAV vectors for expressing the siRNA/shRNA, methods for constructing the recombinant AV vector, and methods for delivering the vectors into target cells are also described in Samulski et al. (1987) *J. Virol.* 61: 3096-3101; Fisher et al. (1996) *J. Virol.,* 70: 520-532; Samulski et al. (1989) *J. Virol.* 63: 3822-3826; U.S. Pat. Nos. 5,252,479 and 5,139,941; International Patent Application Nos. WO 1994/013788; and WO 1993/024641, and the like.

Sources of Cells.

Stem cells (e.g., adult stem cells, embryonic stem cells, cord stem cells, IPSCs, etc.) can be obtained according to standard methods well known to those of skill in the art. In certain embodiments, stem cells are also commercially available.

Differentiating Stem Cells.

In certain embodiments methods are provided for differentiating stem cells in which level or activity of SINE/Alu retrotransposon transcripts is reduced/inhibited. It is believed these stem cells can be differentiated into embryoid bodies or terminally differentiated cells using standard differentiation methods well known to those of skill in the art.

For example, in certain embodiments, removal of leukemia inhibitory factor (LIF) can result in the differentiation of the modified stem cells described herein (e.g., stem cells in which SINE/Alu retrotransposon transcripts are reduced/inhibited) into embryoid bodies.

Methods of differentiating stem cells are well known to those of skill in the art. For example, extract from infarcted myocardium contains biochemical factors that induce cardiomyocyte differentiation from bone marrow-mesenchymal stem cells (BM-MSCs) (see, e.g., Ge et al. (2009) *Biochem. Biophys. Res. Commun.,* 381(3): 317-321). Bone morphogenic factors (BMP4, BMP7, and BMP8b) can increase differentiation of human germ cells from human ES cells (see e.g., Gonsalves et al. (2006) *Stem Cells Dev.,* 15(6): 831-837). Primary cell cultures derived from adipose tissue or skeletal muscle differentiate into adipocytes when cultured in high glucose (see, e.g., Aguiari et al. (2008) *Proc. Natl. Acad. Sci., USA,* 105(4): 1226-1231). Interleukin-27 induces differentiation in hematopoietic stem cells (see, e.g., Seita et al. (2008) *Blood,* 111(4): 1903-1912).

With respect to neural cell differentiation, the neurotrophin family is one of the most important inducible signals for the differentiation. Among them, nerve growth factor is well known to induce neurogenesis, and neurotrophin 3 is involved in oligodendrocyte development. Another important differentiation signal family is the ciliary neurotrophic factor (CNTF)-leukemia inhibitory factor (LIF) cytokine family, which plays a pivotal role in regulating gliogenesis in the developing mammalian central nervous system. In addition, AICAR (5-aminoimidazole-4-carboxamide-1-β-D-ribofuranoside;) induces astroglial differentiation of neural stem cells (see, e.g., Zang et al. (2008) *J. Biol. Chem.,* 283(10): 6201-6208 and references therein).

A number of natural compounds are also known to induce differentiation of stem cells in vitro. Such compounds include, but are not limited to retinoic acid, PDGF, insulin, Arctigenin, ATRA (vitamin A), boswellic acid, bromelain and other proteolytic enzymes, CAPE, flavonoids (including apigenin, luteolin, quercetin, genistein, and daidzein), emodin, EPA and DHA, monoterpenes, resveratrol, 1,25-D3 (vitamin D3), and the like.

It is believed the pluripotent cells produced using the methods described herein can be subsequently induced to differentiate using methods well known to induce differentiation if iPSCs. In this regard it is noted that methods of differentiating induced pluripotent cells into $CD34^+CD43^+$ hematopoietic progenitors and $CD31^+CD43^-$ endothelial cells are described by Choi et al. (2009) *Stem Cells* 27: 559. These cells can be further separated into phenotypically defined subsets of primitive hematopoietic cells in a pattern of differentiation resembling that of ES cells. Methods of differentiating induced pluripotent cells into pancreatic insulin-producing cells are described by Zhang et al. (2009) *Cell Res.* 19: 429. After first generating PDX-1 positive progenitor cells, human iPS cells were further differentiated into pancreatic cells expressing MafA, Glut2, insulin, and in some cases, amylase and C-peptide. Functional cardiomyocytes demonstrating sarcomeric organization and expressing cardiac markers including Nkx2.5, cardiac Troponin T, atrial natriuretic factor, and myosin heavy and light chains, have also been derived from human iPS cells and are indistinguishable from those generated from ES cells (see, e.g., Zhang et al. (2009) *Circ. Res.* 104:e30). Electrophysiology experiments revealed that like ES cells, iPS cells differentiate into nodal-, atrial-, and ventricular-like phenotypes, and are responsive to the canonical cardiomyocyte beta-adrenergic signaling pathway. Both human ES and iPS cells were efficiently converted to neural cells using two inhibitors of TGF-beta/Smad signaling, Noggin and the drug SB431542 (Chambers et al. (2009) *Nat. Biotechnol.* 27: 275). The synergistic action of these two inhibitors resulted in $Pax6^+$ primitive neural cells that could then be further differentiated into neural crest, anterior CNS, somatic motoneurons, and dopaminergic neurons.

These approaches are intended to be illustrative and not limiting. Other methods of inducing differentiation of stem cells are well known to those of skill in the art.

In certain embodiments cells and compositions comprising cells that have been differentiated into embryoid bodies or further differentiated (e.g., terminally differentiated) are also contemplated. Such differentiated cells include but are not limited to embryoid bodies and/or progenitor cells and/or terminally differentiated cells that are differentiated into lineages for cardiomyocytes, blood cells, epithelial cells, osteoblasts, osteoclasts, chondrocytes, adipocytes, smooth muscle cells, nerve cells (neurons), glial cells, pancreatic β-cells, motoneurons, and the like.

EXAMPLES

The following examples are offered to illustrate, but not to limit the claimed invention.

Example 1

SINE/Alu Retrotransposon-Dependent Chromatin Changes Induce Ex-Vivo Aging of Human Adult Stem Cells In this example, we report mechanistic aspects of ex-vivo adult mesenchymal stem cell aging. Using genome-wide comparative analysis of repairable and persistent DNA damage in human adult stem cells as they traverse into the state of cellular senescence, we were able to uncover a new, unexpected functional role of retrotransposons in the complex pathways of cellular aging. We present evidence that a majority of repairable DNA damage in self-renewing human adult stem cells is distributed non-randomly and is enriched at retrotransposal repeats. Our data suggests that the misregulation of transcriptional activity of at least one class of human retrotransposons (SINE/Alu repeats) impairs the assembly of cohesin and condensin complexes in pericentric chromatin sites of γH2AX enrichment, thus interfering with cellular DNA repair machinery. The inability of adult stem cells to resolve pericentric DNA damage results in exit from self-renewal to senescence. We provide evidence that this event is reversible, and suggest a new mechanistic model wherein the loss of appropriate control of transcriptional activity in the retrotransposal portion of the human genome can directly or indirectly influence complex molecular events leading to the cessation of adult stem cell self-renewal and triggering their senescence.

Results

Replicative Senescence of Human Adult Mesenchymal Stem Cells

Figure 7A:
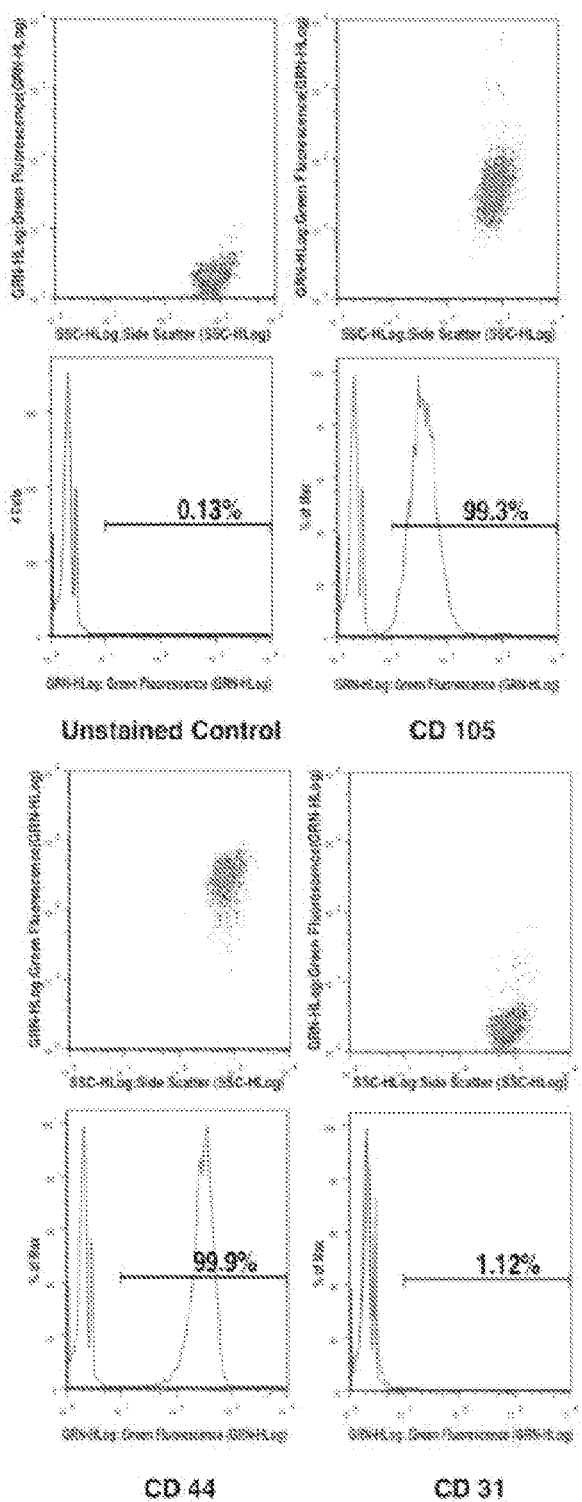

Human adult adipose derived mesenchymal stem cells (hADSCs) were isolated from subcutaneous abdominal fat as described in Experimental Procedures, and characterized based on cell surface antigens (FIG. 7A). After four weeks in the culture, the cells became more uniform as demonstrated by FACS analysis. More than 99.3% and 99.9% of the cells expressed mesenchymal stem cell MSC-specific cell type markers CD105 and CD44 (Dominici et al. (2006) Cytotherapy 8: 315-317), respectively, but did not express markers of hematopoietic stem cells (CD45) or endothelial progenitor cells (CD31) (FIG. 7A). hADSC can be induced to differentiate along several mesenchymal tissue lineages, including adipocytes, osteoblasts, myocytes, and chondrocytes (Erickson et al. (2002) Biochem. Biophys. Res. Commun. 290: 763-769; Zuk et al. (2001) Tissue Eng., 7: 211-228). Thus, hADSCs in these experiments bore strong resemblance to mesenchymal stem cells (MSCs).

Figure 1B:
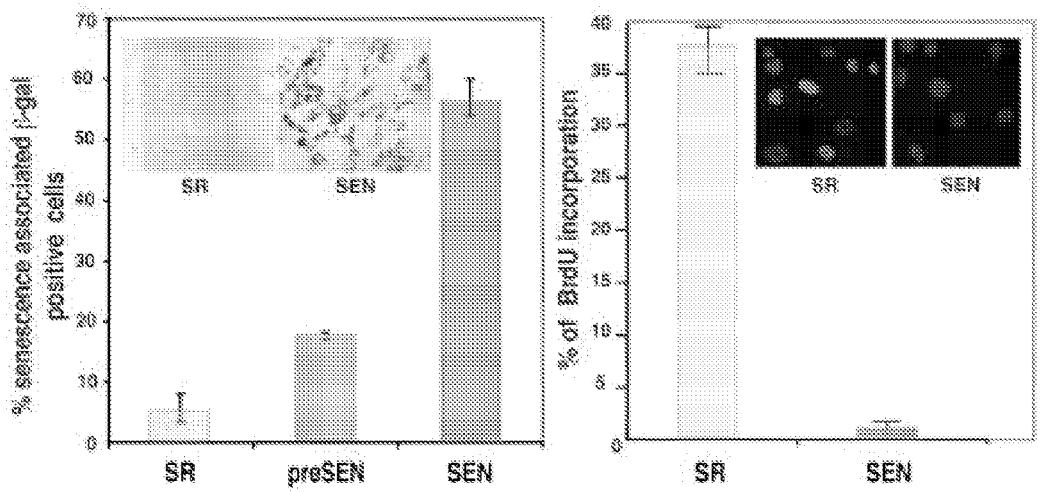

The self-renewing (SR) capacity of hADSCs remained consistent until population doubling (PD17), after which they displayed characteristic phenotypes of "old age" with prolonged ex vivo passages shown in FIG. 1A (and also described by (Bonab et al. (2006) BMC Cell Biol., 7: 14; Fehrer et al. (2007) Aging Cell, 6: 745-757; Kern et al. (2006) Stem Cells, 24: 1294-1301). The culture's morphological abnormalities are typical of the Hayflick model of cellular aging (Juckett (1987) Mech. Ageing Dev., 38: 49-71). By PD37, hADSC cultures accumulated non-dividing giant cells expressing the enzyme lysosomal pH6 senescence-associated J3-galactosidase (SA-J3-Gal) (Dimri et al. (1995) Proc. Natl. Acad. Sci. USA, 92: 9363-9367), as shown in FIG. 1B. Cells self-renewed poorly due to a decrease in the number of dividing cells as determined by incorporation of bromodeoxyuridine (BrdU) and $^3$[H] thymidine into DNA (FIG. 1B and FIG. 7B).

Figure 8:
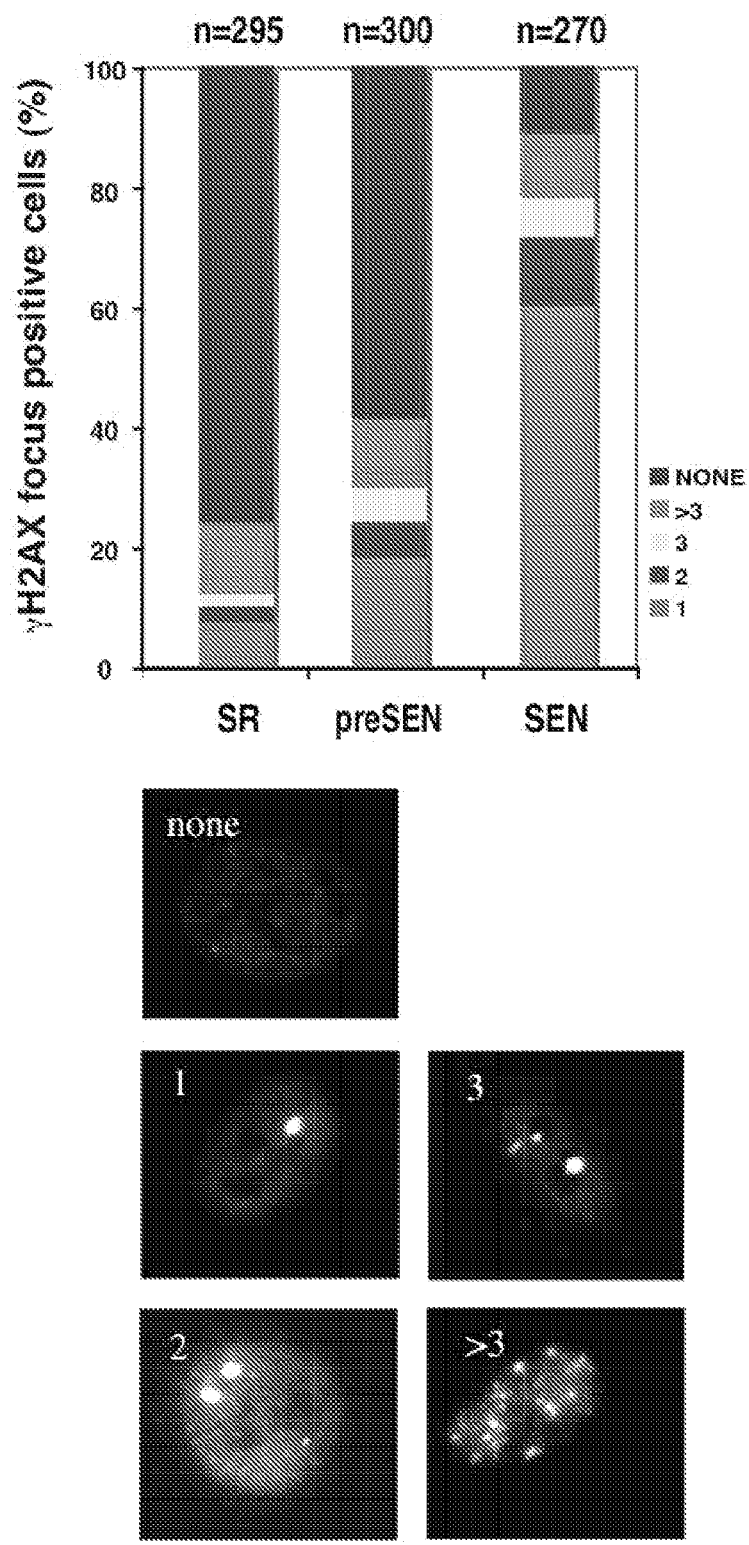
FIG. 8 shows quantification of accumulation of persistent DNA damage foci with ex-vivo passaging of hADSCs. $\gamma$H2AX was stained with affinity-purified rabbit polyclonal antibody. Histogram indicates the percentage of the cells with 1, 2, 3 or more than 3 foci. Representative examples are shown below. Foci formation was scored in self-renewing, SR (population doubling less than 17), pre-senescent, pre-SEN (population doubling more than 29, but less than 38) and senescent, SEN (population doubling more than 39) hADSCs cultures. n=total number of nuclei counted in all 3 independent experiments.

To determine if the hADSCs limited expansion capacity was due to senescence associated with persistent DNA damage accumulation, we performed immunostaining experiments with antibodies against key mediators of DNA damage response (DDR), which facilitate checkpoint activation and repair. In particular, we used a phosphorylated form of histone variant H2AX (γH2AX) (Shiloh (2003) Nat. Rev. Cancer, 3: 155-168) and p53 binding protein-1 (53BP1) (Aguilera and Gomez-Gonzalez (2008) Nat. Rev. Genet., 9: 204-217; Shiloh (2003) Nat. Rev. Cancer, 3: 155-168; Stewart (2009) Cell Cycle, 8: 1532-1538) to provide evidence of the presence of molecular characteristics of cells bearing DNA double-strand breaks (DSB) in both self-renewing and senescent hADSC cultures. As hADSCs approached senescence, both γH2AX and 53BP1 localized (FIG. 1C), forming characteristic foci, named persistent DNA damage foci (previously reported by Rodier et al. (2009) Nat. Cell Biol., 11: 973-979). Persistent γH2AX/53BP1 foci formation upon cellular senescence has been associated with the presence of unresolved DSB, as determined by colocalization with several DNA repair factors (d'Adda di Fagagna et al. (2003) Nature, 426: 194-198). Occurrences of γH2AX/53BP1 foci formations were very rare in self-renewing ADSCs, and their formation increased as cultured hADSCs approached senescence (SEN hADSCs) (FIG. 8).

Combined, these results reveal that senescence-associated effects in hADSCs are not restricted to senescent passages, but are continuously acquired from the onset of their ex-vivo expansion, similar to phenomena previously reported for human fibroblasts and human hematopoietic stem cells.

Figure 9:
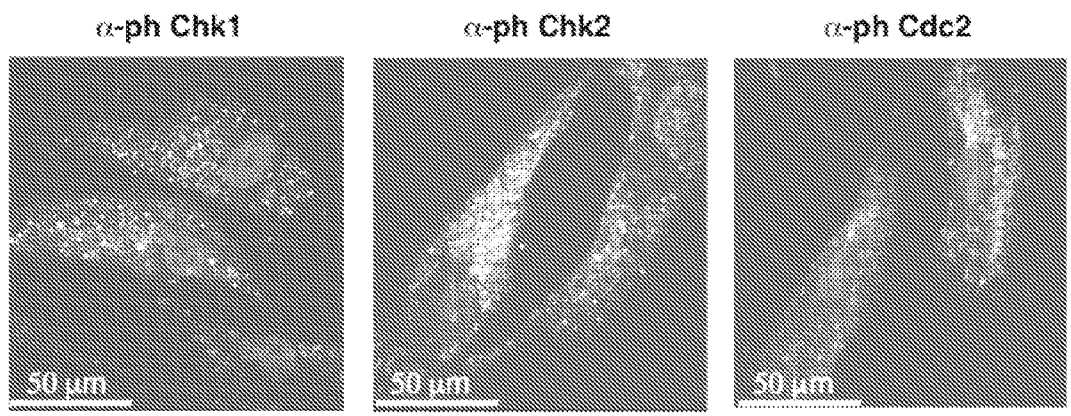
FIG. 9 shows DNA damage response activation in senescent hADSC. Senescent hADSC cultures were immunostained with antibodies against phosphorylated forms of Chk1 (S345), Chk2 (T68) and cdc2 (Tyr15) (brighter) and DAPI (dimmer). 50 mm confocal sections are shown. Chk1 and Chk2 are transducer kinases that act downsteam of ATM/ATR kinase to provide for DNA damage checkpoint control. Contrary to genotoxic stress or irradiation induced DNA damage, senescent hADSCs do not show robust nuclear localization of phosphorylated forms of Chk1 (S345) and Chk2 (T68).

We also noticed that senescent hADSCs contained activated forms of the DNA damage checkpoint kinases CHK1 and CHK2, phosphorylated on S345 and T68, respectively (FIG. 9). The phosphorylation of these sites by ATM/ATR is required for full execution of DNA-damage-induced cell-cycle arrest in human somatic cells (d'Adda di Fagagna et al. (2003) Nature, 426: 194-198; Sedelnikova et al. (2008) Aging Cell 7: 89-100; Tanaka et al. (2006) Cell Prolif., 39: 313-323). To further delineate the state of these cells, we performed differential (SR vs. SEN hADSCs) transcriptional analysis of the 96 genes involved in multiple aspects of the cell cycle (Human Cell Cycle qPCR array), described in detail in Experimental Procedures. Genes that were statistically significantly downregulated with a p value <0.05 in SEN hADSCs are shown in Table. 1, and include genes involved in cell cycle regulation, DNA replication, and mitosis, suggesting that senescent hADSC cultures follow a DDR program directly or indirectly related to the formation of senescence-associated DNA-damage foci. The causal factors that might mediate this process in human adult stem cells are as yet unknown.

Genome-Wide ChIP-Seq Location Analysis of γH2AX in Senescent hADSCs.

Figure 2A:
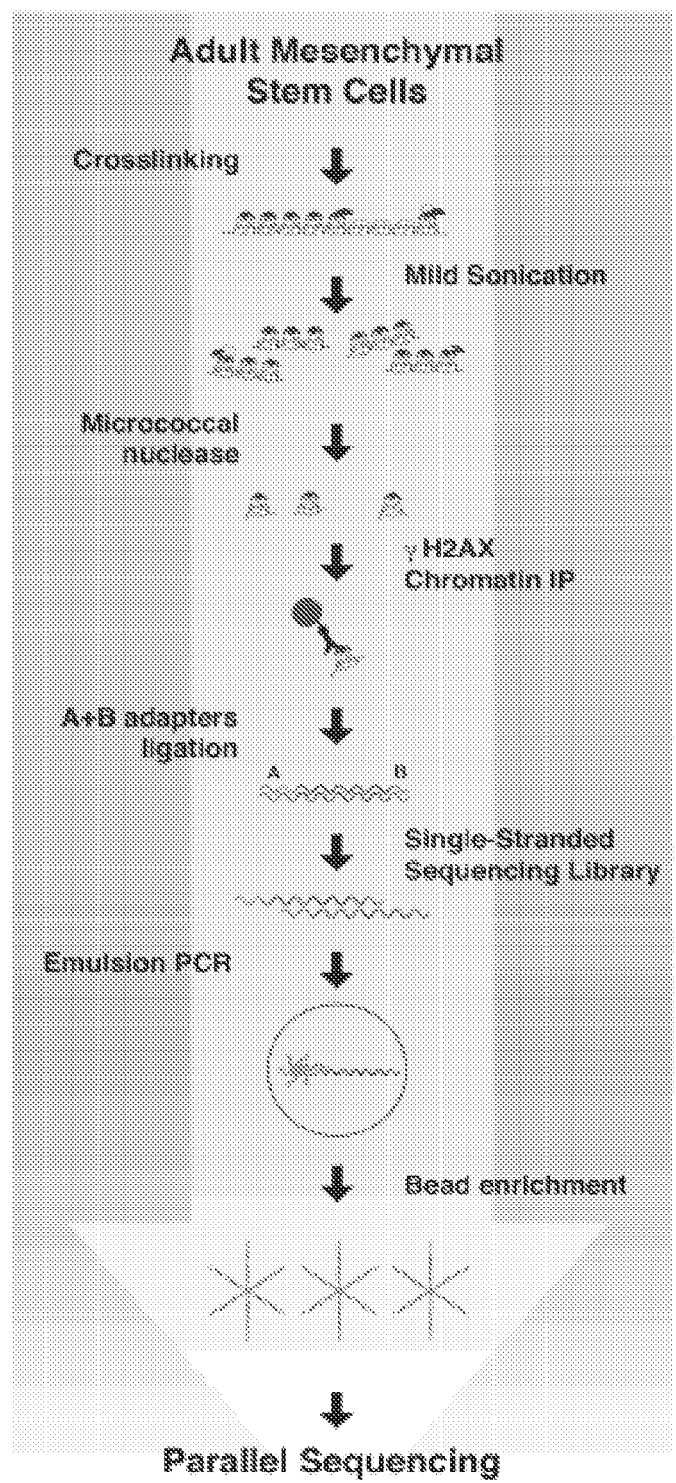
FIGS. 2A-2G illustrate genome-wide location analysis of γH2AX.

To identify genomic loci directly engaged in DDR in SEN hADSCs, we performed genome-wide profiling of hADSC chromatin using chromatin immunoprecipitation with an antibody against the γH2AX modified histone, followed by next generation sequencing (ChIP-seq) on the ABI SOLiD platform (FIG. 2A). Asynchronous SR samples of hADSCs were used in similar experiments to establish an overall representation of γH2AX modified chromatin, if any, to define the locations of repairable DNA damage which does not affect the SR properties of the cells. ChIP-seq was performed on four replicates each of SR and SEN hADSC cultures. Genomic mapping of the resulting sequence tags (Table 2) was followed by outlier removal, noise reduction, and merging of the data from replicate experiments. Details of the algorithms developed and approaches used for ChIP-seq data analyses can be found in Supplemental Methods. The ChIP-seq experimental protocol and data merging we employed were supported by the highly consistent mapping results seen for the replicate experiments. Having mapped and processed the ChIP-seq tags, we evaluated tag counts with respect to an empirically-derived count threshold (Supplemental Methods) for approximately mono-nucleosomal-sized windows of 200 bp in order to identify individual γH2AX modified nucleosomes on the human genome. The resulting genomic distributions of γH2AX modified nucleosomes were compared for SR and SEN cells (FIG. 2B) in order to assess the positional and quantitative changes in γH2AX modified chromatin associated with these phenotypes.

Majority of γH2AX Modified Chromatin Maps to the Retrotransposal Portion of the Human Genome Past studies reported that topological constraints on chromatin structures upon DNA replication and transcription pose the biggest danger to DNA integrity (reviewed in Shrivastav et al. (2008) Cell Res., 18: 134-147). Altogether, there are four potential sources of damage in aging adult stem cells: transient DSB generated by inducible gene transcription, DNA origin firing (Ju et al. (2006) Science, 312: 1798-1802; Ju and Rosenfeld (2006) Cell Cycle, 5: 2557-2560; Rampakakis and Zannis-Hadjopoulos (2009) Nucleic Acids Res., 37: 5714-5724), DNA damage resulting from impediments of replication forks due to collision of replication and transcription machineries, and difficulties arising from particularities in the replication of centromeric and telomeric regions of the genome (Dalal and Bui (2010) Curr. Opin. Cell Biol., 22: 392-402; Dotiwala et al. (2010) Curr. Biol., 20: 328-332; Morris and Moazed (2007) Cell, 128: 647-650; Schoeftner and Blasco (2009) EMBO J. 28: 2323-2336). Recent studies of γH2AX distribution in the genome of cycling Saccharomyces cerevisiae cells revealed "fragile" genomic locations (Szilard et al. (2010) Nat. Struct. Mol. Biol., 17: 299-305), suggesting that mapping sites of γH2AX enrichment could be fruitful to pinpoint at-risk genomic elements in other genomes. Since mechanistic aspects of "fragile sites" are linked to regulation of cell cycle checkpoints and DNA repair (Durkin and Glover (2007) Annu. Rev. Genet., 41: 169-192), one can expect that the gradual accumulation of unresolved DNA damage sites at these locations in asynchronously cycling cells can result in the triggering of cellular senescence.

Figure 2B:
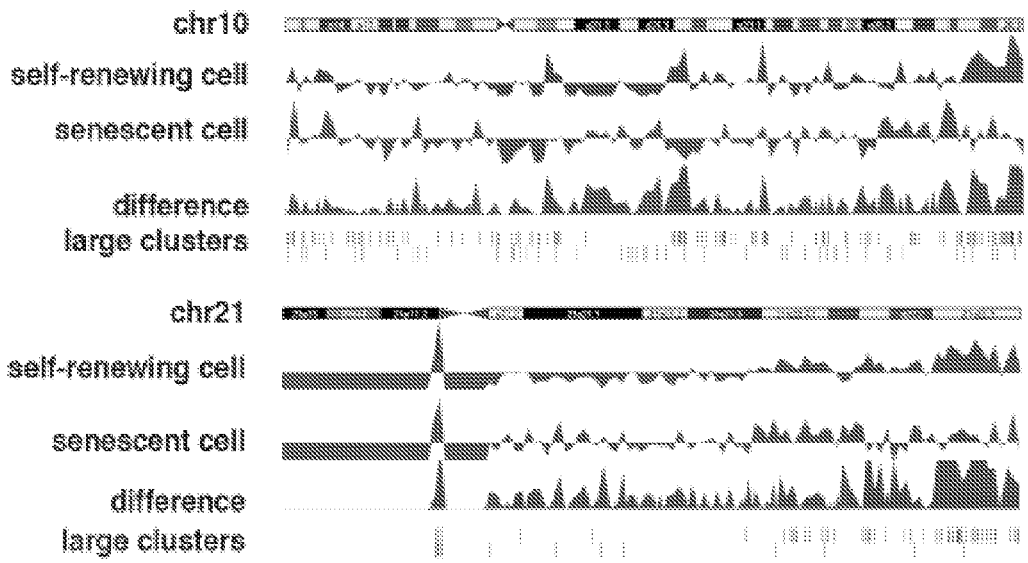
Figure 2C:
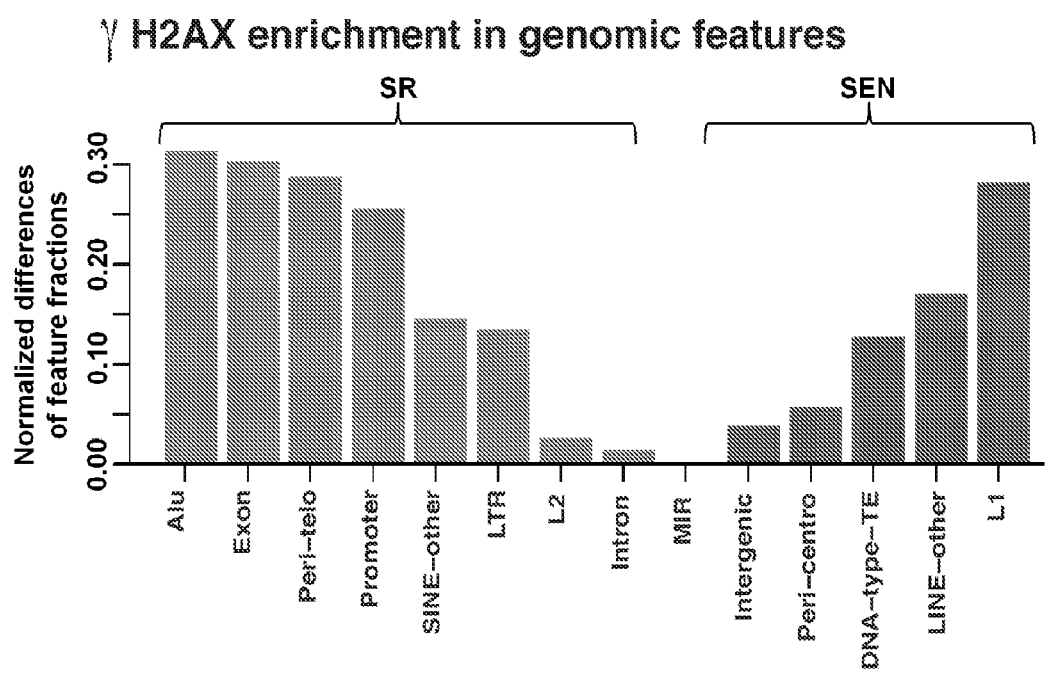
Figure 10:
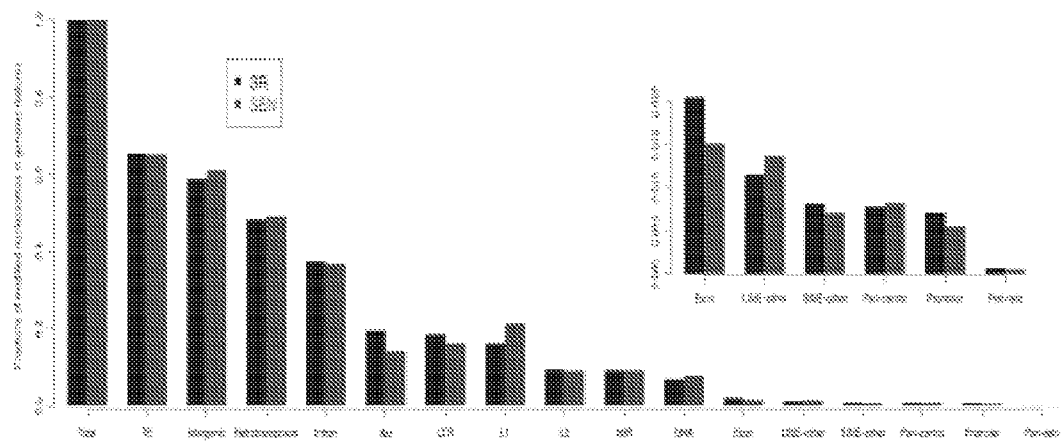
FIG. 10. Fractions of $\gamma$H2AX modified nucleosomes that map to different genomic features for self-renewing (SR left bars) and senescent (SEN right bars) adult adipose derived mesenchymal stem cells (hADSCs). The right tail of the distribution is enlarged and shown as an inset for clarity.

Our mapping experiments revealed that γH2AX modified chromatin was distributed non-randomly and, unexpectedly, represented a small fraction of total human chromatin in asynchronously cycling SR hADSCs: ~1.4% (200,977 γH2AX modified nucleosomes), and it represented an even smaller portion in SEN hADSCs: ~1.2% of total chromatin (173,877 γH2AX modified nucleosomes). The majority of γH2AX modifications (SR: 65.4%, SEN: 65.2%) mapped to transposable elements (TEs), most of which were SINE/Alu, L1, or LTR retrotransposons (FIG. 10). In addition to the overall abundance of retrotransposons bearing γH2AX modified nucleosomes, this genomic element also showed the greatest difference in relative frequencies of γH2AX marks for SR versus SEN hADSCs (FIG. 2C). SINE/Alu elements were the most enriched for γH2AX modified nucleosomes in SR cells compared to SEN cells, whereas L1s had the greatest relative increase of γH2AX modified nucleosomes in SEN cells (FIG. 2C). Apart from genic sequences, the retrotransposal portion of the genome is known to impede the progression of replication machinery (Scheifele et al. (2009) Proc. Natl. Acad. Sci. USA, 106: 13927-13932; Voineagu et al. (2008) Proc. Natl. Acad. Sci. USA, 105: 9936-9941; de la Loza et al. (2009) DNA Repair (Amst), 8: 620-626), suggesting that a portion of γH2AX detected in asynchronously dividing cells (SR sample) might be caused by replication-fork pausing or collapse as described previously in yeast (Admire et al. (2006) Genes Dev., 20: 159-173; Cha and Kleckner (2002) Science, 297: 602-606; de la Loza et al. (2009) DNA Repair (Amst), 8: 620-626; Deshpande and Newlon (1996) Science, 272: 1030-1033).

Our data suggest a role for retrotransposons in DNA damage-mediated cellular response related to normal cell cycle progression (Curcio et al. (2007) Mol. Cell Biol., 27: 8874-8885; Scheifele et al. (2009) Proc. Natl. Acad. Sci. USA, 106: 13927-13932), and imply that these elements may contribute to the aging phenotype in hADSCs (Rudin and Thompson (2001) Genes Chromosomes Cancer, 30: 64-71; Wang et al. (1999) Mutat. Res., 433: 147-157). Our data further corroborate the observation that the retrotransposal portion of the genome is particularly sensitive to DSB, a critical finding considering that this type of DNA breakage has been recently linked directly to genomic rearrangements in cancer (Eickbush (2002) Nat. Genet., 31: 126-127; Gosselin et al. (2009) Cancer Res., 69: 7917-7925; Lin et al. (2009) Cell, 139: 1069-1083; Rudin and Thompson (2001) Genes Chromosomes Cancer, 30: 64-71; Weinstock et al. (2006) DNA Repair (Amst) 5: 1065-1074).

Size and Distribution of γH2AX Chromatin in SR and SEN hADSCs

Previous studies have indicated that γH2AX forms within minutes of DSB formation and can cover large (thousands to millions of base pairs) regions of chromatin (Redon et al. (2003) EMBO Rep., 4: 678-684; Rogakou et al. (1999) J. Cell Biol., 146: 905-916). Therefore, we investigated the continuity of γH2AX chromatin in both asynchronously dividing SR and SEN hADSCs.

Figure 11A:
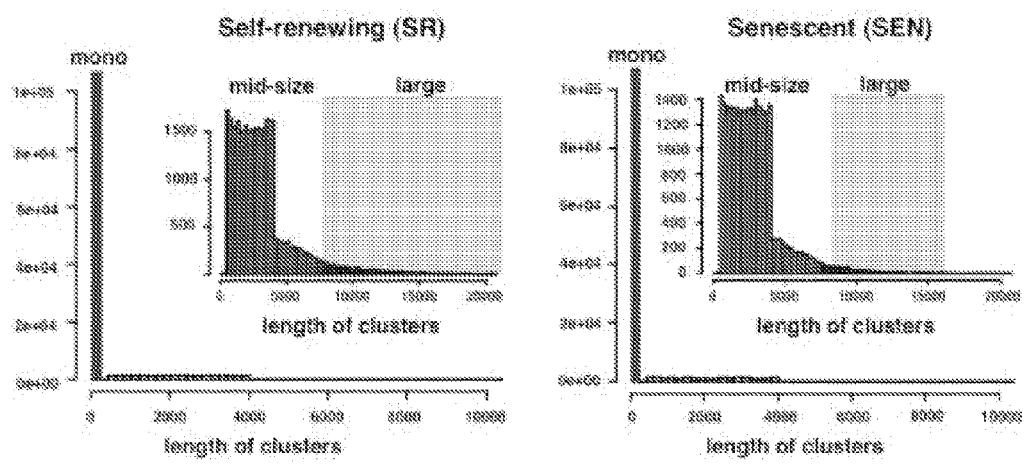
FIGS. 11A-11C show a comparison of mono-nucleosomal sized $\gamma$H2AX modified positions to genomic clusters of $\gamma$H2AX modified nucleosomes. $\gamma$H2AX modified mono-nucleosomes and $\gamma$H2AX modified clusters were identified as described in Supplemental Methods.

We developed a maximum segment-based algorithm to identify contiguous genomic regions that have anomalously high densities of γH2AX modified sites (Supplemental Methods). Such γH2AX-dense regions were taken to represent individual γH2AX chromatin clusters, and the distributions of the clusters were evaluated for SR and SEN cells. There was a single dominant γH2AX cluster size peak in both SR and SEN cells, which corresponded to approximately mono-nucleosomal-sized fragments that probably marked single DSB sites (FIG. 11A). The total amount of γH2AX mono-nucleosomal chromatin did not change significantly upon cellular senescence of adult stromal cells (FIG. 11B): there was ~21 MB of mononucleosomal sized chromatin in each cell type and the difference between SR and SEN cells was only ~0.6%. Our computational analysis did not reveal a particular genomic category that is significantly enriched for mono-nucleosomal damage accumulation upon cell cycle arrest in SEN hADSCs (Table 3). However, a majority of the mono-nucleosomal γH2AX sites (67.3% in SR and 65.8% in SEN) were associated with the retrotransposal portion of the genome, with SINEs contributing 34.9% and 30.0% and LINEs accounting for 32.4% and 35.78% of these sites in SR and SEN hADSCs, respectively (Table 3).

Figure 11B:
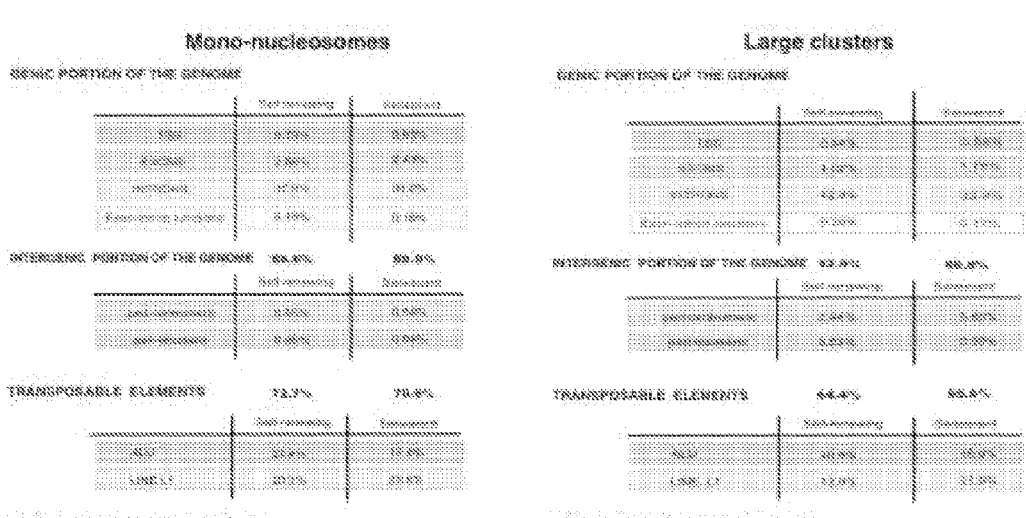
Figure 11C:
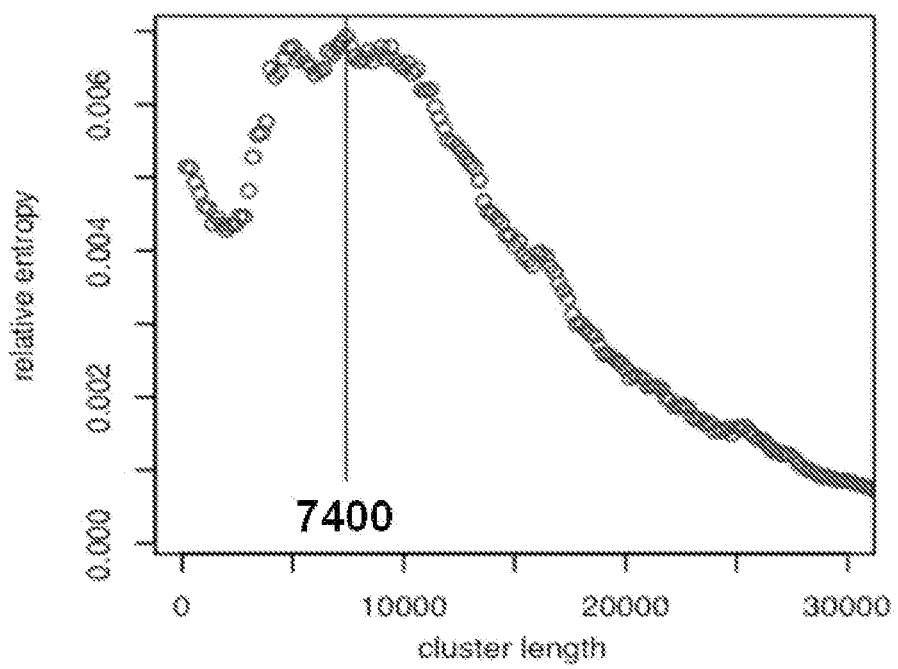

The γH2AX cluster size distributions were largely coincident for the majority of the clusters, but began to diverge substantially in tails of the distributions, which were occupied by the largest clusters (FIG. 11A). This difference between the SR versus SEN γH2AX cluster size distributions was used to delineate mid-size and large clusters. Relative entropy values, calculated as a measurement of the difference between the two distributions (Supplemental Methods), were calculated over a range of cluster length threshold values. The cluster length threshold value that maximized the relative entropy between the SR versus SEN γH2AX cluster size distributions was taken as a cut-off between mid-size and large clusters (FIG. 11C).

In contrast to what was observed for mono-nucleosomal sites, there were substantial differences in the amount of, as well as the genomic features occupied by, large γH2AX clusters. The total amount of large γH2AX clusters dropped more than three-fold from the SR (37,467,892 bp) to the SEN (11,243,429 bp) samples (FIG. 11B). In SR cells, 47.9% of large cluster chromatin was associated with the genic portion of the genome including: (i) gene promoters, (ii) introns, (iii) exons and, (iv) intron-exon junctions (Table 3). In SEN non-replicating samples, large γH2AX clusters were shifted to intergenic regions, with a decrease in genic sequences to 35.2%.

We hypothesized that this γH2AX deposition might result from topological problems arising from replication fork collision with transcription machinery. Our data support such a hypothesis since the dynamic of large clusters was shifted to intergenic regions in non-replicating SEN samples, with drastic decreases in exonic and intronic sequences. It is tempting to speculate that large genic and intergenic clusters of γH2AX might represent hot spots not only for chromosome fragility at the G2-M transition (SEN samples), but also for sister chromatid entanglement during the S phase of SR hADSCs.

γH2AX Chromatin and Gene Density

Transcriptional activity may represent an obstacle for progressing replication forks, resulting in their collapse and the accumulation of DSB (reviewed in Zegerman and Diffley (2009) *DNA Repair (Amst)* 8: 1077-1088). Therefore, functional genic regions such as exons and promoters are possibly relatively enriched with γH2AX modified nucleosomes in SR hADSCs, in contrast to SEN cells that have ceased their replication activity. Also, one may expect that gene-dense human chromosomes would be prone to γH2AX accumulation, and if this damage were not resolved during checkpoint activation, perhaps due to wear-and-tear of the DNA repair machinery, this could trigger the senescent phenotype. If this were the case, one would expect to observe γH2AX enrichment at similar locations within the chromatin of SR and SEN cells, and the amounts of γH2AX chromatin would be positively correlated with gene density in both phenotypes.

Figure 2D:
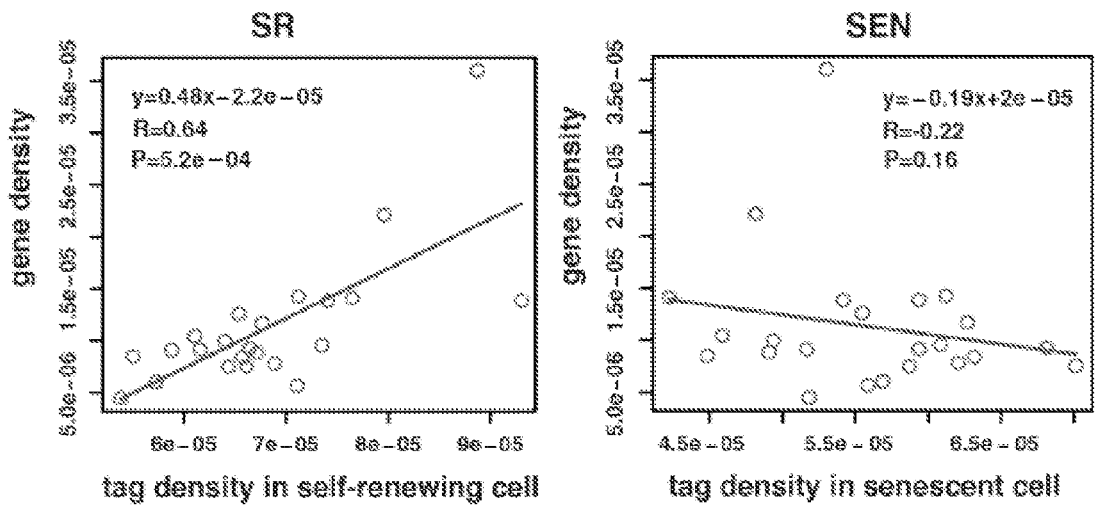

To test these two hypotheses, we evaluated the overlap between γH2AX chromatin sites in SR and SEN cells and compared the gene density of human chromosomes to the density of γH2AX sequence tags in SR and SEN cells. The overlap of γH2AX chromatin sites between cell types was small: ~5%. Gene density and γH2AX tag density were significantly positively correlated in SR samples, and negatively correlated in SEN samples (FIG. 2D and Table 4).

This difference in correlations for SR versus SEN cells is consistent with the transcription versus replication complex conflict model explaining the excess of genic-region-specific damage in SR hADSCs, and points out that the majority of damage in SEN cells is not related to unrepaired damage accumulation caused by the collision of replication forks and transcriptional complexes.

Figure 2E:
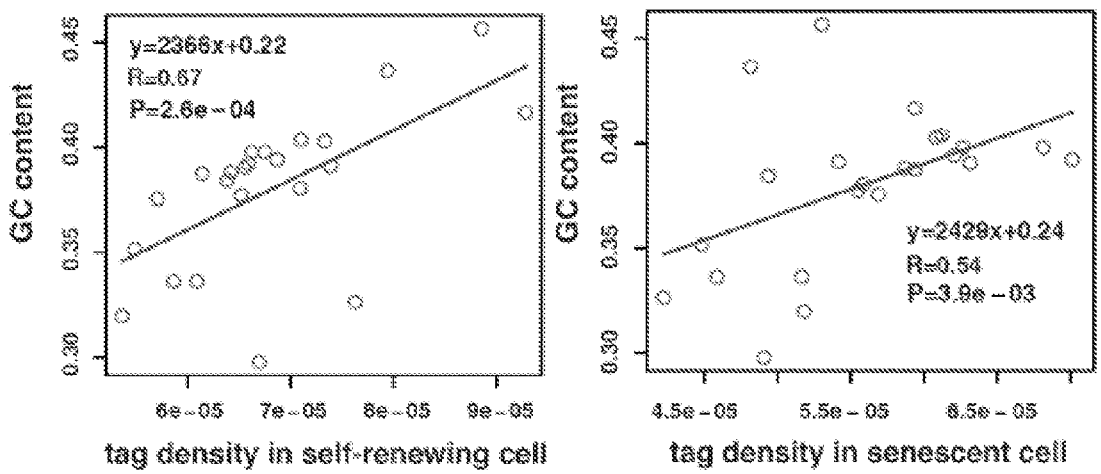

Considering that about 50% of γH2AX modifications are associated with the retrotransposal portion of the genome (FIG. 10), and it has been previously reported that the two most abundant categories of the retrotransposons, such as SINES and LINE, are differentially enriched in gene-dense and gene-poor chromatin (intergenic), respectively, with a bias toward GC-rich DNA (Lander et al. (2001) *Nature*, 409: 860-921; Mouse Genome Sequencing Consortium, Waterston et al. (2002) *Nature* 420: 520-562), we next investigated the correlation between γH2AX accumulation and the GC-content of human chromosomes. GC-rich genomic areas are also prone to the accumulation of DNA damage (Cha and Kleckner (2002) *Science*, 297: 602-606), but there is no a priori reason to expect a difference in GC-related damage accumulation between SR and SEN cells. Indeed, when chromosomal GC content and γH2AX tag density were compared, as was done for gene density, we observed significantly positive correlations for both SR and SEN hADSCs (FIG. 2E and Table 4). The positive correlation of GC content and γH2AX tag density in SEN cells stood in contrast to the negative correlation between gene density and γH2AX tag density in the same cells. This result is unexpected, since it is known that GC content is positively correlated with gene density. To tease apart these two genomic features, we performed a partial correlation analysis between gene density and γH2AX tag density in SEN cells by controlling for GC content. When partial correlation was performed in this way, the correlation between gene density and γH2AX tag density in SEN cells became more highly negative and statistically significant (Table 4).

Our data indicate a redistribution of γH2AX modified nucleosomes from genic regions in SR to non-genic regions in SEN hADSCs. This is consistent with what is seen when the relative enrichments of γH2AX modified nucleosomes are compared for SR and SEN cells genome-wide (FIG. 2C). The redistribution of γH2AX during senescence may also explain the excess of SINE/Alu-associated γH2AX modified nucleosomes in SR cells, since SINE/Alus are enriched in and around genes, along with the excess of L1 γH2AX modified nucleosomes in SEN cells, as L1s are primarily intergenic (FIG. 2C).

Promoter Distribution of γH2AX

Previously, transcriptional activation has been reported to require the formation of transient DSB in the promoters of inducible genes (Ju et al. (2006) *Science*, 312: 1798-1802). Later it was suggested that transcriptional misregulation upon cellular aging might stem from the inability to successfully repair DSB (Tower (2006) *Cell Metab.*, 4: 101-103). Under these conditions, the transient DSB in SR hADSCs would become persistent DNA damage sites in SEN cells.

Figure 2F:
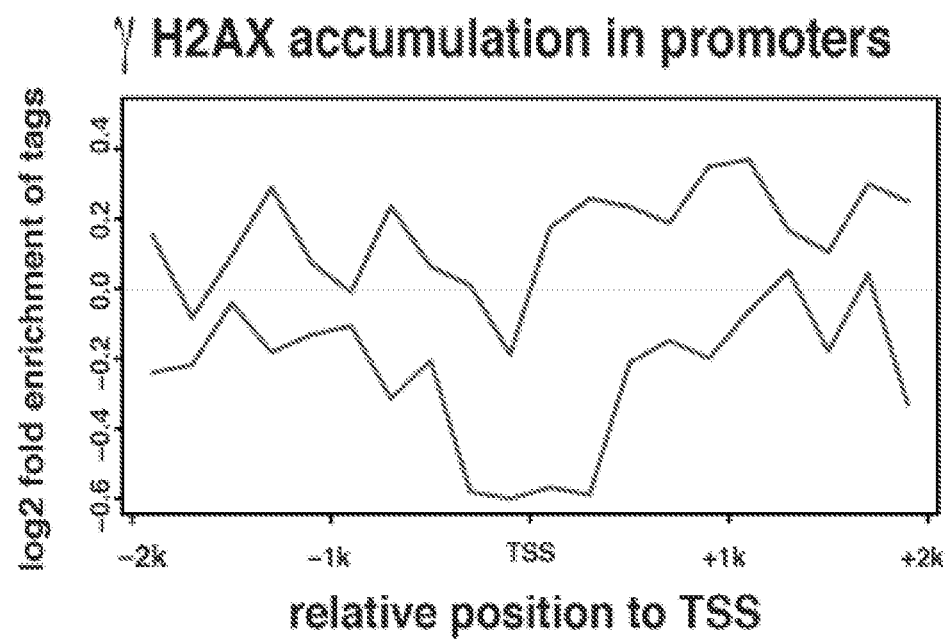
Figure 2G:
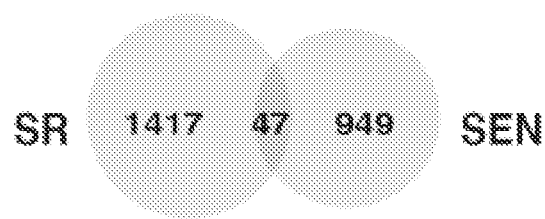

We observed significant changes in γH2AX accumulation within proximal promoter regions of protein-coding genes between SR and SEN cells. Consistent with the overall genomic distribution of γH2AX, there was a twofold increase in γH2AX accumulation in SR cell promoters than seen for SEN cells; ~3.9% of SR cell promoter sequences were occupied by γH2AX compared to 2.0% for SEN cells (Table 5). Furthermore, there was relatively little overlap in genes with γH2AX-modified promoters between SR and SEN cells (FIG. 2G). For both SR and SEN hADSCs, γH2AX showed periodic enrichment at specific positions from −2 kb to +2 kb relative to transcription start sites (TSS) (FIG. 2F). These enrichment patterns are consistent with nucleosome phasing around TSS in both SR and SEN cells; however, the distributions were shifted, suggesting a repositioning of γH2AX modified nucleosomes relative to TSS in SEN samples.

We evaluated genes with γH2AX modified promoters in SEN hADSCs (Table 6) in order to assess their potential impact on cellular function related to the aging phenotype. There were a number of over-represented gene ontology (GO) functional categories among this set of genes, including the related cell cycle (GO:0007049) and cell proliferation (GO:0008283) categories (Table 7). Genes in these categories have demonstrated effects on cell cycle progression and cell division (Table 8). When we performed a similar analysis for the group of cell cycle regulator genes (Table 1 and data not shown), we did not observe any correlation between senescence-associated downregulation of transcriptional activity of the genes and γH2AX accumulation in their promoters.

Our data suggest that down-regulation of tested cell cycle regulators in SEN hADSCs at the transcriptional level is not related to accumulation of DSB as previously proposed (Tower (2006) *Cell Metab.*, 4: 101-103).

Peri-Telomeric Distribution of γH2AX Chromatin and Human Adult Stem Cell Senescence Previous studies have reported that DSBs causing senescence in somatic cells arise directly from dysfunctional telomeres (Celli and de Lange (2005) *Nat. Cell Biol.*, 7: 712-718; d'Adda di Fagagna et al. (2003) *Nature*, 426: 194-198; Takai et al. (2003) *Curr. Biol.*, 13: 1549-1556). It was speculated that telomeric erosion might provide the reservoir of persistent DNA damage signal resulting in sustained p53 activation and manifestation of the SEN phenotype.

To ascertain whether dysfunctional telomeres are directly engaged in DDR in SEN hADSCs, we investigated the chromosomal enrichment of γH2AX in the telomeric and peri-telomeric areas of the human genome.

Telomeric regions are highly repetitive and have not been extensively characterized at the sequence level; therefore, we could not unambiguously map telomeric γH2AX ChIP-seq tags to the human genome. To evaluate γH2AX accumulation at telomeres, we therefore analyzed the counts of ChIP-seq tags that bore a specific telomeric repeat sequence motif (TTAGGG/AATCCC, (SEQ ID NO:9)) among all sequencing tags (mapped uniquely and unmapped due to their repetitive nature). SR cell samples had an average of 1.66% of such telomeric tags while SEN cells had 1.63%. These percentages did not reveal an over-representation of telomeric tags, and the difference between the two cell types was not significant.

Figure 3A:
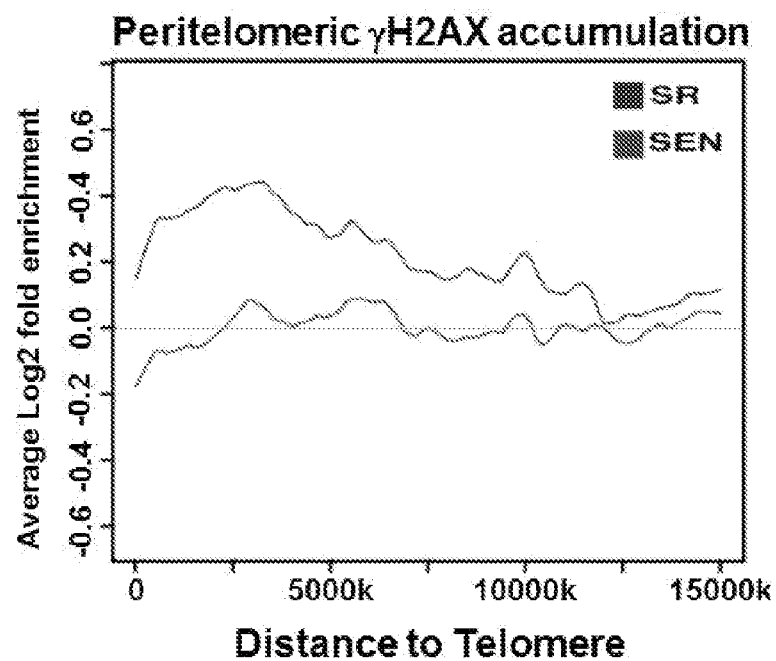
FIGS. 3A-3E show peri-telomeric and pericentric accumulation of γH2AX.
Figure 12:
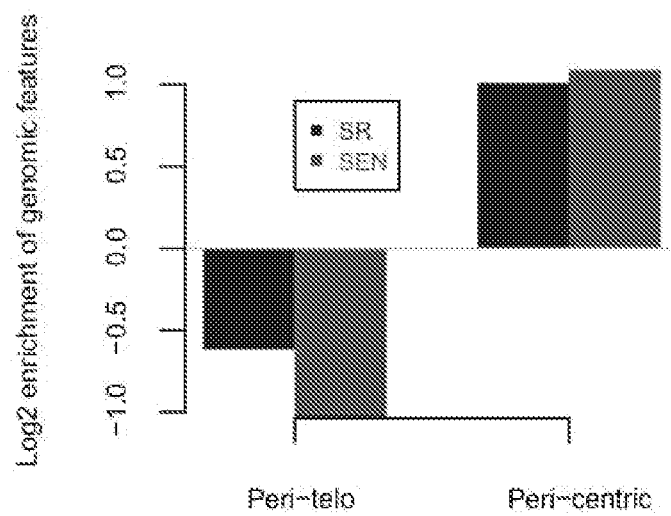
FIG. 12 shows relative enrichment of $\gamma$H2AX modified nucleosomes in peri-telomeric versus pericentric genomic regions. Enrichment values were calculated as log 2 normalized ratios of the $\gamma$H2AX ChIP-seq tag counts per position in each region divided the genomic background tag counts per position. Values for self-renewing (SR) cells are shown in blue and for senescent (SEN) cells in red. Peri-telomeric regions are depleted for $\gamma$H2AX, whereas pericentric regions are enriched FIG. 13, panels A-D, show persistent $\gamma$H2AX/53BP1 foci in senescent hADSCs are associated with centromeric regions. Panel A: Quantification of CENP-A and 53BP1 co-localization in senescence. Senescent hADSCs were stained with antibodies against CENP-A (green) and 53BP1 (red) and DAPI (blue). Total of 200 cells were scored from three independent experiments. Error bars represent +/−SAM. Example of higher magnification of the image is shown Panel B. Scale bar 1 tm. Images were analyzed by IMARIS software with optical sections representation as depicted in FIGS. 4C and 4D. D) Co-localization of senescence-associated persistent γH2AX/53BP1 foci with kinetochore. Double immunostaining of senescent hADSCs with antibodies against of γH2AX (panel C) or 53BP1 (panel D) and antisera to the inner kinetochore from patients with calcinosis, Raynaud's phenomenon, esophageal dysmotility, sclerodactyl, and telangiectasia (collectively abbreviated as CREST). Scale bars are shown for each individual image. Black and white images of the separate channels are given in (panel D) for the convenience of visualization.

We defined peri-telomeres as 100 kb regions from the end of the sequenced human chromosomes, and evaluated 15 Mb of genomic DNA extending into the chromosome arms for SR and SEN hADSCs (FIG. 3A). Overall, SR samples showed an enrichment of γH2AX over the entire region, while SEN samples were depleted for γH2AX. However, for both asynchronously cycling adult stem cells and for their SEN counterparts there was a marked decrease in the γH2AX density approaching and into the peri-telomeric regions (FIG. 3A). In fact, the total fraction of γH2AX modified chromatin found in peri-telomeres was quite small (SR=0.07%, SEN=0.05%; FIG. 10), but this could be due to the relatively small portion of the genome made up of peri-telomeres as defined here. To evaluate this possibility, we computed the genomic enrichment of γH2AX modified chromatin in peri-telomeres within SR and SEN cells as the fraction of modified chromatin normalized by the fraction of the genome occupied by peri-telomeric sequences. When peri-telomeric regions were evaluated in this way, they showed 1.5-fold (SR) and 2.1-fold (SEN) depletions in γH2AX modified nucleosomes (FIG. 12).

Figure 3B:
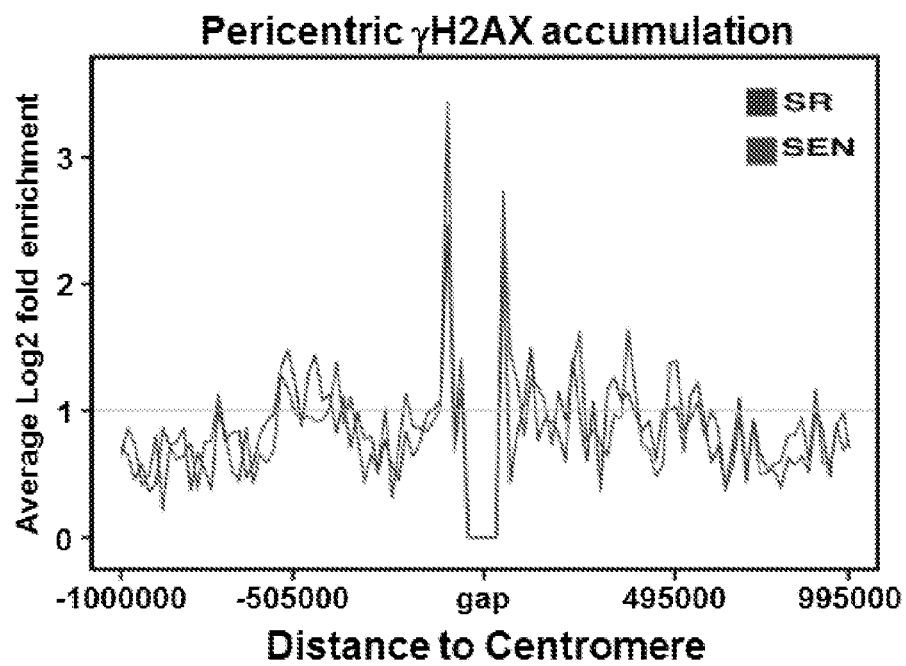
Figure 3C:
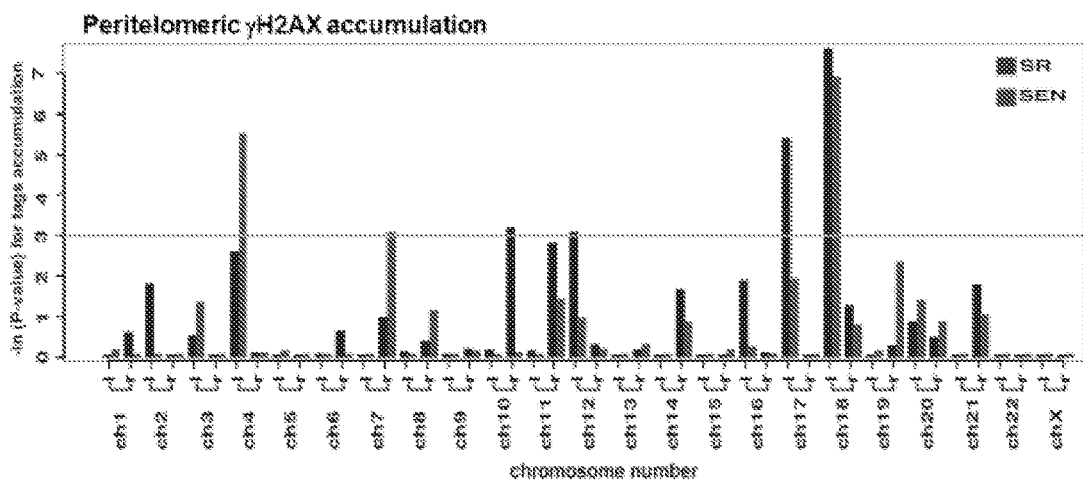

Our data support the notion that, contrary to what has been observed in human somatic cells (d'Adda di Fagagna et al. (2003) *Nature*, 426: 194-198), the aging of human adult stem cells might not be directly triggered by extensive peri-telomeric damage due to shortening of telomeres. This observation further corroborates findings previously reported (Sedelnikova et al. (2004) *Nat. Cell Biol.*, 6: 168-170). However, close inspection revealed a number of individual chromosomes with significant telomeric accumulations of γH2AX. The peri-telomeric γH2AX distribution on these chromosomes was markedly asymmetrical with respect to the chromosome arms (FIG. 3C). In SR cells, chromosomes 10, 12, 17, and 18 had γH2AX enriched telomeres, as did chromosomes 4, 7, and 18 in SEN hAD-SCs. Despite the differences in peri-telomeric γH2AX accumulation between SR and SEN cells, the chromosome arm asymmetry was always preserved. The relative levels of chromosome arm-specific γH2AX peri-telomeric accumulation were identical for SR and SEN cells (FIG. 3C).

Pericentric distribution of γH2AX

Compelling evidence indicates that pericentric chromatin is of critical importance for the regulation of kinetochore assembly, sister chromatid cohesion, spindle attachment, and chromosome segregation (Blower and Karpen (2001) *Nat. Cell Biol.*, 3: 730-739; Bernard et al. (2001) *Science* 294: 2539-2542; Schueler and Sullivan (2006) *Annu. Rev. Genomics Hum. Genet.*, 7: 301-313). Data in yeast also point to a causal relationship between fork stalling and chromosomal DSB in areas known as "replication slow zones" (RSZ) (Cha and Kleckner (2002) *Science*, 297: 602-606), many of which are associated with pericentric and centromeric chromatin. Also, spindle assembly checkpoint (SAC) acts semi-redundantly with the DNA damage checkpoint to enact long-term cell-cycle arrest in the presence of unresolved DSB, thereby preventing the segregation of the damaged chromatin (Dotiwala et al. (2010) *Curr. Biol.*, 20: 328-332; Elledge (1996) *Science*, 274: 1664-1672; Harrison and Haber (2006) *Annu. Rev. Genet.*, 40: 209-235; Lim et al. (2009) *Trends Cell Biol.*, 19: 325-333). Therefore, we further investigated whether human pericentric chromatin shows signs of fragility upon aging of adult stem cells, and whether or not it is resistant to γH2AX accumulation in cycling cells.

Figure 3D:
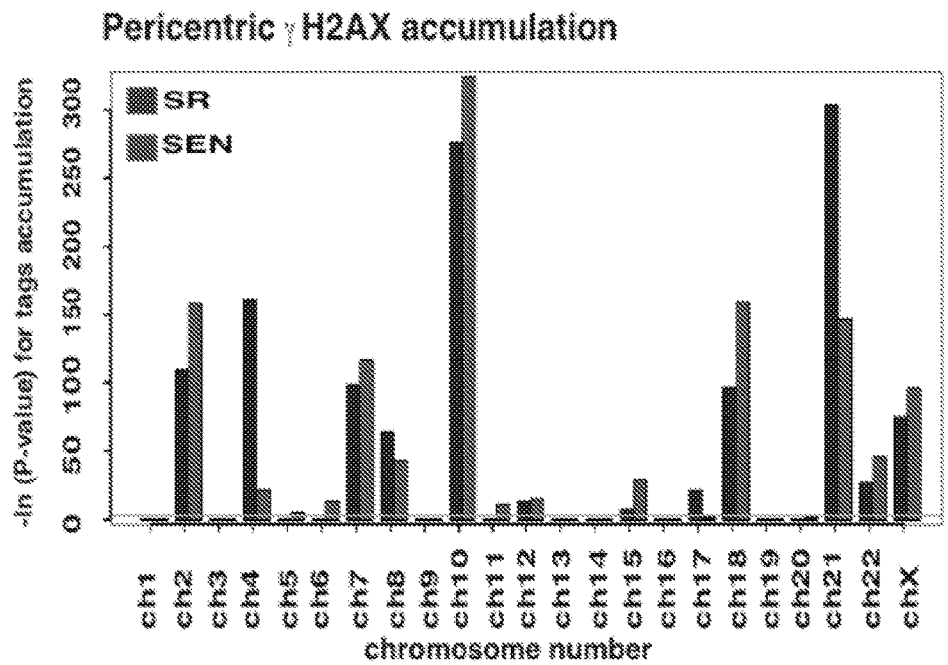
Figure 3E:
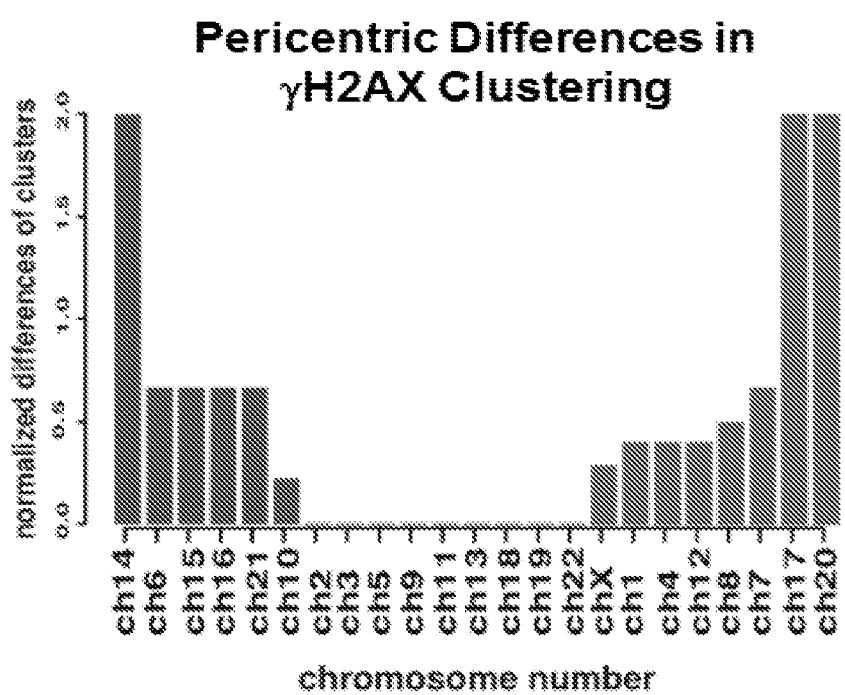

In our data, the distributions of γH2AX modified chromatin at peri-centromeric regions were markedly different from those seen for peri-telomeres. While peri-centromeres also contained a small fraction of the overall γH2AX modified chromatin across the genome (SR=0.78%, SEN=0.82%; FIG. 10), there was substantially more γH2AX modified chromatin in peri-centromeres than expected based on the fraction of the genome they occupy (FIG. 3B). Similar to chromosome-specific damage in peri-telomers, there were a number of individual chromosomes with highly enriched levels of peri-centromeric γH2AX accumulation (FIG. 3D). Overall peri-centromeres exhibited 2.0- and 2.1-fold enrichments for SR and SEN cells respectively (FIG. 12), thus indicating intrinsic susceptibility ("fragility") of these chromosomal regions. Peri-centromeres were not only enriched for γH2AX, but they were also one of the few genomic features that showed relatively greater γH2AX presence in SEN cells (FIG. 2B, FIG. 3D, 3E). Chromosomes 6, 14, 15, 16 and 21 demonstrated the most significant γH2AX enrichment in SEN cells (FIG. 3E).

Interestingly, our data did not reveal uniform and gradual accumulation of γH2AX in pericentric chromatin on the same chromosomes upon senescence, suggesting that damage accumulation in senescence is not necessarily a result of simply passing on a cell-cycle-associated defect in the DNA repair of these regions.

CENP-A and CREST Colocalization with Persistent DNA Damage Foci in Senescent ADSCs An increase in pericentric γH2AX accumulation only on a subset of human chromosomes in SEN hADSCs could be indicative of: i) unresolved DSB (possibly due to a change in the characteristics of their pericentric heterochromatin and the molecular machinery responsible for its repair), and/or, ii) defects in the assembly of kenetochore that provokes spindle-generated DNA damage, resulting in SAC (Guerrero et al. (2010) *Proc. Natl. Acad. Sci. USA*, 107:

4159-4164). Both of these events, acting separately or synergistically, might trigger senescence of human adult stem cells.

Figure 1C:
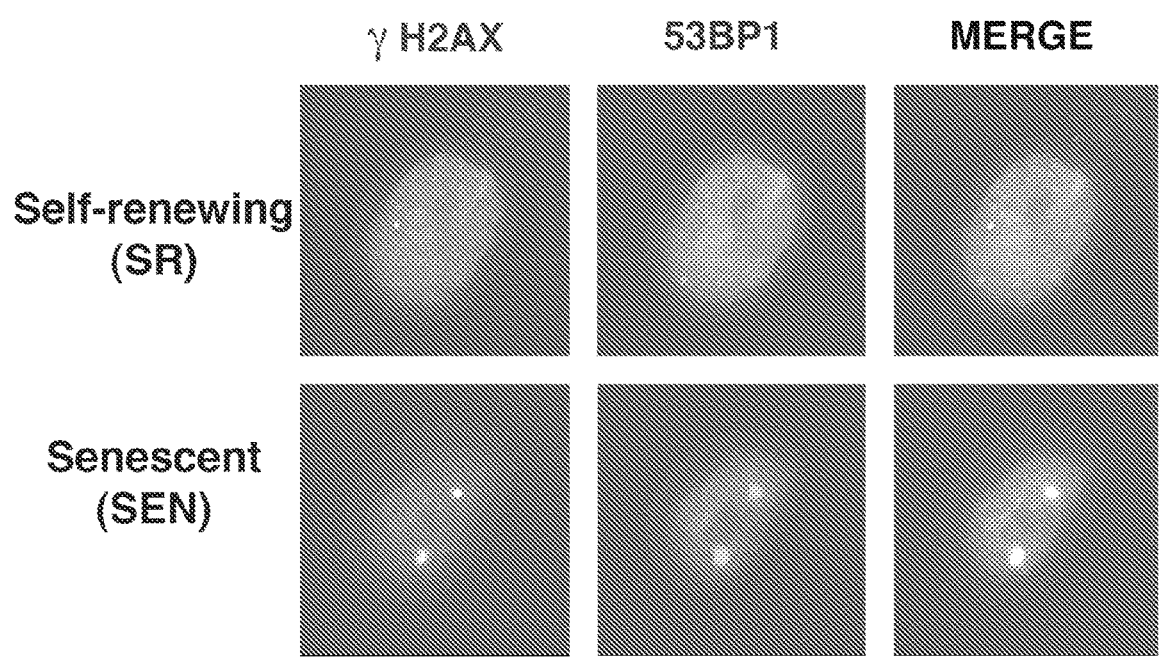
Figure 4:
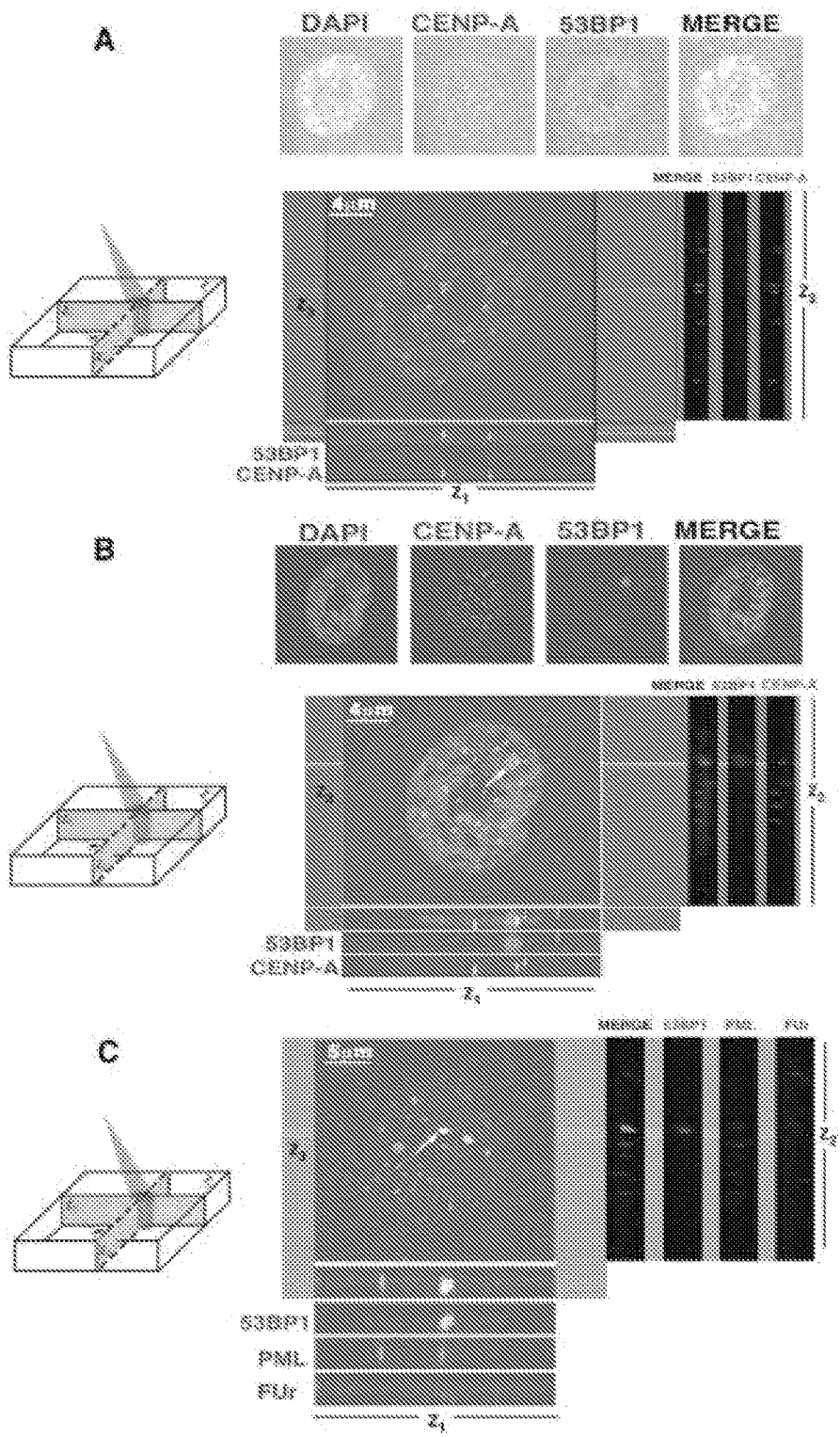
FIG. 4, panels A-C show centromere-associated persistent DNA damage foci in senescent hADSCs are sites of active transcription. Panel A: Immunofluorescent labeling of self-renewing hADSCs. Cells were seeded on coverslips and co-stained with anti-CENP-A (green) and anti-53BP1 (red) antibodies. DAPI staining is shown in blue. Confocal image of representative interphase nucleus is shown as separate channels and as a merged image. 4 μm z-slice was analyzed by Imaris software and z1, z2 and z3 projections are shown. Self-renewing hADSCs show no focal damage associated sites. Centromeric areas are clearly visible. Panel B: Persistent DNA damage is associated with centromeres. Senescent hADSCs were seeded on coverslips and as in (panel A), immunostaining was performed. An arrow depicts the co-localization of a centromeric region with persistent, senescence-associated γH2AX/53BP1 damage foci. Quantitation of these data and complementary co-staining with γH2AX are shown in FIG. 13. (Scale bar, 4 μm) Panel C: Association of persistent DNA damage sites upon senescence with regions of high transcriptional activity. Co-immunostaining of DNA damage foci depicted by 53BP1 antibodies (green) with PML bodies (blue) and nascent RNA (red) studied by confocal microscopy. Senescent hADSCs were incubated with halogenated precursor FUr for 10 min in vivo, fixed and stained with antibodies. BrdU antibodies were used to detect FUr labeled RNA. Representative image of a single nucleus is shown. Arrow points at the site of DNA damage focus co-localized with RNA. Spatial relationship between FUr incorporation sites, 53BP1 and PML bodies, is shown. Single 5 mm confocal section is shown. Image was analyzed by Imaris software and z1, z2 and z3 planes are shown. Cartoon demonstrates the orientations of z1, z2 and z3 planes within single z-section. Confocal sectioning confirms the tight association of nascent transcripts with persistent DNA damage sites in senescent hADSCs.
Figure 13:
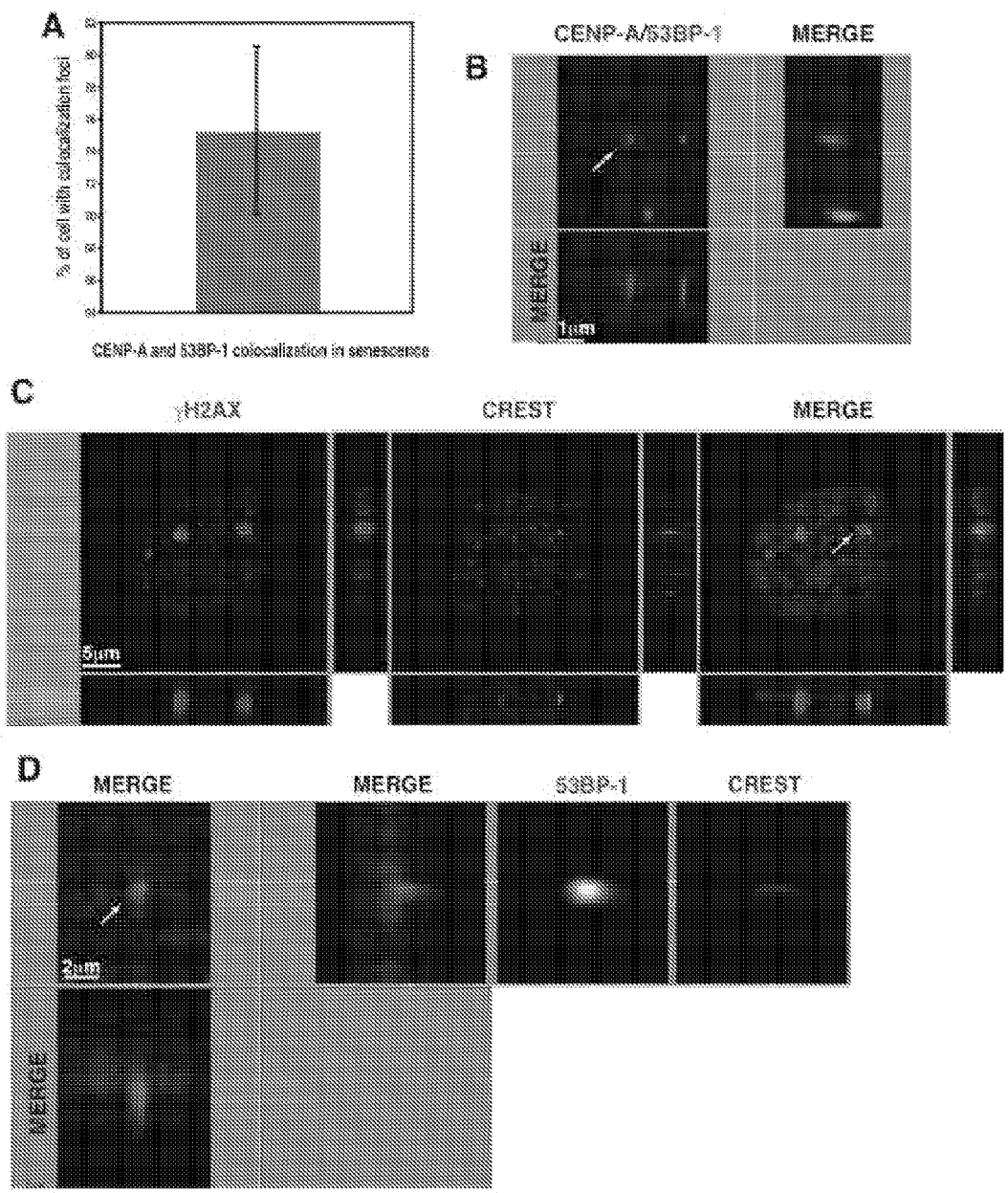

To uncouple these two possible scenarios, we first evaluated colocalization of central to kinetochore assembly centromeric histone H3 variant CENP-A with persistent γH2AX/53BP1 foci in SEN hADSCs. SR and SEN hADSCs were immunolabeled with antibodies to the 53BP1 and CENP-A proteins and studied by confocal fluorescent microscopy. In nearly 75% of the cases, CENP-A colocalized with large 53BP1/γH2AX in SEN hADSCs (FIG. 4A, B, FIG. 13A, B). Similar overlapping immunostaining patterns were observed when human anti-kinetochore serum (α-CREST) and anti-53BP1 antibodies or α-CREST and anti-γH2AX antibodies were assessed by confocal microscopy (FIG. 13C, D). As expected, we did not observe (detectable by our method) colocalization of centromeric regions with either 53BP1 (FIG. 4A) or γH2AX (data not shown) in interphase of SR hADSCs, since no prolonged cell cycle arrest was triggered in these cells (FIG. 1B, FIG. 7B) nor γH2AX/53BP1 foci were formed (FIG. 1C). Our data indicate that centromeric regions are embedded within persistent γH2AX/53BP1 DNA damage foci, formed upon senescence of hADSCs, and yet no defects in centromeric chromatin CENP-A incorporation/inner kinetochore assembly are observed. CENP-A is required to recruit many other centromere and kinetochore proteins (McClelland et al. (2007) *EMBO J.* 26: 5033-5047), with the exception of proteins located in adjacent heterochromatin domains, such as heterochromatic protein 1 (HP1) (Blower and Karpen (2001) *Nat. Cell Biol.*, 3: 730-739). We cannot rule out a possibility that defects in the other kinetochore/spindle components acting downstream of CENP-A affect the assembly of mitotic spindle, and that such deficiencies result in increased levels of γH2AX in peri-centromeric regions due to inappropriate chromosome segregation and cell cycle arrest (Dalton et al. (2007) *Cancer Res.*, 67: 11487-11492; Guerrero et al. (2010) *Proc. Natl. Acad. Sci. USA*, 107: 4159-4164; Quignon et al. (2007) *Oncogene*, 26: 165-172). In fact, we observed significant transcriptional downregulation upon hADSCs senescence of KNTC1 (hROD), a component of tension-sensitive kinetochore complex, known as the RZZ (Table 1) (Chan et al. (2000) *Nat. Cell Biol.*, 2: 944-947).

Senescence-Associated γH2AX Foci are Sites of Active Pol-III Transcription

There is a body of literature suggesting that pericentric chromatin is essential for the establishment and function of centromeres (Bernard et al. (1994) *Exp. Cell Res.*, 214: 373-380; Dalal and Bui (2010) *Curr. Opin. Cell Biol.*, 22: 392-402). In fission yeast, native pericentric chromosomal regions are permissive to RNA Pol-III (Chen et al. (2008) *Nature*, 451: 734-737; Scott et al. (2007) *PLoS One* 2: e1099), indicating a complex relationship between heterochromatic assembly, maturation of centromeric chromatin, and transcription. Mammalian chromatin modifying activities associated with cellular aging, such as sirtuins, have been previously reported to contribute not only to the formation of facultative heterochromatin (Vaquero et al. (2007) Nature 450, 440-444), but to also be involved in the mediation of repression at constitutive heterochromatic regions such as pericentromeric chromatin. Importantly, the generation of DSB by oxidative stress leads to increased transcription of pericentric satellite repeat DNA in a model of mammalian embryonic stem cells (Oberdoerffer et al. (2008) *Cell*, 135: 907-918).

With this in mind, we investigated the possibility of transcriptional activity associated with persistent γH2AX/53BP1 foci in SEN hADSCs. We combined the transcriptional assay of 5-fluorouridine (5-FUr) incorporation with detection of the 53BP1 and promyelocytic leukemia (PML) proteins upon senescence of hADSCs (described in Experimental Procedures and Casafont et al. (2006) *Neuroscience*, 140: 453-462). Nuclear incorporation of a halogenated nucleotide analog into nascent RNA was visualized in the whole nucleus by immunocytochemistry with an anti-BrdU antibody (Boisvert et al. (2000) *J. Cell Biol.*, 148: 283-292). We chose a specific nuclear compartment, PML body, since it has been suggested to play a role in aspects of transcriptional regulation and/or protein segregation (Carbone et al. (2002) *Oncogene* 21: 1633-1640; Dellaire et al. (2006) *J. Cell Biol.*, 175: 55-66; Dellaire et al. (2009) *Cell Cycle*, 8: 3750-3769). We observed a close juxtapositioning of PML nuclear bodies and senescence-associated persistent 53BP1 foci (FIG. 4C). Nascent RNA transcripts visibly decorated the periphery of the PML nuclear body and showed clear colocalization with the 53BP1 signal (FIG. 4C). These observations are consistent with previous reports indicating a possible involvement of RNA in 53BP1 foci formation after IR-induced damage in NIH3T3 and Hela cells (Pryde et al. (2005) *J. Cell Sci.*, 118: 2043-2055).

Figure 14:
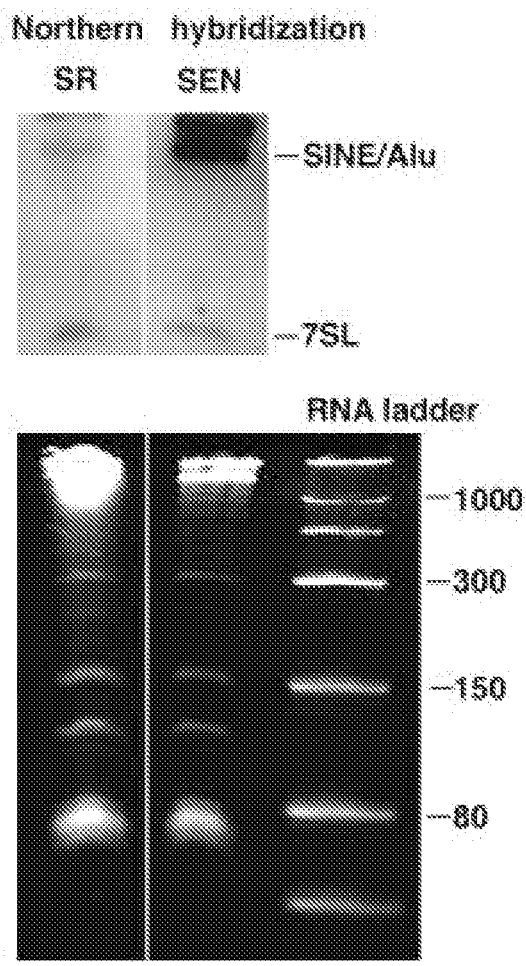
FIG. 14 illustrates SINE/Alu expression in SR and SEN hADSCs. Northern hybridization of self-renewing (SR) and senescent (SEN) hADSCs with SINE/Alu oligonucleotide probe. SINE/Alu and 7SL are indicated. Total RNA of 2 µg per lane was loaded as described in Experimental Procedures. Ribosomal small RNAs can be seen in the ethidium bromide stained gel for loading comparison. The ssRNA ladder sizes are indicated on the right.
Figure 15A:
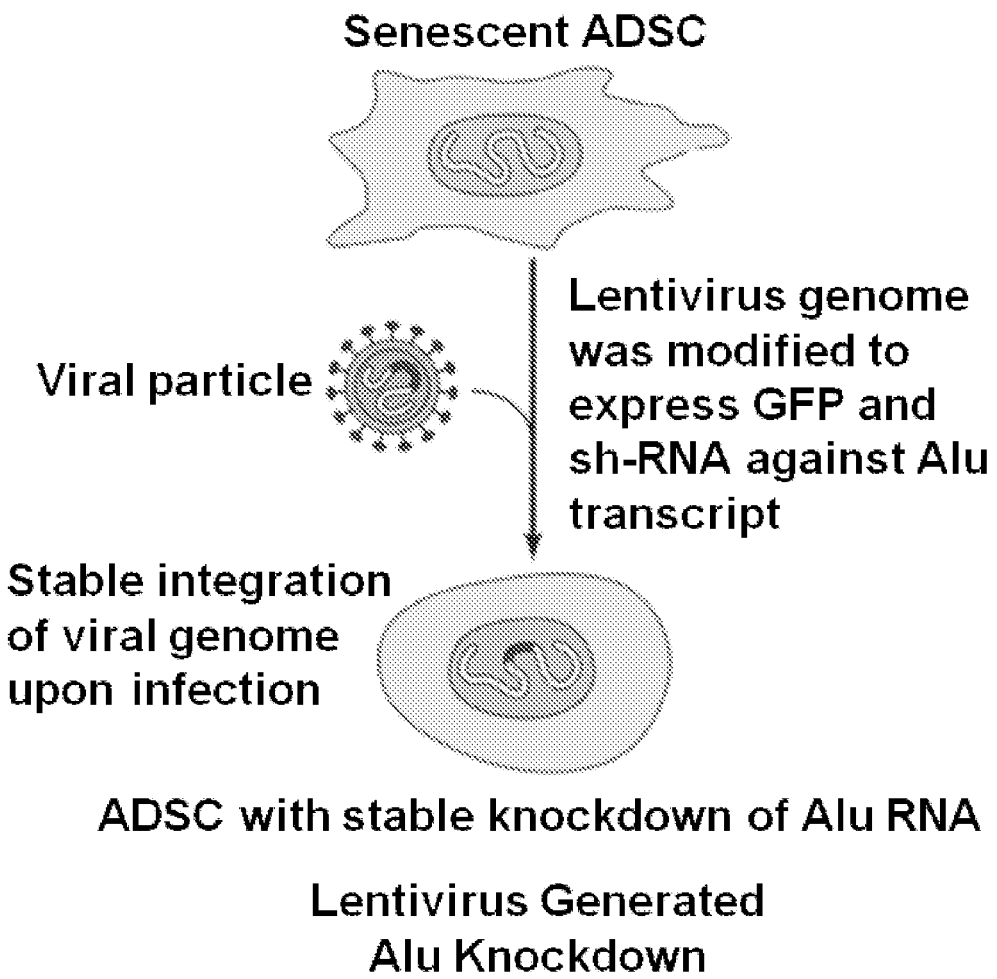
FIGS. 15A and 15B illustrates lentiviral shRNA-mediated knockdown of generic Alu transcripts in ADSCs and the effects of such knock down on cell senescence and proliferation.
Figure 15B:
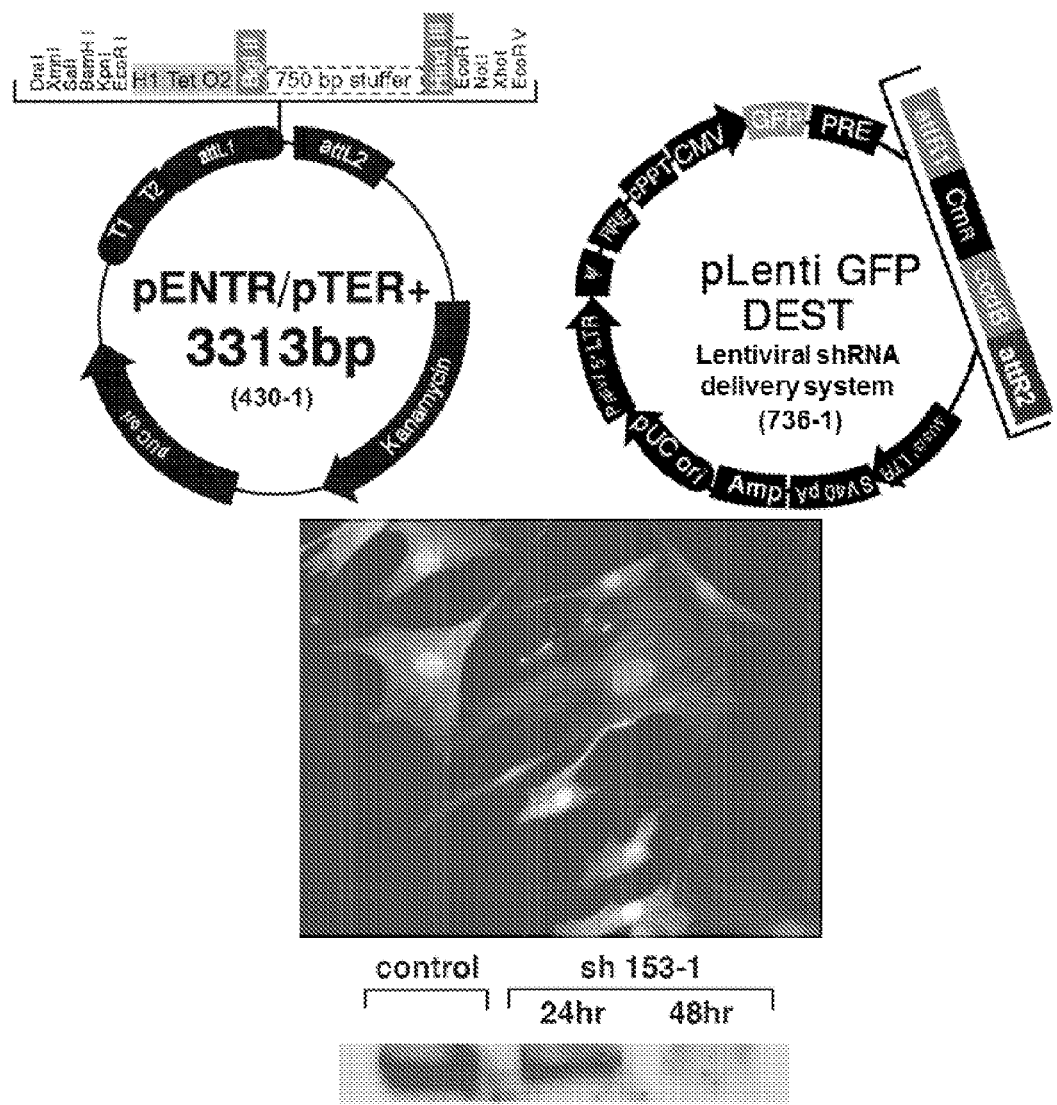
Figure 16:
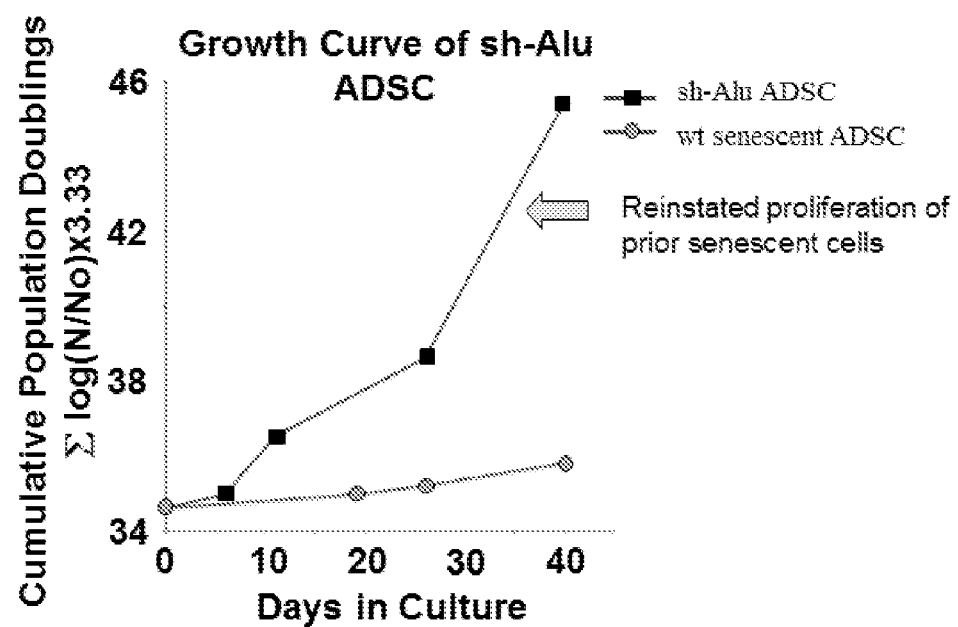
FIG. 16 illustrates the effect of lentiviral shRNA-mediated knockdown of generic Alu transcript in ADSCs. Cell proliferation is show as a function of time. Knockdown of Alu transcript reinstated proliferation of prior senescent cells.
Figure 17:
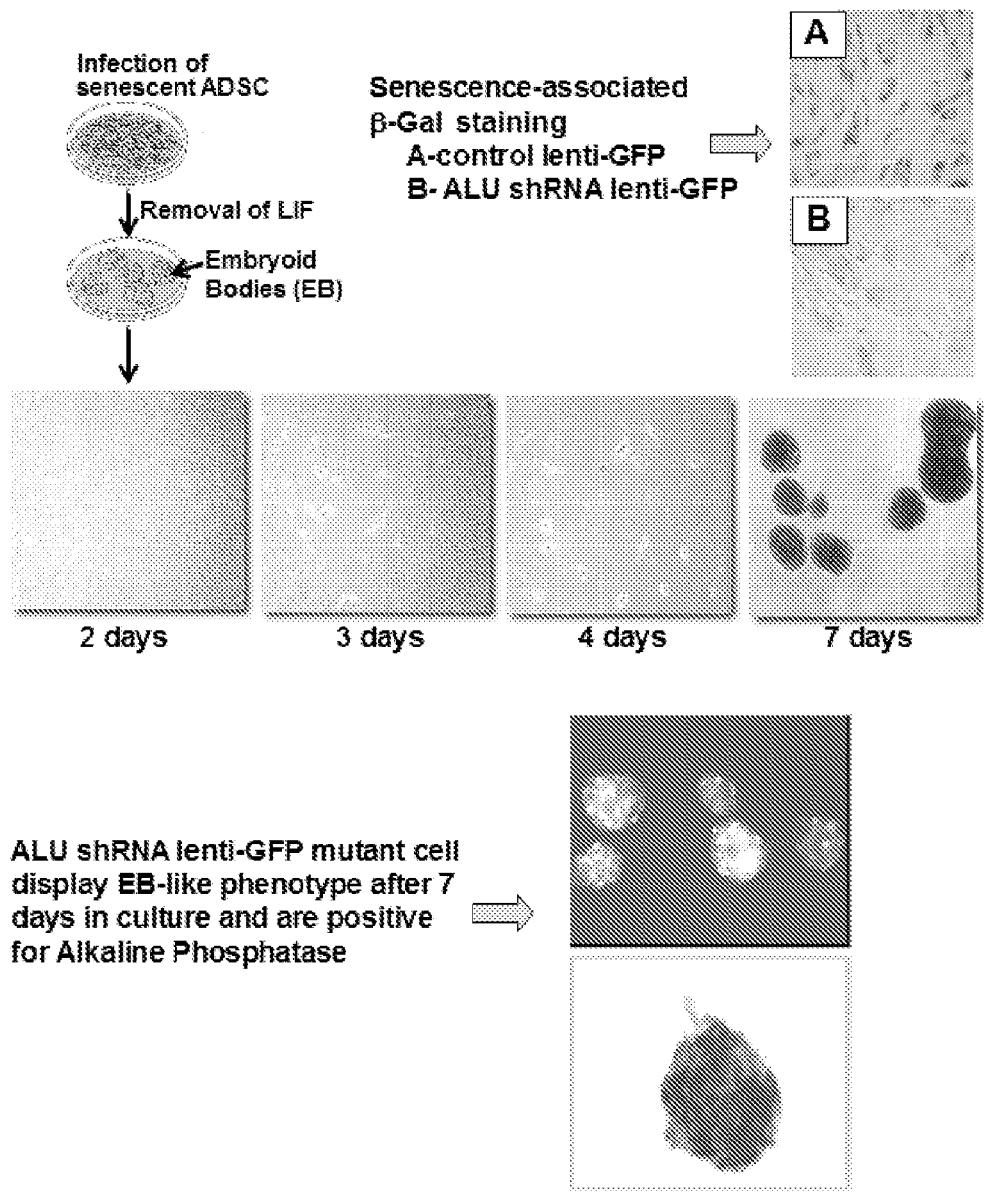
FIG. 17 illustrates the morphology of Alu shRNA mutant ADSCs in culture and their initial characterization.
Figure 19A:
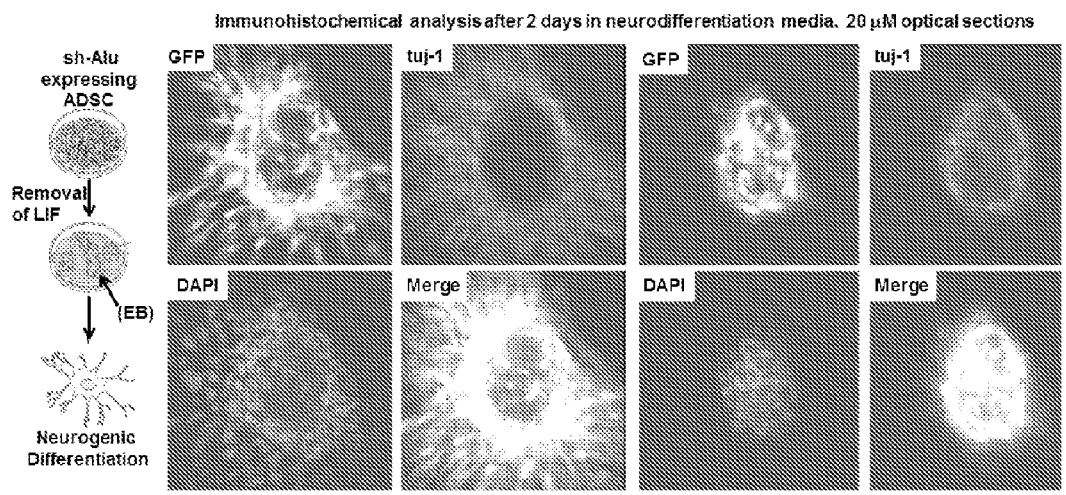
FIGS. 19A and 19B illustrate the subsequent differentiation of Alu shRNA mutant cells.
Figure 19B:
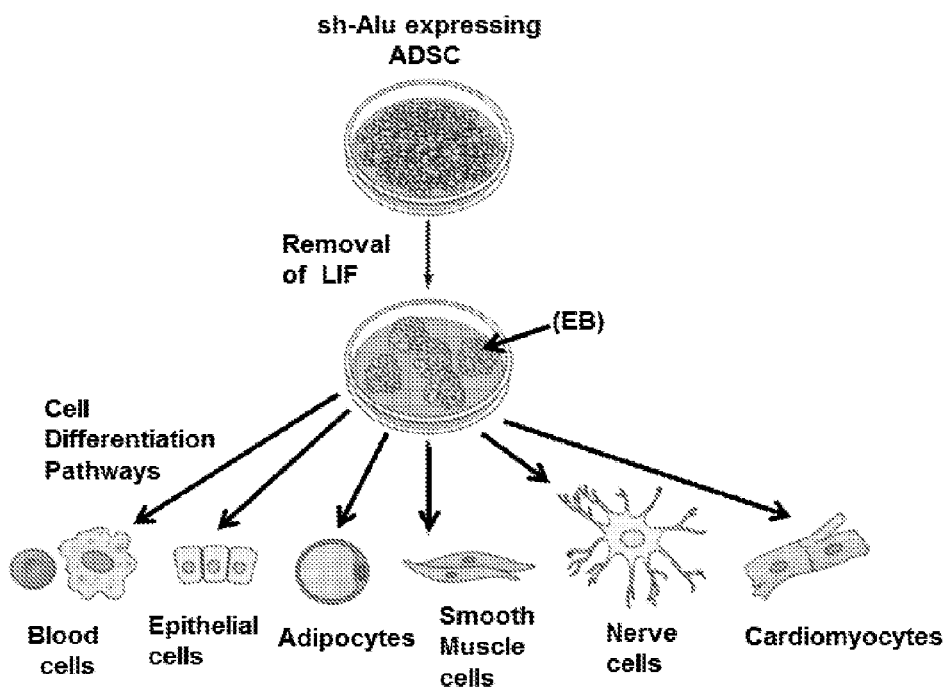
Figure 20A:
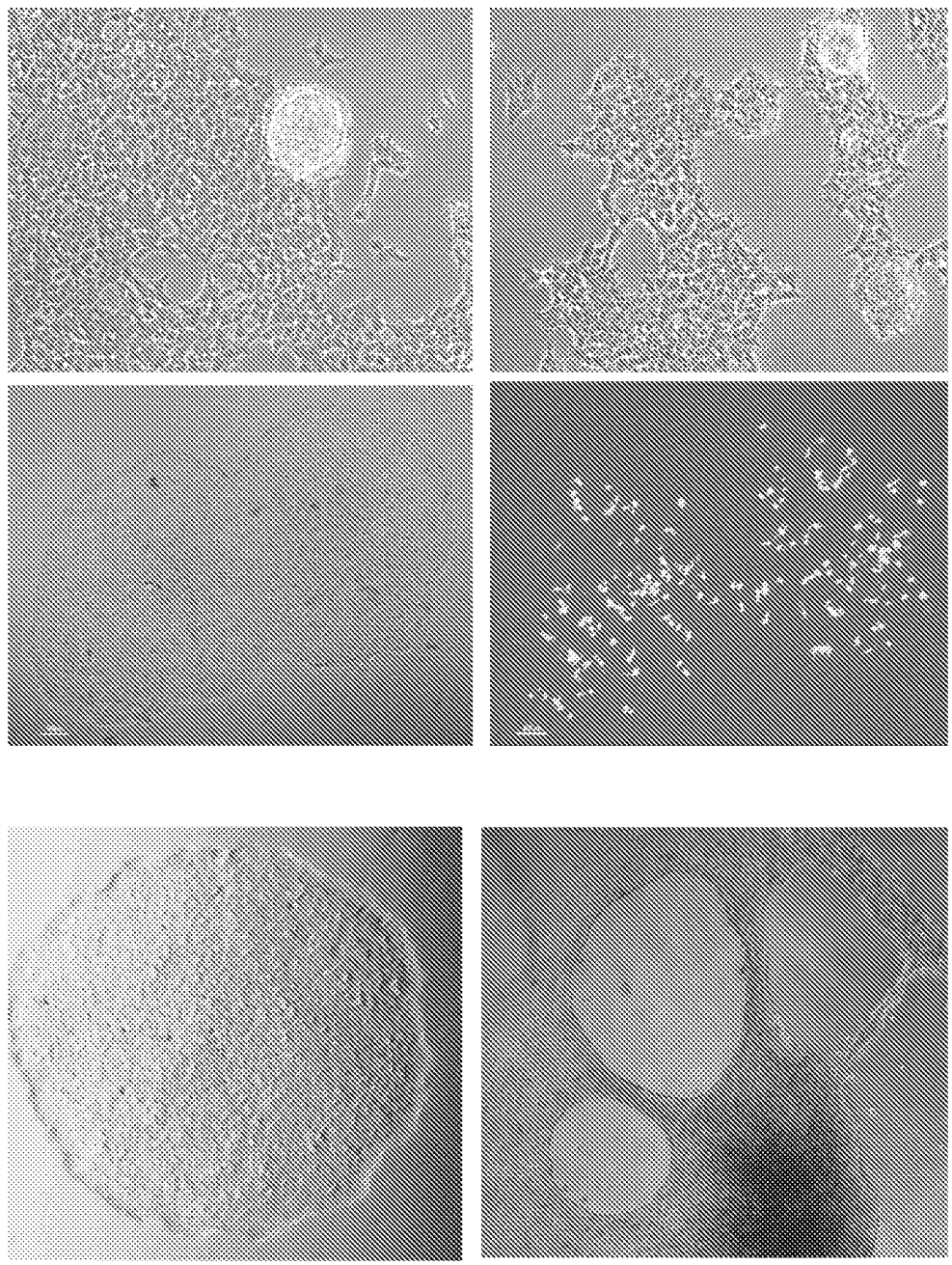
FIGS. 20A-20E illustrates the transdifferentiation of kidney fibroblasts into neuroblasts.
Figure 20B:
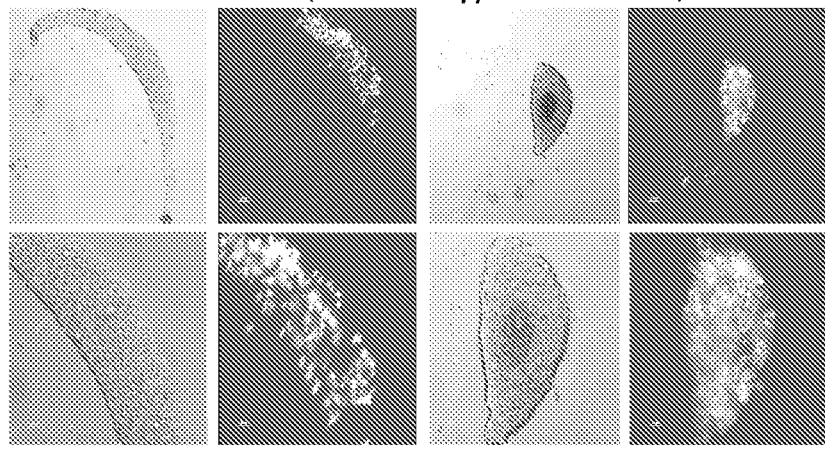
Figure 20C:
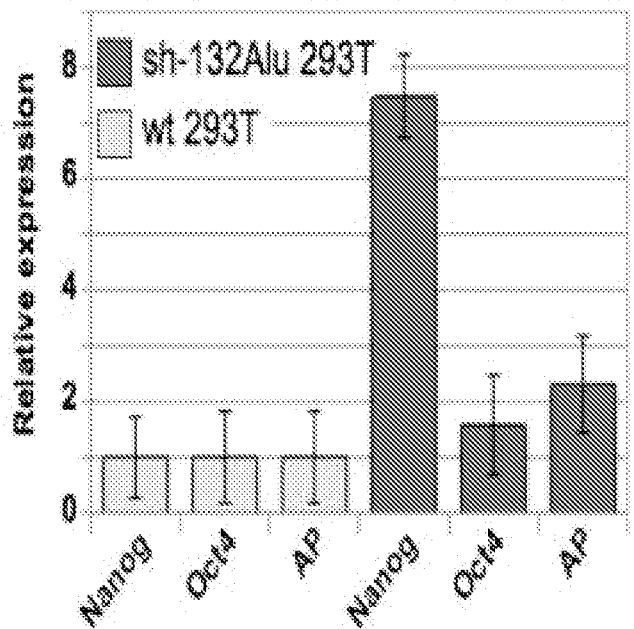
Figure 20D:
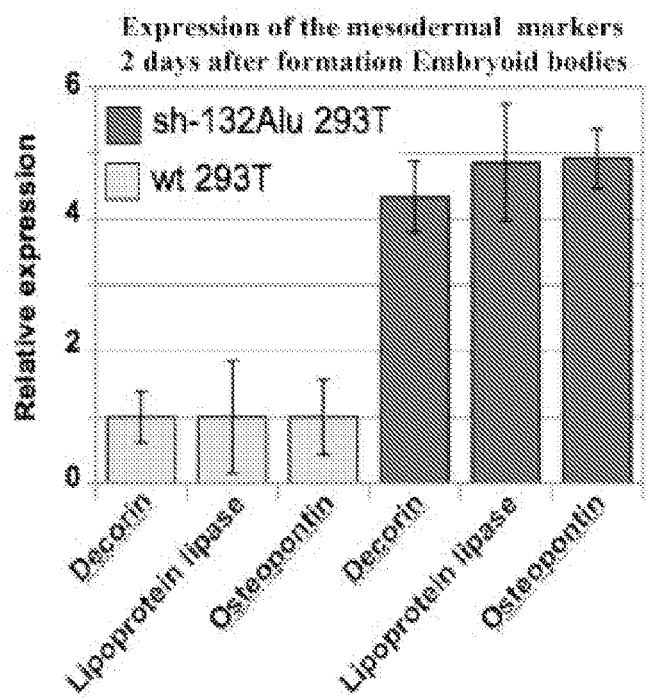
Figure 20E:
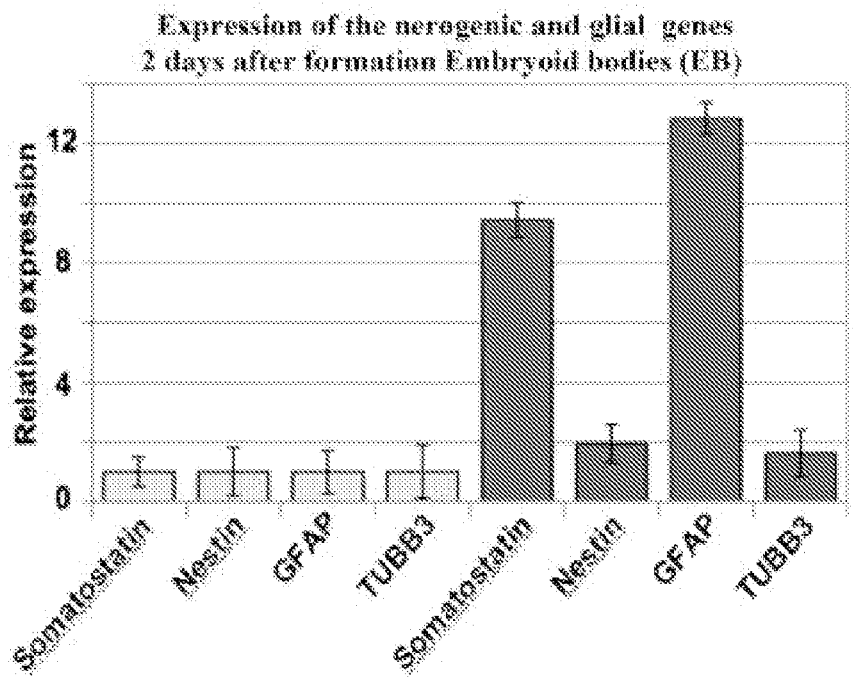

It has been proposed that transcriptional control through retroelements may facilitate pericentric transcription (Ugarkovic (2005) *EMBO Rep.*, 6: 1035-1039). The large clusters of γH2AX chromatin in our experiments colocalized with pericentric regions known to be enriched for SINE/Alu retrotransposal repeats (FIGS. 3B, 3D, 3E, Table 3, and Schueler and Sullivan (2006) *Annu. Rev. Genomics Hum. Genet.*, 7: 301-313). Considering that transcriptional activity of SINE/Alu repeats was largely upregulated in SEN hADSCs (FIG. 14) and driven by the Pol-III transcriptional complex (Deininger (1989) *Mobile DNA* (Washington, D.C., American Society for Microbiology)), we examined the dynamic formation of the persistent 53BP1/γH2AX foci and FUr-incorporation in response to the inhibition of Pol-III transcription by the drug tagetin (Allen et al. (2004) *Nat. Struct. Mol. Biol.*, 11: 816-821; Wang et al. (2003) *Mol. Biol. Cell*, 14: 2425-2435).

Senescent hADSCs were either cultured in the presence of 10 tM inhibitor of Pol III transcriptional activity, tagetin, for 2 hrs at 37° C. (+tagetin) or in the absence of the inhibitor treatment (-tagetin). Nuclear RNA was labeled by addition of 2 mM FUr to the culture for 10 min at 37° C. After fixation, cells were immunolabelled with anti-BrdU antibody (red) to detect FUr incorporation sites in combination with anti-53BP1. Double labeling experiment revealed FUr incorporation sites exclusively localized with persistent DNA damage sites throughout entire depth of z-stack images. Tagetin inhibition of Pol III dependent transcription resulted in complete disappearance of FUr incorporation, and loss of compaction of the DNA damage sites as detected by more defuse 53BP1 staining.

Figure 5:
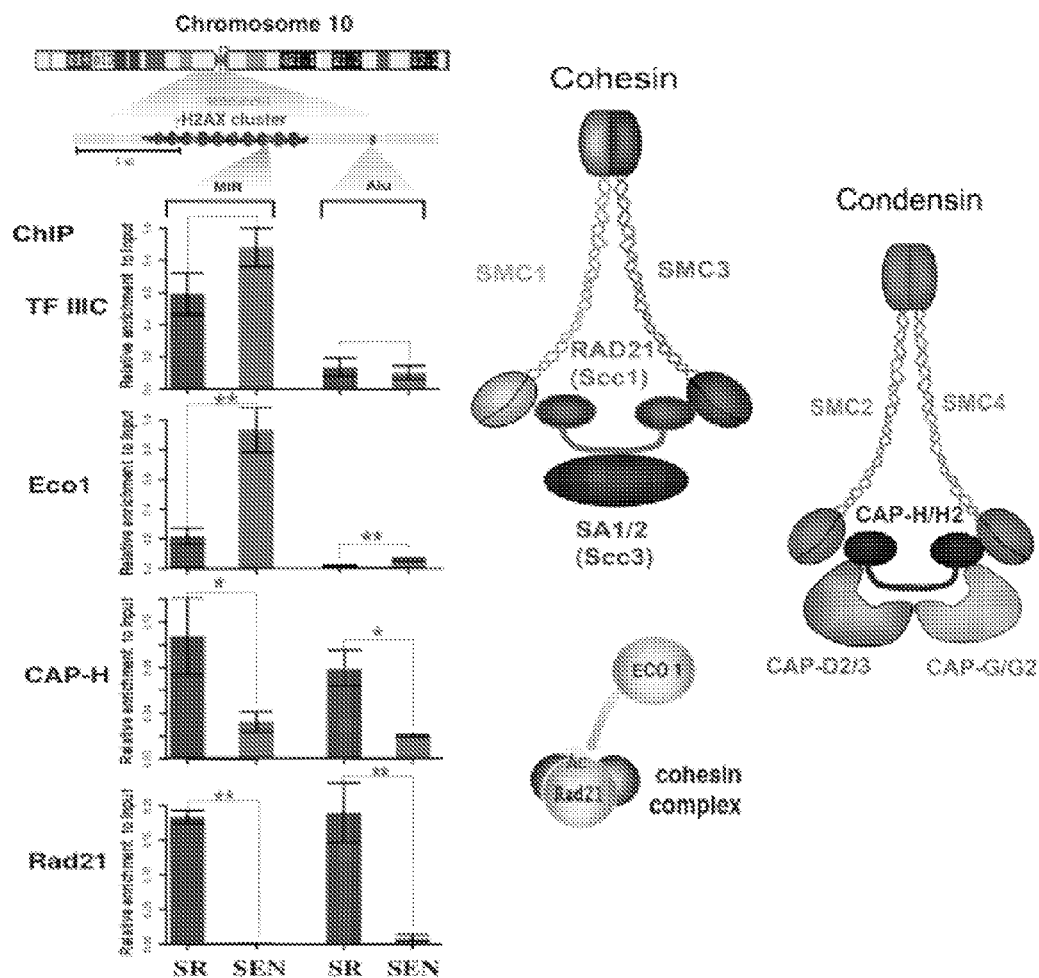
FIG. 5 shows that centromere-associated persistent DNA damage in senescent hADSCs correlates with transcriptional up-regulation of SINE/Alu retrotransposons and defects in recruitment of cohesin and condensin I complexes. C) Loss of cohesin and condensin I in the peri-centric location of persistent DNA damage in senescent hADSC. ChIP analysis of the peri-centric repeats on chromosome 10 in self-renewing (blue bars) and senescent (red bars) hADSCs. Repeats were assessed as locations for recruitment of TFIIIC, Eco1 as well as components of cohesin (Rad21) and condensin I (CAP-H) complexes (n=3, ±SEM). Schematic representation of the subunits of the cohesin and condensin I complexes, as well as a cartoon of previously reported function of Eco1, are shown. *p<0.02, **p<0.2.

Our data revealed that SEN hADSCs treated with the inhibitor of Pol-III tagetin showed impaired 53BP1 focus-forming capacity. Further, comparative strand-specific RT-PCR analysis of a number of SINE/Alu sequences associated with DNA damage in pericentric areas of chromosomes 10 (designated MIR and Alu) and 21 (designated AluSx and AluJb) revealed that upregulation of Alu transcriptional activity correlates with the presence of persistent DNA damage in SEN samples, as shown for the Alu repeat in the vicinity of the 7.6 kb γH2AX cluster. Our data demonstrate that, despite the fact that the transcriptional activity of the chosen repeats (AluJb, AluSx, and Alu) is recorded regardless of the state of the hADSC. Alu transcription is upregulated on chromosome 10 where damage is observed only upon cellular senescence. No transcriptional activity from the MIR element was recorded in either the SR or SEN state of hADSCs. These data also support our observation that γH2AX/53PB1 foci in SEN hADSC are centers of Pol-III dependent transcriptional activity (FIG. 4C). To our surprise, by using a conventional ChIP assay, we observed an increase in the recruitment of a Pol-III transcriptional complex (designated TFIIIC) to the MIR repeat during senescence even in the absence of the MIR-recorded transcription (FIG. 5). This could be due to an ability of TFIIIC to not only be essential for loading Pol-III machinery (Young et al. (1991) *Science*, 252: 542-546; Kundu et al. (1999) *Mol. Cell. Biol.*, 19: 1605-1615; Noma et al. (2006) *Cell*, 125: 859-872), but also for its ability to participate in the structural organization of chromatin cohesion and condensation within the eukaryotic nucleus as recently demonstrated in yeast (Iwasaki et al. (2010) *Mol. Biol. Cell*, 21: 254-265).

The presence of large tracts of satellite DNA limits the selection of strand-specific primers for reverse transcription due to a higher degree of sequence complementation, thus preventing further meticulous assessment of multiple, densely-packed SINE/Alu repeats within and near these genomic loci. Nevertheless, our data, together with multiple reports from yeast and mammals (Lunyak et al. (2007) *Science*, 317: 248-251; Noma et al. (2006) *Cell*, 125: 859-872; Oki and Kamakaka (2005) *Mol. Cell*, 19: 707-716; Scott et al. (2006) *Curr. Biol.*, 16: 119-129; Willoughby et al. (2000) *J. Biol. Chem.*, 275: 759-768), suggest a general role for the Pol-III transcription in genome organization, and support the hypothesis that, similar to centromeric tRNA genes in yeast (Iwasaki et al. (2010) *Mol. Biol. Cell*, 21: 254-265), pericentric SINE/Alu retrotransposons in humans may be integral to centromere functioning in self-renewing hADSCs, and upon senescence of hADSCs.

Impaired Cohesin and Condensin I Association with Pericentric γH2AX Foci in Senescent hADSCs Multiple lines of evidence indicate that the processes of chromosome repair and segregation are directly linked through cohesin, an evolutionarily-conserved protein complex (Heidinger-Pauli et al. (2008) *Mol. Cell*, 31: 47-56; Kim et al. (2002) *Proc. Natl. Acad. Sci. USA*, 99: 1241-1246; Sjogren and Nasmyth (2001) *Curr. Biol.*, 11: 991-995; Strom et al. (2004) *Mol. Cell*, 16: 1003-1015; Unal et al. (2004) *Mol. Cell*, 16: 991-1002). Specific association of cohesin with SINE/Alu repeats was also previously reported (Hakimi et al. (2002) *Nature*, 418L 994-998). The Scc1/Rad21/Mcd1 subunit of this complex is central to cohesin function and has been shown to be necessary for sister chromatid cohesion and kinetochore function in vertebrate cells (Sonoda et al. (2001) *Dev. Cell*, 1: 759-770), as well as G1 and G2-M DNA damage checkpoints (Jessberger (2009) *EMBO J.*, 28: 2491-2493). Reportedly, the cohesin complex becomes enriched at DSB sites and facilitates DNA repair by homologous recombination (HR) (Bekker-Jensen et al. (2006) *J. Cell Biol.*, 173: 195-206; Potts et al. (2006) *EMBO J.*, 25: 3377-3388). Inefficient postreplicative repair of DSB can arise from a deficiency in either cohesin loading or the conversion of cohesin to its cohesive state by Eco1 (ctf7) (Strom et al. (2004) *Mol. Cell*, 16: 1003-1015; Unal et al. (2004) *Mol. Cell*, 16: 991-1002; Unal et al. (2007) *Science*, 317: 245-248). In addition, one cannot overlook the importance of the condensin-related pathway in these events. Condensin loads cohesin onto the chromosome and is known to form two different complexes: condensin I and II (Samoshkin et al. (2009) *PLoS One*, 4: e6831). Importantly, the condensin I complex has been implicated in the function of pericentric heterochromatin. The depletion of the Cap-H subunit of the condensin I complex results in defects associated with alterations in the structural integrity of centromere-proximal heterochromatin in *Drosophila* (Oliveira et al. (2005) *Mol. Cell. Biol.*, 25: 8971-8984). It has been demonstrated that Cap-H depletion does not affect CENP-A incorporation into the centric chromatin or kinetochore assembly, but does result in severe depletion of cohesin Scc1/Rad21/Mcd1, triggering cell cycle defects.

We hypothesized that SINE/Alu transcription in pericentric chromatin can affect condensin and cohesin loading, thus blocking DNA repair by HR. This inability to repair DNA damage will directly or indirectly result in the cessation of the SR capacity of hADSCs by triggering cellular senescence. Therefore, we investigated the recruitment components of the cohesin complex Scc1/Rad21/Mcd1, condensin I complex (Cap-H), and histone acetylase Eco1 to the SINE/Alu repeats in the vicinity of a persistent pericentric γH2AX cluster on chromosome 10. Data obtained by conventional ChIP analysis demonstrated a statistically significant loss in the recruitment of Scc1/Rad21/Mcd1 and Cap-H to the MIR and Alu repeats during senescence of hADSCs (SEN red bars in FIG. 5C) when compared to the status of the same genomic locations in SR cells (SR blue bar in FIG. 5C). Surprisingly, the recruitment of histone acetylase Eco1 was largely correlated with the formation of persistent γH2AX clusters in senescence, and appeared to be Scc1/Rad21/Mcd1-independent. This suggests another, not yet identified, role for the Eco1 protein in DDR, different from its previously reported participation in the modulation of cohesiveness of Scc1/Rad21/Mcd1 (Hakimi et al. (2002) *Nature*, 418L 994-998; Strom et al. (2004) *Mol. Cell*, 16: 1003-1015; Unal et al. (2004) *Mol. Cell*, 16: 991-1002; Unal et al. (2007) *Science*, 317: 245-248).

Together these data further support the correlation between an increase in SINE/Alu transcription, and, (i) DNA damage accumulation, (ii) defects in pericentric recruitments of condensin I (Cap-H) and cohesin (Scc1/Rad21/Mcd1), and (iii) senescence of hADSCs.

Functional Significance of the SINE/Alu Transcripts in Senescence of hADSCs

Figure 6A:
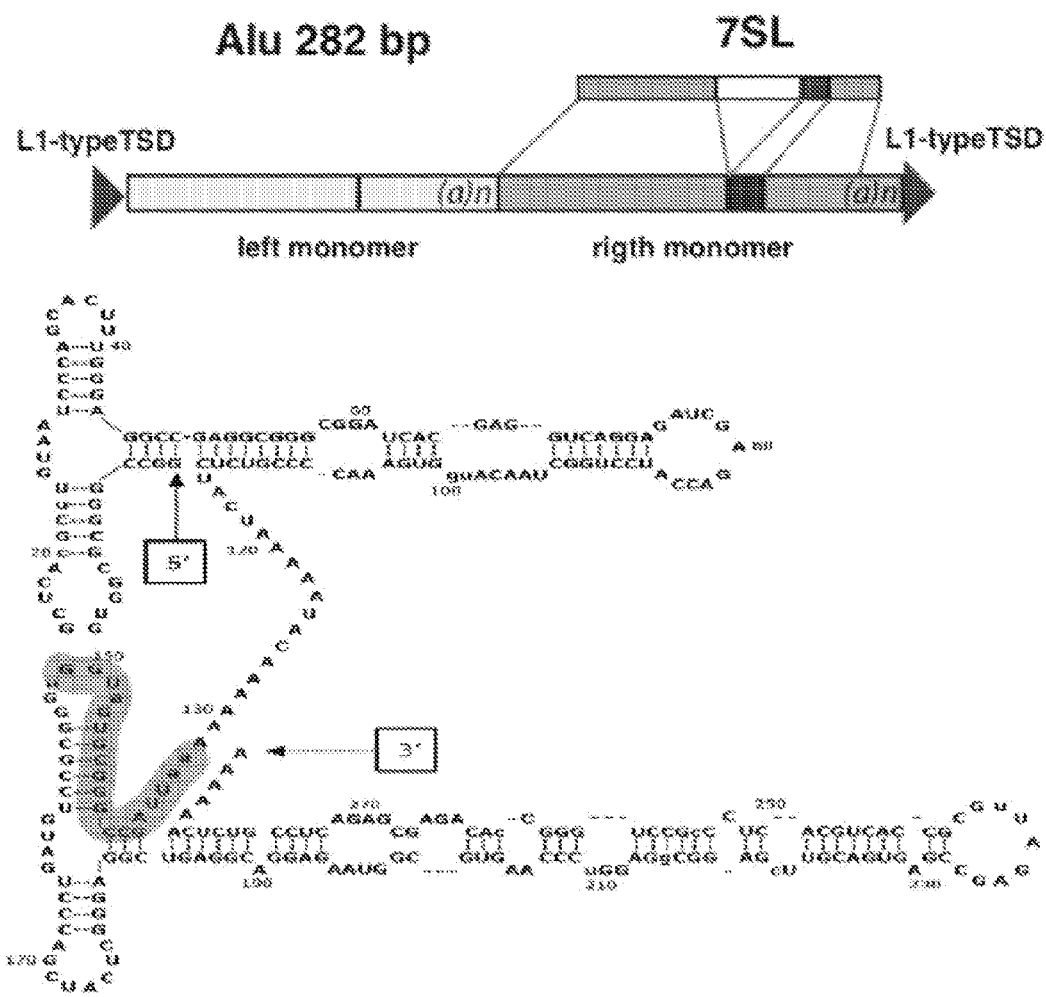
FIGS. 6A-6G illustrate that stable knockdown of generic SINE/Alu transcript in senescent human adult stem cells restores cell's proliferative properties and produces iPS-like phenotype.
Figure 6B:
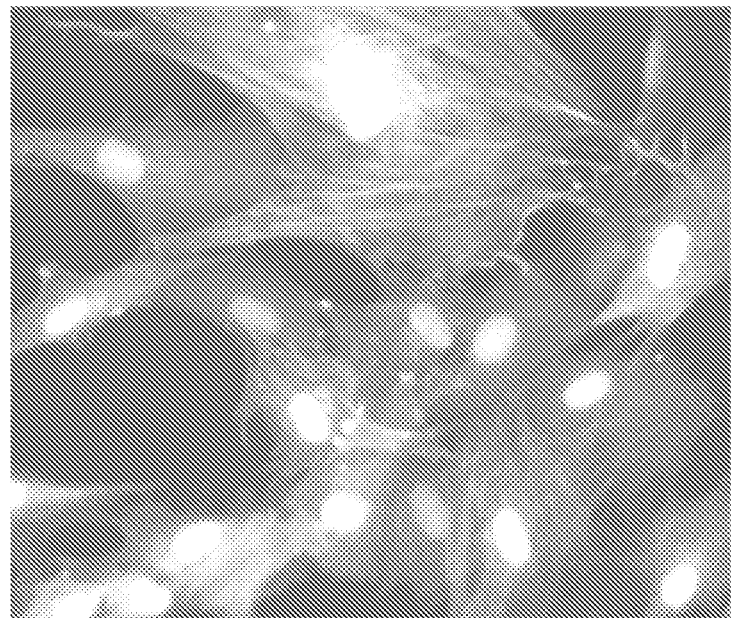

SINE/Alu elements occupy 6% of the human genome, significantly outnumbering other families of pseudogenes generated by retrotransposition (Weiner et al., 1986). The human SINE/Alu retrotransposon is a tandem repeat of two B1 elements connected by an A-rich linker (FIG. 6A), and the secondary structure of its RNA was previously reported (Sinnett et al. (1991) *J. Biol. Chem.*, 266: 8675-8678). In order to evaluate the functional significance of SINE/Alu transcription in establishing and/or mediating cellular senescence upon ex-vivo aging, SEN hADSCs were genetically manipulated to stably express shRNA, targeting the generic SINE/Alu transcript. We took advantage of the common sequence feature of SINE/Alu retrotransposons to generate a number of lenti-virus-delivered shRNA constructs carrying GFP for assessment of transduction efficiency (FIG. 6B; Experimental Procedures).

Figure 6C:
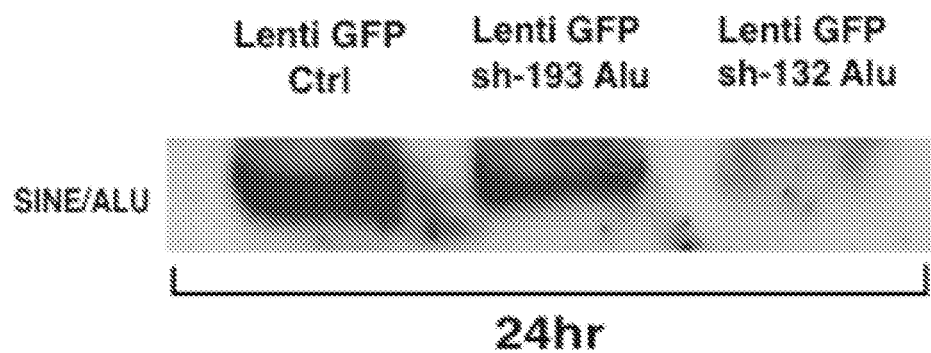
Figure 6D:
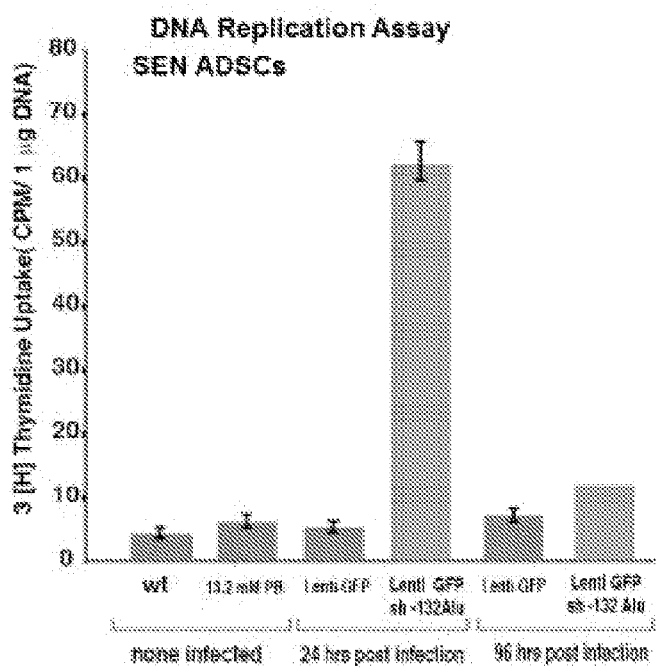
Figure 6E:
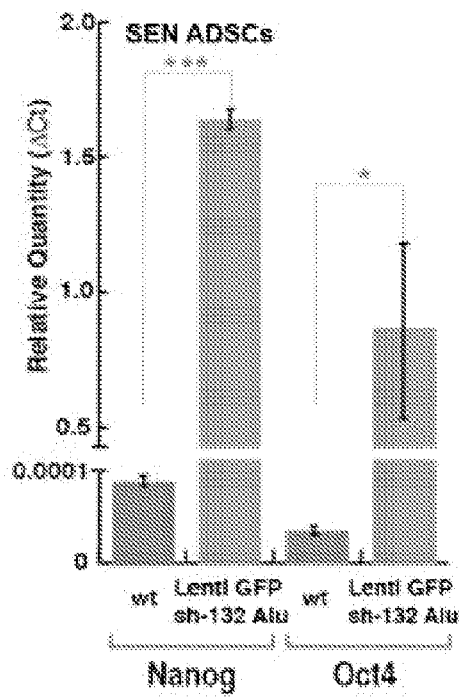

Knockdown of the generic SINE/Alu transcript in transduced hADSCs stably expressing shRNA against different portions of SINE/Alu was demonstrated by Northern Blot hybridization (FIG. 6C) with a transduction efficiency of nearly 99% (FIG. 6B). hADSCs transduced with lentiGFP expressing sh-132Alu RNA demonstrated a near complete knockdown of the generic SINE/Alu transcript. hADSCs transduced with lentiGFP (control) or lentiGFP sh-193Alu exhibited little or no change at the SINE/Alu transcription level. Surprisingly, SEN hADSCs lines stably expressing sh-132Alu RNA had a dramatically altered morphology and exhibited an increase in proliferation as detected in $^3$[H] thymidine uptake DNA synthesis experiments (FIG. 6D). In contrast, SEN hADSCs transduced with lentiGFP (control), or treated with polybrene alone (PB), did not show any significant changes in their proliferation rate when compared with wild type (wt) SEN hADSCs (FIG. 6D). Faithful re-establishment of DNA synthesis upon knockdown of the SINE/Alu transcript was further recorded 96 hours after transduction. Unexpectedly, when compared to wt SEN hADSCs, prior SEN hADSCs lines stably expressing sh-132Alu RNA demonstrated statistically significant upregulation of pluripotency factors Nanog and Oct4 as detected by qPCR analysis (FIG. 6E). The levels of Nanog and Oct4 in wt SEN hADSCs were below the threshold of the qPCR method.

Figure 6F:
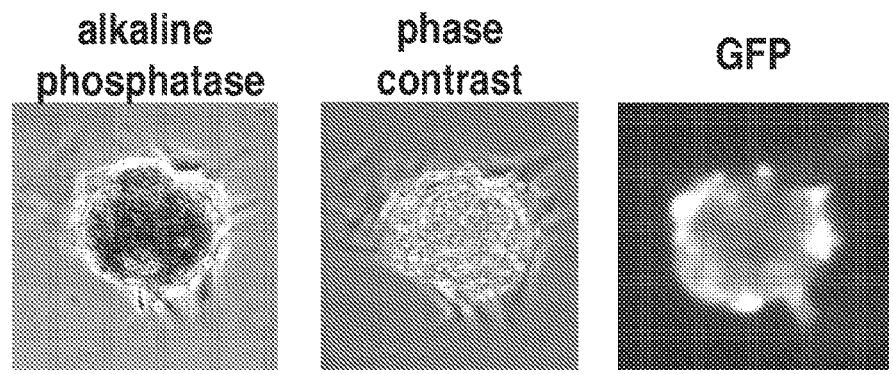

In summary, this finding raises the possibility that SINE/Alu RNA serves as an unexpected but key component of the machinery that controls stem cell pluripotency. Consistently, we observed that prior SEN hADSC with stable knockdown for generic SINE/Alu RNA were viable, and after 7 days in culture had formed cell aggregates (embryoid-like structures) which tested positive for alkaline phosphatase activity, a marker of induced pluripotency (FIG. 6F).

Discussion

Repetitive elements are implicated in changing/controlling properties of the chromatin in many systems, but few studies have addressed their functional significance in the context of cellular aging, in particular, in human adult stem cells. Several observations have linked persistent DDR to the manifestation of cellular senescence phenotype and ultimately to cell aging. Although cellular senescence is thought to be naturally irreversible cell-cycle arrest induced by DDR signaling, it is still unclear what determines the inability of cells with activated DDR to promptly and properly fix DNA lesions and restore their proliferative capacity. However, what has become clear from the cumulative studies of different models of cellular senescence is that these determinants can vary among cell types and in intensity, duration and nature of the DNA damage.

This raises the possibility that specific genomic regions/elements exist within cells where DNA damage is less easily repaired, possibly in a manner which is affected by age-dependent changes in chromatin structure and/or chromosomal organization. These functional elements have not been previously identified. In this study we have addressed this question.

Figure 6G:
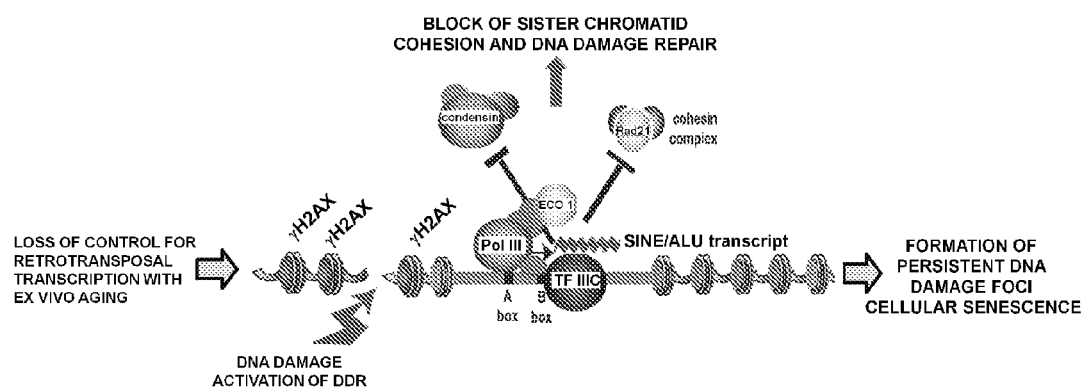

Central to this working hypothesis was our initial effort to perform a location analysis of γH2AX histone modification, which appears on the nucleosomes adjacent to the sites of DNA lesions. By using ChIP-seq analysis with single nucleosome resolution we were able to map locations of repairable DNA damage, which did not affect the proliferative capacity of hADSCs, and perform a comparative analysis of the dynamic of this damage in the onset of cellular senescence. Based on the distribution of γH2AX modifications, our data allowed us to conclude that neither repairable nor persistent DNA damage occurs randomly in SR or SEN hADSCs, and both types of damage are biased toward the transposable portion of the genome. Increased transcriptional activity of SINE/Alu retrotransposons in the aging human adult stem cells significantly correlates with the formation of persistent DNA damage foci, indicating a role in interfering with DNA repair. We provide a mechanistic explanation for retrotransposons' transcriptional interference with DDR: defective recruitment of the cohesin and condensin I complexes to pericentric chromatin upon their activation. Both of these complexes are critical to chromatin organization and damage repair of these genomic regions. We propose a novel model whereby SINE/Alu transposons act by altering chromatin structure in the vicinity of DNA lesions, thus blocking their repair (FIG. 6G). This event is integral to establishing/mediating persistent DDR upon ex-vivo aging of human adult stem cells.

Although it is still an open question what regulates a transcriptional activity of SINE/Alu retrotransposons, it is tempting to speculate that this might be due to the loss of epigenetic control for DNA methylation with ex-vivo aging of hADSCs. However, we cannot exclude the possibility that upregulation of the SINE/Alu transcripts is not directly related to an increase in their transcriptional activity, but rather results from senescence-associated deficiencies in their posttranscriptional processing, turn over or even degradation. Whatever their nature, our finding represents the first example of SINE/Alu transcription's role in the altering the properties of pericentric chromatin in conjunction with persistent DDR and cellular senescence of human adult stem cells.

Importantly, our results demonstrate a functional significance of SINE/Alu transcripts in the mechanism of ex-vivo aging of hADSC, and challenge the dogma that cellular senescence, and ultimately cellular aging, is an irreversible process. Since a depletion of generic SINE/Alu transcripts alone is sufficient to reinstate the proliferative capacity of hADSCs, and to increase the plasticity of previously niche-restricted human adult stem cells, it is plausible to suggest that SINE/Alu retrotransposons are playing an important role in mesenchymal niche specification through yet unknown, but interconnected with adult stem cell aging, pathways.

Experimental Procedures

Antibodies

Primary antibodies used were: b-actin (Abcam #ab62760), 53BP1 (Bethyl Laboratories #A300-273A), BrdU (BD, 7580), CAP-H (Bethyl Laboratories #A300-603A), CD31 (Invitrogen #HMCD3101), CD44 (Invitrogen #HMCD4401), CD45 (Invitrogen #HMCD4501), CD105 (Invitrogen #HMCD10520), Phospho-cdc2 (Tyr15) (Cell Signaling Technologies #9111), Phospho-Chk1 (Ser345) (CST #2341), Phospho-Chk2 (Thr68) (CST #2661), CENP-A (Abcam #ab13939), human anti-centromeric autoantibody, a-CREST (Antibodies Incorporated #15-235), Eco1 (Bethyl Laboratories #A300-312A), γH2AX (Millipore #05-636), PML (Santa Cruz Biotechnology #sc-966), and Rad21 (Abcam #ab992). Secondary antibodies were AlexaFlour® conjugated donkey antibodies (Invitrogen).

Human ADSC Isolation and Expansion

Human adipose derived stem cells were isolated from human subcutaneous white adipose tissue collected during liposuction procedures. The lipoaspirate was suspended in Hank s Buffered Salt Solution (HBSS), 3.5% Bovine Serum Albumin (BSA), 1% Collagenase, type II (Sigma) in 1:3 w/v ratio and shaken at 37° C. for 50 min The cells were filtered through a 70 µm mesh cell strainer (BD Falcon #352350), treated with Red Blood Cell Lysis buffer (150 mM $NH_4Cl$, 10 mM $KHCO_3$, 0.1 mM EDTA, pH 7.3), and expanded ex-vivo in DMEM/F12 complete medium (DMEM/F12, 10% FBS, 100 U/ml penicillin, 100 µg/ml streptomycin, 2.5 µg/ml amphotericin B; Invitrogen) in 10% CO2 at 37° C. and passaged at 80% confluency, changing medium every 72-96 hours. Cumulative population doublings were calculated by summing the population doublings (PD=log(N/

$N_0$)×3.33, where $N_0$ is the number of cells plated in the flask and N is the number of cells harvested at this passage) across multiple passages as a function of the number of days it was grown in culture.

Surface Marker Characterization $5×10^5$ cells each were incubated for 30 min on ice in the dark with fluorochrome-conjugated antibodies (CD31, CD44, CD45 and CD105; Invitrogen) in PBS with 1% BSA (Sigma), washed and analyzed in a Guava EasyCyte Mini System (Guava Technologies, Millipore). Data analysis was done with FlowJo software (Tree Star, Ashland, Oreg.).

Assessment of Cellular Senescence and Pluripotency Phenotype

Senescence-associated β-galactosidase activity assay was done as described in manufacturer's kit (BioVision). Cellular phenotype towards induced pluripotent cells was assayed with alkaline phosphatase staining kit (Stemgent).

Immunofluorescence $1-3×10^4$ cells/well in 4-well slides were fixed with 4% paraformaldehyde and permeabilized with PBS, 0.5% Triton X-100. The blocking and antibody incubations were carried out in 4% normal donkey serum (NDS; Jackson Immunochemicals) in PBS. The nuclei were counter-stained with 100 ng/ml 4',6-diamidino-2-phenylindole (DAPI; Sigma), and the slides were mounted in ProLong® Gold antifade aqueous mounting medium (Invitrogen).

Epifluorescence images were acquired on an Olympus BX60 fluorescence microscope with Spotfire 3.2.4 software (Diagnostics Instruments). Confocal images (z-series slice thickness 0.39 μm) were acquired on Zeiss LSM 510 NLO with 488 nm Argon, 543 nm HeNe, and Coherent Chameleon 2-photon lasers using a 63× planapo objective and 0.08×0.08×0.39 μm voxel dimensions. Image stacks were deconvolved using Huygens Professional 3.4.0 (Scientific Volume Imaging, Netherlands) and visualized in Bitplane Imaris 6.3.1 (Bitplane Inc., Saint Paul, Minn.).

5-Fluorouridine Labeling for RNA Transcript Detection In Situ

Senescent hADSCs, $1×10^4$ cells/well in 4-well slides, were treated with 2 mM 5-Fluorouridine (FUr; Sigma) for 10 minutes. The nuclei were exposed with ice-cold CSK buffer (100 mM KCl, 300 mM sucrose, 10 mM Pipes pH 6.8, 3 mM MgCl2, 1 mM EGTA, 1.2 mM phenylmethylsulfonyl fluoride) with 0.5% Triton X-100 and fixed with 4% paraformaldehyde. Immunostaining was performed as described above for immunoflourescence.

Expression Profiling

Total RNAs from ~$1.5×10^6$ SR and SEN ADSCs were prepared by TRIZOL® method (Invitrogen). Human Cell Cycle qRCR Array (SABiosciences #PAHS-020C-2) was used for the profiling (7500 Fast PCR System, Applied Biosystems). Three RNA samples from SR hADSCs were matched to RNA samples for their replicatively SEN counterparts. Statistical significance of the transcriptional differences was calculated by T-test as described in SABiosciences manual and "www.sabiosciences.com/RTPCR". The model-based expression values were calculated and filtered for the genes with higher or lower than two-fold differences in expression between SEN and SR samples. Categories of the genes were annotated using the PANTHER (protein analysis through evolutionary relationships) classification system.

Preparation of Nucleosomal Lysates $3×10^5$ SR and SEN hADSCs were washed with PBS, and crosslinked in 1% formaldehyde. The cells were scraped from the plate in CSK buffer with 0.5% Triton X-100, washed, and sonicated in microccocal nuclease buffer (50 mM Tris-HCl, pH 7.9, 5 mM CaCl; NEB) with a Covaris S2 Sonicator (frequency sweep at 1% duty cycle, 5 intensity and 50 cycles per burst for 12 cycles of 10 sec each at 4° C.). Sonicates were cenrtrifuged to get rid of the cellular debris, and supernatants were incubated with 25U/tl of microccocal nuclease (NEB).

ChIP-Seq: Nucleosomal ChIP and SOLiD Library Preparation

Nucleosomal lysates were adjusted to antibody Binding buffer (25 mM Tris-HCl pH 7.9, 0.15% SDS, 1% Triton X-100, 150 mM NaCl), and immunoprecipitated with 10 μg γH2AX antibody overnight at 4° C. Protein A Sepharosebeads were blocked with 10 μg/ml glycogen, 10 μg/ml lysozyme, 5 μg/mltRNA and 20 μg/ml BSA for 1 hour at 4° C. before binding to the immuno-complexes for 1 hour at 4° C. Beads were washed with Binding buffer and again with the same buffer containing 0.5M NaCl and finally in TE (10 mM Tris-HCl pH 7.6, 1 mM EDTA). Immuno-complexes bound to beads were re-suspended in TE buffer, de-crosslinked, and purified by Proteinase K treatment, phenol:chloroform extraction, and isopropanol precipitation. DNA fragments were prepared for adapter ligation by filling-in ends by DNA polymerase I (Klenow fragment) and phosphorylating 5' ends of PCR primers by Polynucleotide kinase (NEB), and ligated to 30-fold molar excess of SOLID™ System 2.0 (Applied Biosystems) library adapters according to manufacturer's protocol. DNA libraries were amplified by PCR using cloned Pfu DNA Polymerase (Stratagene, Agilent Technologies. Mononucleosomal size DNA fragments were size-selected in a 2% agarose gel, cut around 200 bp size, and purified with QIAQUICK® Gel Extraction Kit (Qiagen). Emulsion PCR (ePCR) for sequencing bead preparations were done with 0.05 and 0.1 pg/μl of library DNA for each sample. Samples were sequenced on SOLiD™ System 2.0 (Applied Biosystems) according to manufacturer's protocol.

RT PCR Analysis of Retrotransposal Transcription and qPCR

Genomic coordinates of the SINE/Alu elements tested in RT-PCR were from the March 2006 Assembly (NCBI36/hg18) of the Human Genome Browser at UCSC (genome.ucsc.edu); MIR: chr10:41922815-41922906, Alu: chr10:41928992-41929118, AluJb: chr21:10141132-10141429 and AluSx: chr21:10145344-10145644. 100 ng of total RNA was used with the RT2 First Strand Kit (SABiosciences) per reaction. The primers for first strand synthesis are at locations outside of the SINE/Alu element sequences (external or reverse primers, Table 9) and forward primers within the SINE/Alu element sequence (internal forward primers, Table 9). RPL13A, GAPDH was used as a positive control.

For real-time quantitative PCR, 1 mg of each total RNA was used for first strand cDNA synthesis with SUPERSCRIPT® III First-Strand Synthesis System for RT-PCR (Invitrogen) with random priming. qPCR was performed using RT2 SYBR Green qPCR MasterMix (SABiosciences) and run in LIGHTCYCLER® 480 II (Roche). qPCR primers are listed in Table 9. Data analysis of relative gene expression was done by 2-DCt method.

Lentiviral shRNA Constructs

Lentiviral shRNA constructs to knockdown genetic SINE/Alu transcript were designed as follows: oligonucleotides Lenti sh-132 Alu RNA: 5'-GAT CCC CCC ACC ACG CCC GGC TAA TTT TCA AGA GAA ATT AGC CGG GCG TGG TGG TTT TTG GAA A-3' (SEQ ID NO:10) and Lenti sh-193 Alu RNA 5'-GAT CCC CCC CGG GTT CAA GCG ATT CTT TCA AGA GAA GAA TCG CTT GAA CCC GGG TTT TTG GAA A-3' (SEQ ID NO:11), were annealed with equal amounts of their complementary strands, creating restriction site specific overhangs for cloning, and ligated into HindIII and BglII digested, gel purified pENTR/pTER+ vector (Campeau et al., 2009). The constructs were confirmed by sequencing (sense strand sequence is shown above). Equal amounts of each constructs was mixed with pLenti-CMV-GFP DEST vector (Campeau et al., 2009) in LR Clonase reaction to recombine cloned shRNA production elements into a destination vector according to manufacturer's instructions (Invitrogen). The produced lentiviral plasmid was transformed into E. coli Stb13 cells (Invitrogen) for amplification.

Lentiviral Production and Transduction 293T cells were grown in DMEM complete medium (DMEM, high glucose, 10% FBS, 0.1M nonessential amino acid, 6 mM L-glutamine, 1 mM pyruvate, 100 U/ml penicillin, 100 µg/ml streptomycin) for lentiviral production, and transfected for 12 hours with pLenti sh-132Alu or pLenti sh-193Alu and pCgpV, pRSV-Rev, and pCMV-VSV-G helper plasmids (Allele Biotechnology) in 2:1:1:1 molar ratio using Lipofectamine 2000 (Invitrogen) according to standard protocol (Campeau et al., 2009). Medium was collected at 48 and 72 hours and filtered (0.45 µm). Virus was precipitated with PEG and frozen in aliquots (−80° C.). Lentiviral transductions were done in complete medium with 5 µg/ml Polybrene (Santa Cruz Biotechnology) for 12 hours. Viral titers were determined by comparing GFP positive cells counts to total population.

Proliferation Index

For each condition in $^3$[H]-thymidine uptake assay, 10,000 cells were treated with 1 µCi $^3$[H]-thymidine (Perkin-Elmer, Boston, Mass.) in DMEM/F12 complete for 24 hours. DNA was isolated from harvested cells and quantified with NanoDrop (ND-1000; NanoDrop Technologies Inc). $^3$[H]-thymidine uptake into cellular DNA was measured with liquid scintillation counter (LS 6500; Beckman Instruments). Lentiviral transduction was done as above, and untreated and Polybrene treated controls were carried out in parallel.

Northern Hybridization

RNA was isolated from SR and SEN hADSCs (with or without lentiviral transduction) with mirVANA (Ambion, Invitrogen) kit, and 2 mg of total RNA/lane was run on a 7M Urea, 6% polyacrylamide, TBE. Gel was stained with ethidium bromide, photographed and electroblotted onto Hybond™-N+(Amersham, GE Healthcare). Hybridizations were performed in 6×SSC, 4×Denhardts', 0.1% SDS at 37° C. Oligonucleotide probes were labeled with Biotin-16-dUTP (Roche) by terminal transferase (NEB). Northern was visualized with streptavidin-HRP (Invitrogen) using ECL Plus Western Blotting Detection Reagent (Amersham, GE Healthcare) and Amersham Hyperfilm (GE Healthcare). Oligonucleotide used as probes were: SINE/Alu 132:5'-CCA CCA CGC CCG GCT AAT TT-3' (SEQ ID NO:12) and SINE/Alu 90: 5'-CGC GCG CCA CCA CGC CCG GCT AAT TTT TGT ATT TTT AGT AGA GAC GGG GTT TCA CCA TGT TGG CC-3' (SEQ ID NO:13).

Example 2

Supplemental Methods

Outlier Removal.

γH2AX ChIP-seq tags were mapped to the March 2006 human genome reference sequence (NCBI build 36.1, UCSC hg18) using the SOLiD™ System Analysis Pipeline Tool (Corona Lite). After tag-to-genome mapping of the ChIP-Seq data for each biological replicate experiment, tag counts were compared between replicates for identical genomic positions across all chromosomes. To do this, tag counts for each individual nucleotide position in each replicate experiment were determined. Then nucleotide positions that have a tag count of 0 in either replicate were eliminated from consideration. This is because if a position has a tag count of 0 in both data sets, it will not be considered in the subsequent analysis since there is no signal there. In addition, if a position has a 0 tag count in one replicate and a nonzero tag count in the other replicate, then it is considered to be an unreliable position. For nucleotide positions that have non-zero tag counts in both replicates, linear regression was used to compare the tag counts over all nucleotide positions. Based on the regression line and the data distribution around the line, 95% confidence bounds are determined using the Working-Hotelling formula as follows: For each value of x, an expected value of y–E(y)—is estimated based on the linear regression model E(y)=mx+b. Then for each estimated value of E(y), a standard deviation– s(y)—is computed based on the data distribution around E(y) for the corresponding value of x. For each value of E(y), the upper and lower confidence values are computed as E(y)±w·s(y) where the constant w is determined based on the F distribution at the confidence level α with 2 and n−2 degrees of freedom: w=√(2·F[(1−α),2,n−2]). This regression analysis and confidence bound inference is done for each individual chromosome. Nucleotide positions that fall outside of the confidence bounds determined in this way are removed from further consideration. Replicate experiments were highly consistent.

Noise Reduction and Data Merging.

After removal of outliers, noise reduction was performed in order to empirically determine a tag count threshold value th above which an individual nucleosome sized genomic position (i.e. mono-nucleosome) is considered to be modified. A window size of 200 bp was chosen for this analysis based on 147 bp of DNA in a single nucleosome plus linker sequence. The average tag count in 200 bp windows— $\lambda_{200}$—is computed as the total number of tags in the genome n divided by the genome length l times the window size of 200: $\lambda_{200}=(n/l)\cdot 200$. The Poisson distribution is parameterized by the 200 value in order to model the background noise and determine the tag count signal threshold th for modified nucleosome positions:

$$th = \min\left\{\tau: \sum_{i=\tau}^{\infty} \frac{\lambda^i}{i!} e^{-\lambda} \leq P\right\}$$

where τ=the number of tags in a window and P is a Bonferroni corrected P-value threshold. To do this, corresponding position-specific tag count values were summed between replicate experiments and compared to a Poisson distribution parameterized by the sum of the 200-values computed for each replicate. This approach was taken because the replicates are independent biological replicates, each of which is modeled by a separate Poisson distribution. Therefore, the summation of position-specific tag counts across the genome can also be modeled by a Poisson distribution with a parameter equal to the sum of the individual 200-values from each replicate. This procedure resulted in a classification of all nucleosome size genomic positions as modified or unmodified based on data that has been merged between replicates and purged of outliers.

Maximal-Segment Based Clustering Algorithm for Continuous Modified Nucleosome Positions.

In addition to the analysis of mono-nucleosome size fragments of modified genomic DNA described previously, we also investigated clusters of adjacent co-located modified nucleosomes. Clusters were operationally defined as contiguous genomic regions where the number of modified mono-nucleosome size fragments is significantly greater than the average genomic background level of modified positions. To identify and demarcate such clusters, we applied the Maximal Segment algorithm. To do this, we first devised a binary scoring scheme that characterizes mono-nucleosome size fragments (200 bp) as either modified or unmodified. This procedure is used to define a binary genome-wide map of nucleosome scores. Then the Maximal Segment algorithm was applied to the genomic map of binary nucleosome scores to define clusters. The details of the Maximal Segment algorithm are presented elsewhere (Ruzzo and Tompa (1999) *Proc. Int. Conf Intell. Syst. Mol. Biol.*, 234-241). Below, we describe our scoring scheme for individual nucleosome positions.

Binary Nucleosome Scoring Scheme

A binary scoring scheme is implemented in such a way as to assign the log likelihood that an individual mono-nucleosome size fragment either modified or unmodified. The scores are assigned as: s=ln(q/p) where p is the density of modified nucleosome positions over the whole genome computed as the number of modified positions divided by the total number of positions and q is the density of modified nucleosome positions in real clusters. There is no way to directly calculate q since the clusters are unknown a priori. In order to estimate q, a Poisson distribution is parameterized with p, the density of modified nucleosome positions over the whole genome. Then, given a confidence level P, a threshold value of q can be chosen using the Poisson distribution as shown:

$$q = \min\left\{\tau: \sum_{i=\tau}^{\infty} \frac{\lambda^i}{i!} e^{-\lambda} \leq P\right\}$$

where τ=number of modified nucleosome positions.

This scoring scheme results in an assignment of a single positive score to all modified nucleosome positions and a single negative score to all unmodified positions. This approach is taken based on the proof that log likelihood ratios of this kind are optimal scores for the identification of contiguous genomic segments (Karlin and Altschul (1990) *Proc. Natl. Acad. Sci. USA*, 87: 2264-2268). In addition, the value of q chosen for the scoring scheme allows for control over cluster selection in the sense that the density of modified nucleosomes per cluster will be greater than or equal to the value of q.

Relative Entropy to Define Large Clusters.

After getting the size distributions of contiguous modified nucleosome regions (i.e. clusters), we classified the clusters into 3 groups: 1) mononucleosomal clusters, 2) mid-sized clusters and 3) large clusters. In order to set a size threshold between mid-sized and large clusters, we calculated the relative entropies for different thresholds between the size distributions in self-renewing and in senescent cells (FIG. 11A). The threshold is set as the one which gives the maximal relative entropy between the two distributions (FIG. 11C). Thus, the difference between fractions of mid-sized and large clusters in the two cell types is maximized.

Comparison with Genomic Features.

The tag-to-genome mapping and the quality control procedures described above (see Outlier removal and Noise reduction and data merging sections) yielded maps of nucleosome positions in the human genome that can be confidently considered to be modified by ãH2AX for self-renewing (SR) and senescent (SEN) hADSCs.

These maps were used to compare the locations of ãH2AX modified nucleosomes to various genomic features of interest within and between SR and SEN cells. For instance, we compared the locations of modified nucleosomes in the genome to the locations of transcription start sites, exons, introns, repetitive sequence elements, pericentric regions and peri-telomeric regions. These comparisons were done using the UCSC Table Browser tool (Karolchik et al. (2004) *Nucleic Acids Res.*, 32: D493-D496), which is a part of the UCSC Genome Browser suite of tools and genome annotations (Karolchik et al. (2003) *Nucleic Acids Res.*, 31: 51-54). In addition, custom Perl scripts were used to modify UCSC Genome Browser tracks, such as the gene annotation tracks, to pull out specific features of interest including transcription start site locations and exon/intron boundaries for further analysis.

TABLE 1

| Biological process | Gene name | Gene Symbol | Fold up-/down-regulation | P value |
| --- | --- | --- | --- | --- |
| cell cycle/cell cycle control | cyclin B1 | CCNB1 | −2.66 | 0.0006 |
| | cyclin B2 | CCNB2 | −3.10 | 0.0005 |
| | Cyclin D2 | CCND2 | 2.55 | 0.0001 |
| | cyclin F | CCNF | −2.40 | 0.008 |
| | cell division cycle 2, G1 to S and G2 to M | CDC2 | −4.51 | 0.0001 |
| | cell division cycle 20 homolog (*S. cerevisiae*) | CDC20 | −3.15 | 0.0001 |
| | cyclin-dependent kinase 2 | CDK2 | −2.75 | 0.0012 |
| | cyclin-dependent kinase inhibitor 3 (CDK2-associated dual specificity phosphatase) | CDKN3 | −3.28 | 0.0029 |
| | CHK1 checkpoint homolog (*S. pombe*) | CHEK1 | −3.00 | 0.008 |
| | retinoblastoma-like 1 (p107) | RBL1 | −2.56 | 0.0012 |

TABLE 1-continued

| Biological process | Gene name | Gene Symbol | Fold up-/down-regulation | P value |
|---|---|---|---|---|
| DNA replication | MCM2 minichromosome mantenacne deficient 2, mitotin (S. cerevisiae) | MCM2 | −3.29 | 0.0001 |
| | MCM3 minichromosome maintenance deficient 3 (S. cerevisiae) | MCM3 | −2.33 | 0.0184 |
| | MCM4 minichromosome maintenance deficient 4 (S. cerevisiae) | MCM4 | −3.44 | 0.0022 |
| | MCM5 minichromosome maintenance deficient 5, cell division cycle 46 (S. cerevisiae) | MCM5 | −3.57 | 0.0001 |
| | replication protein A3, 14 kDa | RPA3 | −2.52 | 0.0014 |
| | proliferating cell nuclear antigen | PCNA | −2.53 | 0.0009 |
| Chromosome segregation | MAD2 mitotic arrest deficient-like 1 (yeast) | MAD2L1 | −4.37 | 0.0021 |
| | kinetochore associated 1 | KNTC1 | −3.22 | 0.0049 |
| DNA repair | breast cancer 1, early onset | BRCA1 | −3.83 | 0.0032 |
| | breast cancer 2, early onset | BRCA2 | −3.32 | 0.0011 |
| | RAD51 homolog (RecA homolog, E. coli) (S. cerevisiae) | RAD51 | −3.75 | 0.0005 |
| mRNA transcription regulation | transcription factor Dp-1 | TFDP1 | −2.21 | 0.0097 |
| inhibition of apoptosis | baculoviral IAP repeat containing 5 (surviving) | BIRC5 | −3.70 | 0.002 |
| stress response | G-2 and S-phase expressed 1 | GTSE1 | −4.51 | 0.0017 |
| Biological process unclassified | CDC28 protein kinase regulatory subunit 1B | CKS1B | −2.35 | 0.0382 |
| | CDC28 protein kinase regulatory subunit 2 | CKS2 | −2.42 | 0.001 |
| | antigen identified by monoclonal antibody Ki-67 | MKI67 | −4.04 | 0.0053 |

TABLE 2

γH2AX ChIP-seq tag and mapping data.

| Experiment | Total tags | Mapped tags | % Mapped tags |
|---|---|---|---|
| SR1 | 25650863 | 6427476 | 25.058% |
| SR2 | 22864646 | 6740098 | 29.478% |
| SR3 | 23172888 | 7153067 | 30.868% |
| SR4 | 20554101 | 6610682 | 32.162% |
| SEN1 | 32114970 | 7915256 | 24.647% |
| SEN2 | 28469416 | 7569634 | 26.589% |
| SEN3 | 26694829 | 4911085 | 18.397% |
| SEN4 | 23942531 | 4780551 | 19.967% |

TABLE 3

Fractions of γH2AX clusters occupied by genomic features.

| Features | Mono-nucleosomal | | Mid-size | | Large | |
|---|---|---|---|---|---|---|
| | SR | SEN | SR | SEN | SR | SEN |
| Genic Regions | | | | | | |
| All genic regions | 41.5% | 41.0% | 42.9% | 39.7% | 47.9% | 35.2% |
| Promoter | 0.75% | 0.63% | 0.83% | 0.61% | 0.94% | 0.56% |
| Exon | 2.86% | 2.43% | 3.20% | 2.14% | 4.02% | 1.78% |
| Intron | 37.9% | 38.0% | 38.9% | 36.9% | 42.9% | 32.9% |
| Exon-intron Junction | 0.19% | 0.16% | 0.21% | 0.14% | 0.28% | 0.11% |
| Intergenic Regions | | | | | | |
| All Intergenic regions | 59.6% | 59.9% | 57.8% | 61.4% | 52.5% | 66.8% |
| All Transposable Elements (TEs) | | | | | | |
| All TEs | 72.7% | 70.6% | 69.6% | 70.2% | 64.4% | 65.6% |
| Retrotransposons | | | | | | |
| All Retro-transposons | 67.3% | 65.8% | 66.0% | 65.8% | 63.5% | 61.4% |

TABLE 3-continued

Fractions of γH2AX clusters occupied by genomic features.

| Features | Mono-nucleosomal SR | Mono-nucleosomal SEN | Mid-size SR | Mid-size SEN | Large SR | Large SEN |
|---|---|---|---|---|---|---|
| SINE Elements | | | | | | |
| All SINEs | 34.9% | 30.0% | 36.3% | 30.9% | 37.5% | 28.6% |
| Alu | 23.4% | 17.8% | 22.6% | 18.8% | 20.8% | 16.9% |
| MIR | 10.4% | 11.2% | 12.7% | 11.2% | 15.8% | 11.0% |
| SINE-other | 1.06% | 0.97% | 1.03% | 0.88% | 0.91% | 0.71% |
| LINE Elements | | | | | | |
| All LINEs | 32.4% | 35.8% | 29.7% | 34.9% | 26.0% | 32.8% |
| L1 | 20.3% | 23.6% | 17.2% | 22.8% | 12.9% | 21.9% |
| L2 | 10.7% | 10.5% | 10.9% | 10.4% | 11.5% | 9.19% |
| LINE-other | 1.42% | 1.68% | 1.55% | 1.65% | 1.64% | 1.75% |
| Other Transposable Elements | | | | | | |
| LTR | 20.8% | 17.7% | 18.6% | 17.1% | 14.9% | 15.9% |
| DNA | 8.50% | 9.15% | 8.75% | 9.35% | 8.70% | 8.57% |

TABLE 4

γH2AX tag density compared to chromosome gene density and GC content

| SR Slope | SR Correlation | SR P-value | SEN Slope | SEN Correlation | SEN P-value |
|---|---|---|---|---|---|
| Correlation: γH2AX tag density × chromosome gene density [$R_{\gamma H2AX|gene\ density}$] | | | | | |
| 0.48 | 0.64 | 5.2E−04 | −0.19 | −0.22 | 0.16 |
| Correlation: γH2AX tag density × chromosome GC content [$R_{\gamma H2AX|GC}$] | | | | | |
| 2366 | 0.67 | 2.6E−04 | 2429 | 0.54 | 3.9E−03 |
| Partial correlation: γH2AX tag density × chromosome gene density controlling for GC content [$r_{\gamma H2AX|gene\ density.GC}$] | | | | | |
| N/A | 0.49 | 0.01 | N/A | −0.65 | 1.1E−04 |

TABLE 5

Length fractions of genomic features intersected with clusters of γH2AX

| Features | Mono-nucleosomal SR | Mono-nucleosomal SEN | Mid-size SR | Mid-size SEN | Large SR | Large SEN |
|---|---|---|---|---|---|---|
| TSS | 0.51% | 0.43% | 2.29% | 1.36% | 1.12% | 0.20% |
| Exon | 0.64% | 0.55% | 2.90% | 1.56% | 1.58% | 0.21% |
| Intron | 0.46% | 0.46% | 1.91% | 1.45% | 0.91% | 0.21% |
| Junction | 0.63% | 0.53% | 2.81% | 1.48% | 1.60% | 0.19% |
| Intergenic | 0.67% | 0.68% | 2.65% | 2.26% | 1.04% | 0.40% |
| peri-centromere | 0.09% | 0.09% | 0.39% | 0.40% | 0.73% | 0.52% |
| peri-telomere | 0.31% | 0.21% | 1.42% | 0.75% | 0.29% | 0.26% |
| TE | 0.75% | 0.73% | 2.90% | 2.35% | 1.16% | 0.36% |
| intergenic TE | 0.76% | 0.74% | 2.88% | 2.43% | 1.04% | 0.39% |
| genic TE | 0.73% | 0.71% | 2.94% | 2.21% | 1.36% | 0.31% |
| Alu | 0.67% | 0.51% | 2.61% | 1.74% | 1.04% | 0.25% |
| MIR | 0.69% | 0.75% | 3.42% | 2.43% | 1.84% | 0.39% |
| SINE-other | 0.77% | 0.71% | 3.02% | 2.08% | 1.16% | 0.27% |
| L1 | 0.49% | 0.57% | 1.68% | 1.78% | 0.54% | 0.28% |
| L2 | 0.79% | 0.78% | 3.26% | 2.50% | 1.49% | 0.36% |
| LINE-other | 0.65% | 0.77% | 2.87% | 2.45% | 1.31% | 0.42% |
| LTR | 0.81% | 0.70% | 2.93% | 2.17% | 1.02% | 0.33% |
| DNA | 0.65% | 0.70% | 2.69% | 2.31% | 1.16% | 0.34% |

TABLE 6

List of genes with promoter γH2AX accumulation in SR or SEN cells.

| | | | |
|---|---|---|---|
| NM_001001933 | LHX8 | NM_152418 | WDR21C |
| NM_139240 | C1orf105 | NM_052832 | SLC26A7 |
| NM_015658 | NOC2L | NM_015435 | RNF19A |
| NM_198317 | KLHL17 | NM_030788 | TM7SF4 |
| NM_148902 | TNFRSF18 | NM_139166 | ABRA |
| NM_080875 | MIB2 | NM_177531 | PKHD1L1 |
| NM_033467 | MMEL1 | NM_021021 | SNTB1 |
| NM_152492 | CCDC27 | NM_078480 | PUF60 |
| NM_207370 | GPR153 | NM_201384 | PLEC1 |
| NM_181864 | ACOT7 | NM_024531 | GPR172A |
| NM_006786 | UTS2 | NM_003923 | FOXH1 |
| NM_005026 | PIK3CD | NM_001029976 | ZNF16 |
| NM_198544 | APITD1 | NR_023392 | ZNF252 |
| NM_001127325 | MAD2L2 | NM_021240 | DMRT3 |
| NM_001009611 | PRAMEF4 | NM_005511 | MLANA |
| NM_001018001 | KIAA1026 | NM_000170 | GLDC |
| NM_207348 | SLC25A34 | NM_144966 | FREM1 |
| NM_001089591 | UQCRHL | NM_017645 | FAM29A |
| NM_153213 | ARHGEF19 | NM_002172 | IFNA14 |
| NM_017940 | NBPF1 | NM_078487 | CDKN2B |
| NM_012387 | PADI4 | NM_016410 | CHMP5 |
| NM_014589 | PLA2G2E | NM_007343 | PRSS3 |
| NM_207334 | FAM43B | NM_015297 | KIAA1045 |
| NM_001113347 | ECE1 | NM_002732 | PRKACG |
| NM_002167 | ID3 | NM_001007470 | TRPM3 |
| NM_054016 | FUSIP1 | NM_021154 | PSAT1 |
| NM_178122 | C1orf201 | NM_030940 | ISCA1 |
| NM_015627 | LDLRAP1 | NM_005226 | S1PR3 |
| NM_198137 | CATSPER4 | NM_145006 | SUSD3 |
| NM_145345 | UBXN11 | NM_177995 | PTPDC1 |
| NM_001039775 | AIM1L | NM_003837 | FBP2 |
| NM_152365 | C1orf172 | NM_000507 | FBP1 |
| NM_005281 | GPR3 | NM_173200 | NR4A3 |
| NM_001990 | EYA3 | NM_207299 | PRG-3 |
| NM_001269 | RCC1 | NM_000035 | ALDOB |
| NM_004437 | EPB41 | NM_018112 | TMEM38B |
| NM_002379 | MATN1 | NM_006687 | ACTL7A |
| NM_004814 | SNRNP40 | NM_173521 | C9orf84 |
| NM_023009 | MARCKSL1 | NM_033051 | SLC46A2 |
| NM_005268 | GJB5 | NM_138424 | KIF12 |
| NM_017629 | EIF2C4 | NM_017418 | 1-Dec |
| NM_172313 | CSF3R | NM_198188 | ASTN2 |
| NM_017850 | C1orf109 | NM_001011649 | CDK5RAP2 |
| NM_001113482 | MANEAL | NM_012164 | FBXW2 |
| NR_003929 | LOC728448 | NM_001735 | C5 |
| NM_152373 | ZNF684 | NM_007018 | CEP110 |
| NM_144990 | SLFNL1 | NM_001004450 | OR1B1 |
| NM_007102 | GUCA2B | NR_003071 | SNORD90 |
| NM_144626 | TMEM125 | NM_030978 | ARPC5L |
| NM_182517 | C1orf210 | NM_005833 | RABEPK |
| NM_001005417 | B4GALT2 | NM_006195 | PBX3 |
| NR_000024 | SNORD46 | NM_001011703 | FAM125B |
| NM_153274 | BEST4 | NM_203305 | FAM102A |
| NM_005897 | IPP | NM_032728 | PPAPDC3 |
| NM_004474 | FOXD2 | NR_003050 | SNORD62A |
| NM_032110 | DMRTA2 | NM_018956 | C9orf9 |
| NM_004153 | ORC1L | NM_152572 | C9orf98 |
| NM_001010978 | LDLRAD1 | NM_002003 | FCN1 |
| NM_152607 | C1orf177 | NM_178469 | LCN8 |
| NM_015888 | HOOK1 | NM_016219 | MAN1B1 |
| NM_001083592 | ROR1 | NM_080877 | SLC34A3 |

TABLE 6-continued

List of genes with promoter γH2AX accumulation in SR or SEN cells.

| | | | |
|---|---|---|---|
| NM_152489 | UBE2U | NM_052817 | MID2 |
| NM_001924 | GADD45A | NM_003662 | PIR |
| NM_003838 | FPGT | NM_007220 | CA5B |
| NM_001112808 | TNNI3K | NM_001080975 | REPS2 |
| NM_001002912 | C1orf173 | NM_006089 | SCML2 |
| NM_012152 | LPAR3 | NM_001037343 | CDKL5 |
| NM_016620 | ZNF644 | NR_023358 | SCARNA9L |
| NM_001127215 | GFI1 | NM_001415 | EIF2S3 |
| NM_007358 | MTF2 | NM_177404 | MAGEB1 |
| NM_001114106 | SLC44A3 | NM_004229 | MED14 |
| NM_080630 | COL11A1 | NM_001356 | DDX3X |
| NM_001122961 | C1orf194 | NM_017776 | ZNF673 |
| NM_172212 | CSF1 | NR_015378 | LOC401588 |
| NM_032414 | PROK1 | NM_001039891 | ZNF674 |
| NM_001025197 | CHI3L2 | NM_153280 | UBA1 |
| NM_024102 | WDR77 | NM_007130 | ZNF41 |
| NM_000677 | ADORA3 | NM_001114123 | ELK1 |
| NM_033020 | TRIM33 | NM_007131 | ZNF81 |
| NM_001002810 | PDE4DIP | NM_001037735 | ZNF630 |
| NM_144697 | C1orf51 | NM_203475 | PORCN |
| NM_182578 | THEM5 | NM_000377 | WAS |
| NM_016190 | CRNN | NM_002049 | GATA1 |
| NM_178354 | LCE1F | NM_017602 | OTUD5 |
| NM_001128600 | LCE6A | NM_007075 | WDR45 |
| NM_001024209 | SPRR2E | NM_015698 | GPKOW |
| NM_000427 | LOR | NM_020717 | SHROOM4 |
| NM_005979 | S100A13 | NM_005448 | BMP15 |
| NM_004515 | ILF2 | NM_001010862 | SPIN3 |
| NM_173852 | KRTCAP2 | NM_138737 | HEPH |
| NM_001039517 | C1orf104 | NM_014725 | STARD8 |
| NM_006912 | RIT1 | NM_207320 | OTUD6A |
| NM_006365 | C1orf61 | NM_002565 | P2RY4 |
| NM_021948 | BCAN | NM_004312 | ARR3 |
| NM_001004469 | OR10J5 | NM_007363 | NONO |
| NM_001013661 | VSIG8 | NR_002226 | INGX |
| NM_012337 | CCDC19 | NM_001013627 | NHSL2 |
| NM_001001734 | ATP1A4 | NM_017669 | ERCC6L |
| NM_052931 | SLAMF6 | NR_003255 | TSIX |
| NM_003037 | SLAMF1 | NM_015975 | TAF9B |
| NM_017625 | ITLN1 | NM_153252 | BRWD3 |
| NM_030916 | PVRL4 | NM_000307 | POU3F4 |
| NM_053282 | SH2D1B | NM_033048 | CPXCR1 |
| NM_178550 | C1orf110 | NM_006729 | DIAPH2 |
| NM_018417 | ADCY10 | NM_022144 | TNMD |
| NM_001460 | FMO2 | NM_021637 | TMEM35 |
| NM_001531 | MR1 | NM_022053 | NXF2 |
| NM_005562 | LAMC2 | NM_182581 | TMEM31 |
| NM_002597 | PDC | NM_017416 | IL1RAPL2 |
| NM_005298 | GPR25 | NM_138382 | RIPPLY1 |
| NM_003281 | TNNI1 | NM_018301 | RBM41 |
| NM_001048230 | ADORA1 | NM_173494 | CXorf41 |
| NM_018208 | ETNK2 | NM_002764 | PRPS1 |
| NM_030952 | NUAK2 | NM_001522 | GUCY2F |
| NM_181644 | MFSD4 | NM_001004308 | ZCCHC16 |
| NM_134325 | SLC26A9 | NM_001031855 | LONRF3 |
| NR_004389 | SNORA16B | NM_001152 | SLC25A5 |
| NM_206594 | ESRRG | NM_181777 | UBE2A |
| NR_001587 | AURKAPS1 | NM_017544 | NKRF |
| NM_024709 | C1orf115 | NM_004541 | NDUFA1 |
| NM_014184 | CNIH4 | NM_006978 | RNF113A |
| NM_033445 | HIST3H2A | NM_006777 | ZBTB33 |
| NM_004578 | RAB4A | NM_003588 | CUL4B |
| NM_152379 | C1orf131 | NM_001008222 | ZDHHC9 |
| NM_022051 | EGLN1 | NM_001071188 | HS6ST2 |
| NM_032435 | KIAA1804 | NM_004484 | GPC3 |
| NM_021186 | ZP4 | NM_021796 | PLAC1 |
| NM_024804 | ZNF669 | NM_001013403 | LOC347487 |
| NM_175911 | OR2L13 | NM_004065 | CDR1 |
| NM_019044 | CCDC93 | NM_173078 | SLITRK4 |
| NM_152670 | C2orf51 | NM_001011544 | MAGEA11 |
| NM_001040649 | ACP1 | NM_005342 | HMGB3 |
| NM_015677 | SH3YL1 | NM_004224 | GPR50 |
| NM_175722 | TPO | NM_153478 | CSAG1 |
| NM_138799 | MBOAT2 | NM_005367 | MAGEA12 |
| NM_033090 | GREB1 | NM_007150 | ZNF185 |
| NM_012344 | NTSR2 | NM_001001344 | ATP2B3 |
| NM_182828 | GDF7 | NM_001025243 | IRAK1 |
| NM_181713 | UBXN2A | NR_000011 | SNORA70 |
| NM_001040710 | C2orf84 | NM_004728 | DDX21 |
| NM_153759 | DNMT3A | NM_020397 | CAMK1D |
| NM_017877 | C2orf18 | NM_022365 | DNAJC1 |
| NM_007046 | EMILIN1 | NM_020824 | ARHGAP21 |
| NM_032434 | ZNF512 | NM_014915 | ANKRD26 |
| NM_020744 | MTA3 | NM_052997 | ANKRD30A |
| NM_022436 | ABCG5 | NM_003421 | ZNF37A |
| NM_001003937 | TSPYL6 | NM_145312 | ZNF485 |
| NM_014562 | OTX1 | NM_014696 | GPRIN2 |
| NM_006759 | UGP2 | NM_001098512 | PRKG1 |
| NM_152792 | ASPRV1 | NM_022079 | HERC4 |
| NM_001692 | ATP6V1B1 | NM_030625 | TET1 |
| NM_020459 | PAIP2B | NM_014767 | SPOCK2 |
| NM_144579 | SFXN5 | NM_001114133 | SYNPO2L |
| NM_003960 | NAT8 | NR_002724 | MBL1P1 |
| NM_001615 | ACTG2 | NM_032372 | DYDC2 |
| NM_021196 | SLC4A5 | NM_138812 | DYDC1 |
| NM_016170 | TLX2 | NM_006829 | C10orf116 |
| NM_021103 | TMSB10 | NM_148978 | PANK1 |
| NM_031283 | TCF7L1 | NM_006413 | RPP30 |
| NM_017952 | PTCD3 | NM_004523 | KIF11 |
| NR_003503 | GGT8P | NM_015385 | SORBS1 |
| NM_002371 | MAL | NM_020349 | ANKRD2 |
| NM_013434 | KCNIP3 | NM_138413 | C10orf65 |
| NM_001037228 | LOC285033 | NM_001009997 | C10orf62 |
| NM_001079 | ZAP70 | NM_031212 | SLC25A28 |
| NM_138798 | MITD1 | NM_003988 | PAX2 |
| NM_001025108 | AFF3 | NM_013274 | POLL |
| NM_173343 | IL1R2 | NM_002779 | PSD |
| NM_173205 | IL1F7 | NM_002925 | RGS10 |
| NM_173161 | IL1F10 | NM_024834 | C10orf19 |
| NM_173842 | IL1RN | NR_003570 | FLJ46361 |
| NM_012184 | FOXD4L1 | NM_001105574 | HMX3 |
| NM_002830 | PTPN4 | NM_001007793 | BUB3 |
| NM_032740 | SFT2D3 | NM_153442 | GPR26 |
| NM_138770 | CCDC74A | NM_000375 | UROS |
| NM_144586 | LYPD1 | NM_018180 | DHX32 |
| NM_019845 | RPRM | NM_001380 | DOCK1 |
| NM_001009959 | ERMN | NM_006426 | DPYSL4 |
| NM_002349 | LY75 | NM_003577 | UTF1 |
| NM_173162 | KCNH7 | NM_001098483 | C10orf125 |
| NM_000523 | HOXD13 | NM_145651 | SCGB1C1 |
| NM_012086 | GTF3C3 | NM_001039490 | CD151 |
| NM_199440 | HSPD1 | NM_138567 | SYT8 |
| NM_001228 | CASP8 | NM_001013254 | LSP1 |
| NM_001102659 | LOC200726 | NM_199292 | TH |
| NM_005210 | CRYGB | NM_014555 | TRPM5 |
| NM_000634 | IL8RA | NM_001039165 | MRGPRE |
| NM_007127 | VIL1 | NM_003141 | TRIM21 |
| NM_001105537 | ZNF142 | NM_001004137 | OR52M1 |
| NM_003936 | CDK5R2 | NM_001004757 | OR51Q1 |
| NM_001005176 | SP140 | NR_002777 | TRIMP1 |
| NM_030926 | ITM2C | NM_176875 | CCKBR |
| NM_031313 | ALPPL2 | NM_012192 | FXC1 |
| NM_005199 | CHRNG | NM_016229 | CYB5R2 |
| NM_007120 | UGT1A4 | NM_001003745 | OR10A3 |
| NM_018410 | HJURP | NM_005418 | ST5 |
| NM_001005853 | OR6B2 | NM_001031853 | INSC |
| NM_001080835 | LOC643905 | NM_017508 | SOX6 |
| NM_005301 | GPR35 | NM_000525 | KCNJ11 |
| NM_015148 | PASK | NM_002478 | MYOD1 |
| NM_002712 | PPP1R7 | NM_194285 | SPTY2D1 |
| NM_175727 | IL5RA | NM_003986 | BBOX1 |
| NM_020873 | LRRN1 | NM_001031854 | ACCSL |
| NM_033337 | CAV3 | NM_001031730 | TSPAN18 |
| NM_014850 | SRGAP3 | NM_000256 | MYBPC3 |
| NM_033084 | FANCD2 | NM_001004727 | OR4X2 |
| NM_003178 | SYN2 | NM_001005201 | OR8H3 |
| NM_005037 | PPARG | NM_001004064 | OR8J3 |
| NM_025265 | TSEN2 | NM_001004746 | OR5T2 |
| NM_012298 | CAND2 | NM_001005210 | LRRC55 |
| NM_001007073 | RPL32 | NM_000062 | SERPING1 |
| NM_024827 | HDAC11 | NM_145008 | YPEL4 |
| NM_001080423 | GRIP2 | NM_005838 | GLYAT |
| NM_020839 | WDR48 | NM_001004706 | OR4D11 |
| NM_001337 | CX3CR1 | NM_152716 | PATL1 |

TABLE 6-continued

List of genes with promoter γH2AX accumulation in SR or SEN cells.

| | | | |
|---|---|---|---|
| NM_005201 | CCR8 | NM_178031 | TMEM132A |
| NM_001098414 | ZNF621 | NM_152718 | VWCE |
| NM_020707 | HHATL | NM_021727 | FADS3 |
| NM_173658 | ZNF660 | NM_020238 | INCENP |
| NM_145044 | ZNF501 | NM_006473 | TAF6L |
| NM_013270 | TSP50 | NM_199337 | TMEM179B |
| NM_182702 | TESSP2 | NM_198897 | FIBP |
| NM_001008269 | TMEM89 | NM_178864 | NPAS4 |
| NM_000884 | IMPDH2 | NM_003793 | CTSF |
| NM_001640 | APEH | NM_014578 | RHOD |
| NM_007024 | TMEM115 | NM_017857 | SSH3 |
| NM_152397 | IQCF1 | NM_000695 | ALDH3B2 |
| NM_144641 | PPM1M | NM_002335 | LRP5 |
| NM_020163 | SEMA3G | NM_005247 | FGF3 |
| NM_002218 | ITIH4 | NM_000803 | FOLR2 |
| NM_205853 | MUSTN1 | NM_033388 | ATG16L2 |
| NM_001126128 | PROK2 | NM_004154 | P2RY6 |
| NM_001105580 | GABRR3 | NM_021200 | PLEKHB1 |
| NM_001042459 | FILIP1L | NM_004041 | ARRB1 |
| NM_032787 | GPR128 | NM_015516 | TSKU |
| NM_014981 | MYH15 | NM_182833 | GDPD4 |
| NM_001008273 | TAGLN3 | NM_153696 | PSMAL |
| NM_001025073 | C3orf17 | NM_001105522 | LOC729384 |
| NM_152538 | IGSF11 | NM_033135 | PDGFD |
| NM_005191 | CD80 | NM_002906 | RDX |
| NM_175924 | ILDR1 | NM_015191 | SIK2 |
| NM_182628 | CCDC37 | NM_001101389 | LOC644672 |
| NM_013336 | SEC61A1 | NM_152315 | FAM55A |
| NM_153330 | DNAJB8 | NM_001077263 | TMPRSS13 |
| NM_020187 | C3orf37 | NM_001467 | SLC37A4 |
| NM_001042384 | CEP63 | NM_024791 | PDZD3 |
| NM_004189 | SOX14 | NM_004205 | USP2 |
| NM_001002026 | CLDN18 | NM_001005197 | OR8D4 |
| NM_016161 | A4GNT | NM_001002918 | OR8D2 |
| NM_004766 | COPB2 | NM_017425 | SPA17 |
| NM_080862 | SPSB4 | NM_025004 | CCDC15 |
| NM_139209 | GRK7 | NM_022112 | P53AIP1 |
| NM_013308 | GPR171 | NM_138342 | GLB1L2 |
| NM_014575 | SCHIP1 | NM_003044 | SLC6A12 |
| NM_000882 | IL12A | NM_001039029 | LRTM2 |
| NM_173084 | TRIM59 | NM_020996 | FGF6 |
| NM_004122 | GHSR | NM_001769 | CD9 |
| NM_130770 | HTR3C | NM_020040 | LPAR5 |
| NM_001100120 | ECE2 | NM_002075 | GNB3 |
| NM_001102416 | KNG1 | NM_002543 | OLR1 |
| NM_130834 | OPA1 | NM_020853 | KIAA1467 |
| NM_152531 | C3orf21 | NM_005504 | BCAT1 |
| NM_138461 | TM4SF19 | NM_001098531 | RAPGEF3 |
| NM_182524 | ZNF595 | NM_014554 | SENP1 |
| NM_001039127 | ZNF718 | NM_012272 | PRPF40B |
| NM_017733 | PIGG | NM_001971 | ELA1 |
| NM_022042 | SLC26A1 | NM_175053 | KRT74 |
| NM_003023 | SH3BP2 | NM_153633 | HOXC4 |
| NM_198229 | RGS12 | NM_006163 | NFE2 |
| NM_001113361 | TBC1D14 | NM_020370 | GPR84 |
| NM_001001290 | SLC2A9 | NM_006741 | PPP1R1A |
| NM_004787 | SLIT2 | NM_021191 | NEUROD4 |
| NM_147183 | KCNIP4 | NM_002206 | ITGA7 |
| NM_015187 | KIAA0746 | NM_002429 | MMP19 |
| NM_018302 | C4orf19 | NM_022465 | IKZF4 |
| NM_207406 | BEND4 | NM_012064 | MIP |
| NM_198353 | KCTD8 | NR_003046 | SNORD59B |
| NM_000809 | GABRA4 | NM_148897 | SDR9C7 |
| NM_032622 | LNX1 | NM_024779 | PIP4K2C |
| NM_032495 | HOPX | NM_001478 | B4GALNT1 |
| NM_020368 | UTP3 | NM_000075 | CDK4 |
| NM_000584 | IL8 | NM_015026 | MON2 |
| NM_033214 | GK2 | NM_022496 | ACTR6 |
| NM_001003810 | HNRNPD | NM_016053 | CCDC53 |
| NM_001098540 | HPSE | NM_006825 | CKAP4 |
| NM_032717 | AGPAT9 | NM_002920 | RFX4 |
| NM_138980 | MAPK10 | NM_203436 | ASCL4 |
| NM_178135 | HSD17B13 | NM_057169 | GIT2 |
| NM_198281 | GPRIN3 | NM_002710 | PPP1CC |
| NM_183049 | TMSL3 | NM_001034025 | ERP29 |
| NM_000671 | ADH5 | NM_181578 | RFC5 |
| NM_000670 | ADH4 | NM_002859 | PXN |
| NM_000667 | ADH1A | NM_015918 | POP5 |
| NM_000673 | ADH7 | NM_004276 | CABP1 |
| NM_033430 | PDE5A | NM_000545 | HNF1A |
| NM_152778 | MFSD8 | NM_016237 | ANAPC5 |
| NM_000910 | NPY2R | NM_207437 | DNAH10 |
| NM_005651 | TDO2 | NM_144669 | GLT1D1 |
| NM_005038 | PPID | NM_183044 | RNF6 |
| NM_017923 | 1-Mar | NM_017826 | SOHLH2 |
| NM_006792 | MORF4 | NM_001009814 | KIAA0564 |
| NR_003612 | FAM92A3 | NM_002498 | NEK3 |
| NM_207352 | CYP4V2 | NM_001011724 | HNRNPA1L2 |
| NM_000128 | F11 | NM_022843 | PCDH20 |
| NM_013232 | PDCD6 | NM_006346 | PIBF1 |
| NM_024786 | ZDHHC11 | NM_014305 | TGDS |
| NM_001044 | SLC6A3 | NM_019616 | F7 |
| NM_020227 | PRDM9 | NM_000504 | F10 |
| NM_018356 | C5orf22 | NM_198235 | RNASE1 |
| NM_005983 | SKP2 | NM_201535 | NDRG2 |
| NM_001007527 | LMBRD2 | NM_001012264 | RNASE13 |
| NM_018034 | WDR70 | NM_007192 | SUPT16H |
| NM_152403 | EGFLAM | NM_001344 | DAD1 |
| NM_000163 | GHR | NM_000359 | TGM1 |
| NM_022483 | C5orf28 | NM_138452 | DHRS1 |
| NM_022132 | MCCC2 | NM_032594 | INSM2 |
| NM_004291 | CARTPT | NM_032352 | BRMS1L |
| NM_153217 | TMEM174 | NM_003317 | NKX2-1 |
| NM_001004441 | ANKRD34B | NM_001202 | BMP4 |
| NM_173061 | CAST | NM_015589 | SAMD4A |
| NM_001962 | EFNA5 | NM_014992 | DAAM1 |
| NM_022828 | YTHDC2 | NM_004857 | AKAP5 |
| NM_014350 | TNFAIP8 | NM_001039465 | SFRS5 |
| NM_153223 | CEP120 | NM_015351 | TTC9 |
| NM_001017974 | P4HA2 | NM_018228 | C14orf115 |
| NM_021982 | SEC24A | NM_002632 | PGF |
| NM_145282 | LOC153328 | NM_004452 | ESRRB |
| NM_015564 | LRRTM2 | NM_024496 | C14orf4 |
| NM_001033112 | PAIP2 | NM_033426 | KIAA1737 |
| NM_016459 | MGC29506 | NM_145870 | GSTZ1 |
| NM_001077693 | ECSCR | NM_015859 | GTF2A1 |
| NM_032289 | PSD2 | NM_001275 | CHGA |
| NM_018911 | PCDHA8 | NM_022151 | MOAP1 |
| NM_031857 | PCDHA9 | NM_006215 | SERPINA4 |
| NM_031883 | PCDHAC2 | NR_003234 | SNORD113-6 |
| NM_018936 | PCDHB2 | NR_003196 | SNORD114-4 |
| NM_031947 | SLC25A2 | NR_003316 | SNORD116-1 |
| NM_004576 | PPP2R2B | NR_003324 | SNORD116-3 |
| NM_001040174 | HTR4 | NR_003330 | SNORD116-15 |
| NM_024577 | SH3TC2 | NR_003311 | SNORD115-17 |
| NM_133263 | PPARGC1B | NR_003313 | SNORD115-20 |
| NM_001804 | CDX1 | NR_003496 | HBII-52-27 |
| NM_130899 | FAM71B | NR_003350 | SNORD115-35 |
| NM_001037333 | CYFIP2 | NR_003353 | SNORD115-38 |
| NM_007017 | SOX30 | NR_003355 | SNORD115-40 |
| NM_000816 | GABRG2 | NM_017762 | MTMR10 |
| NM_199246 | CCNG1 | NM_001103184 | FMN1 |
| NM_145266 | NUDCD2 | NM_005135 | SLC12A6 |
| NM_001102609 | LOC133874 | NM_170675 | MEIS2 |
| NM_001029886 | PFN3 | NM_152453 | TMCO5A |
| NM_019057 | FLJ10404 | NM_033286 | C15orf23 |
| NM_001024649 | CANX | NM_133639 | RHOV |
| NM_201627 | TRIM41 | NM_020857 | VPS18 |
| NR_002592 | SNORD96A | NM_016642 | SPTBN5 |
| NM_138296 | PTCRA | NM_022473 | ZFP106 |
| NM_018303 | EXOC2 | NM_000119 | EPB42 |
| NM_004568 | SERPINB6 | NM_004245 | TGM5 |
| NM_205864 | CAGE1 | NM_014985 | CEP152 |
| NM_153005 | RIOK1 | NM_016194 | GNB5 |
| NR_004855 | HULC | NM_130810 | DYX1C1 |
| NM_153003 | OFCC1 | NM_012182 | FOXB1 |
| NM_003220 | TFAP2A | NM_004663 | RAB11A |
| NM_016462 | TMEM14C | NM_016166 | PIAS1 |
| NM_207582 | HERV-FRD | NM_022369 | STRA6 |
| NM_138574 | HDGFL1 | NM_020447 | C15orf17 |
| NM_014722 | FAM65B | NM_173469 | UBE2Q2 |
| NM_170610 | HIST1H2BA | NM_003978 | PSTPIP1 |
| NM_006355 | TRIM38 | NM_022566 | MESDC1 |
| NM_003523 | HIST1H2BE | NM_201651 | SLC28A1 |

TABLE 6-continued

List of genes with promoter γH2AX accumulation in SR or SEN cells.

| | | | |
|---|---|---|---|
| NM_003532 | HIST1H3E | NM_000326 | RLBP1 |
| NM_001732 | BTN1A1 | NM_198925 | SEMA4B |
| NM_003511 | HIST1H2AL | NM_002569 | FURIN |
| NM_005322 | HIST1H1B | NM_018668 | VPS33B |
| NM_003447 | ZNF165 | NM_006011 | ST8SIA2 |
| NM_021253 | TRIM39 | NM_001102612 | LOC145814 |
| NM_005803 | FLOT1 | NM_016310 | POLR3K |
| NR_003948 | HCG22 | NM_016541 | GNG13 |
| NM_000595 | LTA | NM_207419 | C1QTNF8 |
| NR_002971 | SNORA38 | NM_024164 | TPSB2 |
| NM_025258 | C6orf27 | NM_023076 | UNKL |
| NM_006929 | SKIV2L | NM_004970 | IGFALS |
| NM_033554 | HLA-DPA1 | NR_002327 | SNORA10 |
| NM_005453 | ZBTB22 | NM_174903 | RNF151 |
| NM_018679 | TCP11 | NM_005262 | GFER |
| NM_153487 | MDGA1 | NM_022372 | GBL |
| NM_031460 | KCNK17 | NM_182563 | C16orf79 |
| NM_024807 | TREML2 | NM_001374 | DNASE1L2 |
| NM_018643 | TREM1 | NM_001919 | DCI |
| NM_002630 | PGC | NM_001089 | ABCA3 |
| NM_000322 | PRPH2 | NM_007108 | TCEB2 |
| NM_003192 | TBCC | NM_172229 | KREMEN2 |
| NM_023932 | DLK2 | NR_002169 | OR1F2 |
| NM_021572 | ENPP5 | NM_138440 | VASN |
| NM_005588 | MEP1A | NM_000833 | GRIN2A |
| NM_000847 | GSTA3 | NM_170664 | OTOA |
| NM_004282 | BAG2 | NM_173806 | C16orf65 |
| NM_183227 | RAB23 | NM_006043 | HS3ST2 |
| NM_078485 | COL9A1 | NM_032038 | SPNS1 |
| NM_014989 | RIMS1 | NM_006319 | CDIPT |
| NM_002395 | ME1 | NM_152458 | ZNF785 |
| NM_016230 | CYB5R4 | NM_001080417 | ZNF629 |
| NM_000865 | HTR1E | NM_000887 | ITGAX |
| NM_001042493 | C6orf162 | NM_016633 | ERAF |
| NM_020320 | RARS2 | NM_145186 | ABCC11 |
| NM_002042 | GABRR1 | NM_017839 | LPCAT2 |
| NM_015891 | CDC40 | NM_005949 | MT1F |
| NM_001013734 | RFPL4B | NM_005950 | MT1G |
| NM_173560 | RFX6 | NM_153837 | GPR114 |
| NM_001029858 | SLC35F1 | NM_170776 | GPR97 |
| NM_020755 | SERINC1 | NM_001297 | CNGB1 |
| NM_033515 | ARHGAP18 | NM_001080492 | KLKBL4 |
| NM_022121 | PERP | NM_020465 | NDRG4 |
| NM_020340 | KIAA1244 | NM_001796 | CDH8 |
| NM_015439 | CCDC28A | NM_173815 | CES8 |
| NM_033071 | SYNE1 | NM_014329 | EDC4 |
| NM_014892 | RBM16 | NM_002801 | PSMB10 |
| NM_207118 | GTF2H5 | NM_012320 | PLA2G15 |
| NM_138810 | TAGAP | NM_032178 | SLC7A6OS |
| NM_016098 | BRP44L | NM_018667 | SMPD3 |
| NR_002787 | LOC154449 | NM_138612 | HAS3 |
| NM_001098201 | GPER | NM_030579 | CYB5B |
| NM_007353 | GNA12 | NM_006927 | ST3GAL2 |
| NR_015343 | LOC389458 | NM_138994 | CNTNAP4 |
| NM_014304 | BZW2 | NM_014861 | ATP2C2 |
| NR_022006 | KIAA0087 | NM_031476 | CRISPLD2 |
| NM_000823 | GHRHR | NM_152287 | ZNF276 |
| NM_006658 | C7orf16 | NM_145068 | TRPV3 |
| NM_207173 | NPSR1 | NM_144611 | CYB5D2 |
| NM_181791 | GPR141 | NM_001140 | ALOX15 |
| NM_001105282 | FAM183B | NM_003562 | SLC25A11 |
| NM_021223 | MYL7 | NM_020795 | NLGN2 |
| NM_013389 | NPC1L1 | NM_001251 | CD68 |
| NR_002990 | SNORA5B | NM_153007 | ODF4 |
| NM_021116 | ADCY1 | NM_001010855 | PIK3R6 |
| NM_000790 | DDC | NM_004822 | NTN1 |
| NM_182546 | VSTM2A | NM_139162 | SMCR7 |
| NM_016220 | ZNF107 | NM_144775 | SMCR8 |
| NM_015852 | ZNF117 | NM_004618 | TOP3A |
| NM_031468 | CALN1 | NM_007148 | RNF112 |
| NM_002835 | PTPN12 | NM_001080837 | SEBOX |
| NM_012395 | PFTK1 | NM_003593 | FOXN1 |
| NM_019004 | ANKIB 1 | NM_031934 | RAB34 |
| NM_004912 | KRIT1 | NR_000014 | SNORD42A |
| NM_006528 | TFPI2 | NM_020791 | TAOK1 |
| NM_018842 | BAIAP2L1 | NM_015986 | CRLF3 |
| NM_003496 | TRRAP | NM_015544 | TMEM98 |
| NM_057096 | CYP3A43 | NM_001094 | ACCN1 |
| NM_001185 | AZGP1 | NM_145272 | C17orf50 |
| NM_006833 | COPS6 | NM_024864 | MRM1 |
| NM_003227 | TFR2 | NM_000458 | HNF1B |
| NM_002291 | LAMB1 | NM_003673 | TCAP |
| NM_182597 | C7orf53 | NM_021724 | NR1D1 |
| NM_003391 | WNT2 | NM_019010 | KRT20 |
| NM_016087 | WNT16 | NM_031961 | KRTAP9-2 |
| NM_002851 | PTPRZ1 | NM_001524 | HCRT |
| NM_001024613 | FEZF1 | NM_001991 | EZH1 |
| NM_003117 | SPAM1 | NM_080863 | ASB16 |
| NM_006193 | PAX4 | NM_145663 | DBF4B |
| NR_002187 | LOC286016 | NM_005892 | FMNL1 |
| NM_001869 | CPA2 | NM_199282 | ARHGAP27 |
| NM_001105543 | PLXNA4 | NM_175882 | IMP5 |
| NM_002825 | PTN | NM_001007532 | STH |
| NM_001085429 | TMEM213 | NM_024320 | ATAD4 |
| NM_032295 | SLC37A3 | NM_152244 | SNX11 |
| NM_176817 | TAS2R38 | NM_000023 | SGCA |
| NM_019841 | TRPV5 | NM_001267 | CHAD |
| NM_001031690 | FAM131B | NM_004655 | AXIN2 |
| NM_175571 | GIMAP8 | NM_000346 | SOX9 |
| NM_014020 | TMEM176B | NM_000835 | GRIN2C |
| NM_144727 | CRYGN | NM_015353 | KCTD2 |
| NM_001040633 | PRKAG2 | NM_001005849 | SUMO2 |
| NM_033225 | CSMD1 | NM_001005619 | ITGB4 |
| NM_002052 | GATA4 | NM_180990 | ZACN |
| NM_000237 | LPL | NM_006640 | 9-Sep |
| NM_001114137 | EPB49 | NM_001042573 | FLJ21865 |
| NM_144962 | PEBP4 | NM_178543 | ENPP7 |
| NM_007257 | PNMA2 | NM_024110 | CARD14 |
| NM_171982 | TRIM35 | NM_181483 | C18orf1 |
| NM_013959 | NRG1 | NM_003799 | RNMT |
| NM_152413 | GOT1L1 | NM_020805 | KLHL14 |
| NR_003129 | RNF5P1 | NM_032980 | DTNA |
| NR_001569 | tMDC | NM_018170 | RPRD1A |
| NM_014420 | DKK4 | NM_001008239 | C18orf25 |
| NM_002027 | FNTA | NM_001101654 | CXXC1 |
| NM_006269 | RP1 | NM_018696 | ELAC1 |
| NM_138969 | SDR16C5 | NM_012397 | SERPINB13 |
| NM_001007070 | SDCBP | NM_001037331 | C18orf62 |
| NM_032466 | ASPH | NM_001025101 | MBP |
| NM_000370 | TTPA | NM_014913 | ADNP2 |
| NM_002604 | PDE7A | NM_198969 | AES |
| NM_144650 | ADHFE1 | NM_001017392 | SFRS14 |
| NM_013257 | SGK3 | NM_182577 | ODF3L2 |
| NM_025170 | PREX2 | NM_005860 | FSTL3 |
| NM_006540 | NCOA2 | NM_002777 | PRTN3 |
| NM_007332 | TRPA1 | NM_001001975 | ATP5D |
| NM_004770 | KCNB2 | NM_005883 | APC2 |
| NM_024721 | ZFHX4 | NM_003021 | SGTA |
| NM_198584 | CA13 | NM_021231 | C19orf29 |
| NM_020209 | SHD | NM_001103176 | CNPY1 |
| NM_001013706 | LSDP5 | NM_014671 | UBE3C |
| NM_005817 | M6PRBP1 | NM_001040032 | C8orf74 |
| NM_015318 | ARHGEF18 | NM_031439 | SOX7 |
| NM_020533 | MCOLN1 | NM_001127505 | ASAH1 |
| NM_006949 | STXBP2 | NM_003155 | STC1 |
| NM_001042462 | TRAPPC5 | NM_015254 | KIF13B |
| NM_002002 | FCER2 | NM_021631 | FKSG2 |
| NM_001004456 | OR1M1 | NR_003671 | LOC728024 |
| NM_001005193 | OR7G2 | NM_003012 | SFRP1 |
| NM_003451 | ZNF177 | NM_001556 | IKBKB |
| NM_003259 | ICAM5 | NM_000749 | CHRNB3 |
| NM_001611 | ACP5 | NM_001005365 | POTEA |
| NM_006397 | RNASEH2A | NM_144651 | PXDNL |
| NM_006563 | KLF1 | NM_005098 | MSC |
| NM_004907 | IER2 | NM_000971 | RPL7 |
| NM_003765 | STX10 | NM_172037 | RDH10 |
| NM_024323 | C19orf57 | NM_024699 | ZFAND1 |
| NM_001007525 | NWD1 | NM_152284 | CHMP4C |
| NM_015260 | SIN3B | NM_001100393 | RALYL |
| NM_000923 | PDE4C | NM_001083588 | E2F5 |
| NM_004750 | CRLF1 | NM_019098 | CNGB3 |
| NM_004720 | LPAR2 | NM_002380 | MATN2 |
| NM_021047 | ZNF253 | NM_001029860 | FBXO43 |
| NM_033468 | ZNF257 | NM_152888 | COL22A1 |

TABLE 6-continued

List of genes with promoter γH2AX accumulation in SR or SEN cells.

| | | | |
|---|---|---|---|
| NM_001098626 | ZNF98 | NM_207414 | FLJ43860 |
| NM_021175 | HAMP | NM_177458 | LYNX1 |
| NM_015302 | KIAA0841 | NM_201379 | PLEC1 |
| NM_001863 | COX6B1 | NM_001129888 | CYHR1 |
| NM_052948 | SNX26 | NM_025251 | KIAA1688 |
| NM_004646 | NPHS1 | NM_021951 | DMRT1 |
| NM_020951 | ZNF529 | NM_005059 | RLN2 |
| NM_152605 | ZNF781 | NM_001099223 | IFT74 |
| NM_001042507 | LGALS7B | NM_145005 | C9orf72 |
| NM_020862 | LRFN1 | NM_004512 | IL11RA |
| NM_016941 | DLL3 | NM_020944 | GBA2 |
| NM_182704 | SELV | NM_016042 | EXOSC3 |
| NM_152361 | EID2B | NM_153237 | C9orf71 |
| NM_033543 | CEACAM21 | NM_032171 | CEP78 |
| NM_001817 | CEACAM4 | NM_004938 | DAPK1 |
| NM_198850 | PHLDB3 | NM_001912 | CTSL1 |
| NM_182498 | ZNF428 | NM_001023564 | CTSL3 |
| NM_198478 | NKPD1 | NM_033014 | OGN |
| NM_033258 | GNG8 | NM_000136 | FANCC |
| NM_019855 | CABP5 | NM_014930 | ZNF510 |
| NM_014959 | CARD8 | NM_002486 | NCBP1 |
| NM_031485 | GRWD1 | NM_014788 | TRIM14 |
| NM_177973 | SULT2B1 | NM_197977 | ZNF189 |
| NM_000979 | RPL18 | NM_001017998 | GNG10 |
| NM_145807 | NTN5 | NM_032303 | HSDL2 |
| NM_006179 | NTF4 | NM_021218 | C9orf80 |
| NM_031886 | KCNA7 | NM_005118 | TNFSF15 |
| NM_001040031 | CD37 | NM_001244 | TNFSF8 |
| NM_020309 | SLC17A7 | NM_002077 | GOLGA1 |
| NM_017432 | PTOV1 | NM_001100877 | PHYHD1 |
| NM_152899 | IL4I1 | NM_014581 | OBP2B |
| NM_052884 | SIGLEC11 | NM_015837 | FCN2 |
| NM_001030049 | KLK3 | NM_001080849 | DNLZ |
| NM_004917 | KLK4 | NM_024174 | C9orf86 |
| NM_001012964 | KLK6 | NM_004479 | FUT7 |
| NM_016543 | SIGLEC7 | NM_000718 | CACNA1B |
| NM_053003 | SIGLEC12 | NM_001727 | BRS3 |
| NM_001462 | FPR2 | NM_005044 | PRKX |
| NM_173857 | VN1R4 | NM_001042480 | GEMIN8 |
| NR_003699 | ZNF525 | NM_005089 | ZRSR2 |
| NM_001110514 | EBF4 | NM_004057 | S100G |
| NM_024958 | NRSN2 | NM_001024666 | SH3KBP1 |
| NM_001040007 | RSPO4 | NM_152577 | ZNF645 |
| NM_198994 | TGM6 | NM_031442 | TMEM47 |
| NM_014731 | ProSAPiP1 | NM_152856 | RBM10 |
| NM_025220 | ADAM33 | NM_019056 | NDUFB11 |
| NM_024960 | PANK2 | NM_175293 | SSX5 |
| NM_012409 | PRND | NM_003173 | SUV39H1 |
| NM_170774 | RASSF2 | NM_013271 | PCSK1N |
| NM_144773 | PROKR2 | NM_000084 | CLCN5 |
| NM_003434 | ZNF133 | NM_031497 | HUWE1 |
| NM_016652 | CRNKL1 | NM_152424 | FAM123B |
| NM_153675 | FOXA2 | NM_207422 | FLJ44635 |
| NM_001052 | SSTR4 | NM_152694 | ZCCHC5 |
| NM_005492 | CST8 | NM_003022 | SH3BGRL |
| NM_032609 | COX4I2 | NM_001105243 | PCDH19 |
| NM_001011718 | XKR7 | NM_001031834 | RAB40AL |
| NM_182658 | C20orf185 | NM_001113490 | AMOT |
| NM_021215 | RPRD1B | NM_007231 | SLC6A14 |
| NR_002911 | SNORA71A | NM_145800 | 6-Sep |
| NM_003064 | SLPI | NM_012084 | GLUD2 |
| NM_181502 | SPINLW1 | NM_001042751 | STAG2 |
| NM_147198 | WFDC9 | NM_001114937 | SH2D1A |
| NM_172113 | WFDC10B | NM_001078172 | FAM127B |
| NM_052951 | DNTTIP1 | NM_006359 | SLC9A6 |
| NM_080752 | ZSWIM3 | NM_000074 | CD40LG |
| NM_080608 | C20orf165 | NM_032512 | PDZD4 |
| NM_172113 | EYA2 | NM_024332 | BRCC3 |
| NM_005985 | SNAI1 | NM_001818 | AKR1C4 |
| NM_199129 | TMEM189 | NM_153256 | C10orf47 |
| NM_199203 | TMEM189-UBE2V1 | NM_153244 | C10orf111 |
| NM_018431 | DOK5 | NR_023388 | PRINS |
| NM_080617 | CBLN4 | NM_017433 | MYO3A |
| NM_017495 | RBM38 | NM_173576 | MKX |
| NR_003505 | PPP4R1L | NM_021738 | SVIL |
| NM_207034 | EDN3 | NM_003591 | CUL2 |
| NM_152757 | C20orf200 | NM_153368 | GJD4 |
| NM_017896 | C20orf11 | NM_001004297 | OR13A1 |
| NM_172109 | KCNQ2 | NM_020945 | WDFY4 |
| NM_005975 | PTK6 | NM_001079516 | ASAH2B |
| NM_033405 | PRIC285 | NM_194298 | SLC16A9 |
| NM_012384 | GMEB2 | NM_030759 | NRBF2 |
| NM_182482 | BAGE2 | NM_201262 | DNAJC12 |
| NM_182484 | BAGE5 | NM_024045 | DDX50 |
| NM_001187 | BAGE | NM_015634 | KIAA1279 |
| NR_003087 | ABCC13 | NM_018649 | H2AFY2 |
| NM_022136 | SAMSN1 | NM_020799 | STAMBPL1 |
| NM_001338 | CXADR | NR_002779 | NUDT9P1 |
| NM_181600 | KRTAP13-4 | NM_032373 | PCGF5 |
| NM_181615 | KRTAP20-1 | NM_173497 | HECTD2 |
| NM_175858 | KRTAP11-1 | NM_003061 | SLIT1 |
| NM_005806 | OLIG2 | NM_018425 | PI4K2A |
| NM_058182 | FAM165B | NM_182639 | HPS1 |
| NM_130436 | DYRK1A | NM_001278 | CHUK |
| NM_033173 | B3GALT5 | NM_005029 | PITX3 |
| NM_182832 | PLAC4 | NM_015916 | CALHM2 |
| NM_002462 | MX1 | NM_001129742 | CALHM3 |
| NM_207629 | ABCG1 | NM_000681 | ADRA2A |
| NM_003226 | TFF3 | NM_002313 | ABLIM1 |
| NM_018961 | UBASH3A | NR_003251 | INPP5F |
| NM_018964 | SLC37A1 | NM_014468 | VENTX |
| NM_003307 | TRPM2 | NM_001109 | ADAM8 |
| NM_198699 | KRTAP10-12 | NM_000773 | CYP2E1 |
| NM_003343 | UBE2G2 | NM_025092 | ATHL1 |
| NM_032261 | C21orf56 | NM_001012416 | KRTAP5-6 |
| NM_006272 | S100B | NM_002555 | SLC22A18 |
| NM_053006 | TSSK2 | NM_001005161 | OR52B4 |
| NM_003776 | MRPL40 | NM_001004753 | OR51F2 |
| NM_003325 | HIRA | NM_001005567 | OR51B5 |
| NM_007310 | COMT | NM_001005288 | OR51I1 |
| NM_002650 | PI4KA | NM_130389 | TRIM34 |
| NM_004173 | SLC7A4 | NM_198185 | OVCH2 |
| NM_007128 | VPREB1 | NM_001004461 | OR10A6 |
| NM_002073 | GNAZ | NM_001025389 | AMPD3 |
| NM_001007468 | SMARCB1 | NM_012250 | RRAS2 |
| NR_001283 | TOP1P2 | NM_016451 | COPB1 |
| NM_001008566 | TPST2 | NM_000922 | PDE3B |
| NM_001886 | CRYBA4 | NM_001741 | CALCA |
| NM_012399 | PITPNB | NM_000728 | CALCB |
| NM_013387 | UCRC | NM_006292 | TSG101 |
| NM_004861 | GAL3ST1 | NM_032781 | PTPN5 |
| NM_014227 | SLC5A4 | NM_213599 | ANO5 |
| NM_001098535 | RFPL3 | NM_177553 | GAS2 |
| NR_001450 | RFPL3S | NM_001018080 | FSHB |
| NM_182486 | C1QTNF6 | NM_001127612 | PAX6 |
| NM_032561 | C22orf23 | NM_001752 | CAT |
| NM_181773 | APOBEC3H | NM_002391 | MDK |
| NM_153497 | MAP3K7IP1 | NM_016223 | PACSIN3 |
| NM_005297 | MCHR1 | NM_024783 | AGBL2 |
| NM_003932 | ST13 | NM_001005272 | OR4A5 |
| NM_152513 | MEI1 | NM_001003750 | OR8I2 |
| NM_145733 | 3-Sep | NM_198183 | UBE2L6 |
| NM_007326 | CYB5R3 | NM_001085468 | CTNND1 |
| NM_001012986 | LOC388910 | NM_001005212 | OR9Q1 |
| NM_001123225 | C22orf41 | NM_001079807 | PGA3 |
| NM_152228 | TAS1R3 | NM_004111 | FEN1 |
| NM_001003808 | C1orf222 | NM_022830 | TUT1 |
| NM_207306 | KIAA0495 | NM_012200 | B3GAT3 |
| NM_181866 | ACOT7 | NM_198334 | GANAB |
| NM_001042665 | PLEKHG5 | NR_002560 | SNORD31 |
| NM_004401 | DFFA | NR_002561 | SNORD30 |
| NM_001103170 | AADACL3 | NR_002559 | SNORD29 |
| NM_032341 | DDI2 | NM_017490 | MARK2 |
| NM_178840 | C1orf64 | NM_014067 | MACROD1 |
| NM_004070 | CLCNKA | NM_024650 | C11orf80 |
| NM_152376 | UBXN10 | NM_020441 | CORO1B |
| NM_001077195 | ZNF436 | NM_145200 | CABP4 |
| NM_018202 | TMEM57 | NM_004055 | CAPN5 |
| NM_203401 | STMN1 | NM_021827 | CCDC81 |
| NM_024869 | GRRP1 | NM_001101321 | UBTFL2 |
| NR_003066 | SNORD85 | NM_004621 | TRPC6 |
| NM_001856 | COL16A1 | NM_004347 | CASP5 |
| NM_001042771 | LCK | NM_052889 | CARD16 |

TABLE 6-continued

List of genes with promoter γH2AX accumulation in SR or SEN cells.

| | | | |
|---|---|---|---|
| NM_206837 | C1orf102 | NM_152434 | CWF19L2 |
| NM_022756 | C1orf149 | NM_207430 | C11orf88 |
| NM_003819 | PABPC4 | NM_001082970 | C11orf57 |
| NM_148960 | CLDN19 | NM_012459 | TIMM8B |
| NM_173484 | KLF17 | NM_198971 | HINFP |
| NM_020365 | EIF2B3 | NM_012101 | TRIM29 |
| NM_000778 | CYP4A11 | NR_003125 | LOC85391 |
| NM_057176 | BSND | NM_001005188 | OR6X1 |
| NM_152377 | C1orf87 | NM_001004474 | OR10S1 |
| NM_032852 | ATG4C | NM_001005468 | OR8B2 |
| NM_203464 | AK3L1 | NM_001005196 | OR8B4 |
| NR_003042 | SNORD45C | NM_001005195 | OR8B12 |
| NM_005263 | GFI1 | NM_014987 | IGSF9B |
| NM_005665 | EVI5 | NM_002234 | KCNA5 |
| NM_002061 | GCLM | NM_001039916 | ZNF384 |
| NM_139156 | AMPD2 | NM_007273 | PHB2 |
| NM_147148 | GSTM4 | NM_000319 | PEX5 |
| NM_139053 | EPS8L3 | NM_015509 | NECAP1 |
| NM_004696 | SLC16A4 | NM_020661 | AICDA |
| NM_004185 | WNT2B | NM_016523 | KLRF1 |
| NM_006699 | MAN1A2 | NM_205852 | CLEC12B |
| NM_006099 | PIAS3 | NM_030817 | APOLD1 |
| NM_005399 | PRKAB2 | NM_001013698 | C12orf69 |
| NM_212551 | LYSMD1 | NM_001175 | ARHGDIB |
| NM_178431 | LCE3A | NM_032918 | RERG |
| NM_207308 | NUP210L | NM_004755 | PIK3C2G |
| NM_170782 | KCNN3 | NM_018638 | ETNK1 |
| NM_000157 | GBA | NM_001004329 | DBX2 |
| NM_032323 | TMEM79 | NM_015401 | HDAC7 |
| NM_001004476 | OR10K2 | NM_015086 | DDN |
| NM_001639 | APCS | NM_021044 | DHH |
| NM_015331 | NCSTN | NM_006337 | MCRS1 |
| NM_005149 | TBX19 | NM_000424 | KRT5 |
| NM_018186 | C1orf112 | NR_003716 | HOTAIR |
| NM_033418 | C1orf156 | NM_014212 | HOXC11 |
| NM_152663 | RALGPS2 | NM_014620 | HOXC4 |
| NM_173533 | TDRD5 | NR_003084 | HOXC5 |
| NM_052966 | FAM129A | NM_153693 | HOXC6 |
| NM_006469 | IVNS1ABP | NM_005584 | INHBC |
| NM_002113 | CFHR1 | NM_014770 | AGAP2 |
| NM_001994 | F13B | NM_002076 | GNS |
| NM_001024594 | C1orf53 | NM_020525 | IL22 |
| NM_004767 | GPR37L1 | NM_032735 | BEST3 |
| NM_002832 | PTPN7 | NM_005447 | RASSF9 |
| NM_201348 | PRELP | NM_001037671 | C12orf74 |
| NM_020439 | CAMK1G | NM_018838 | NDUFA12 |
| NM_052843 | OBSCN | NM_001093 | ACACB |
| NM_005999 | TSNAX | NM_024072 | DDX54 |
| NM_019090 | KIAA1383 | NM_194286 | KIAA1853 |
| NM_080738 | EDARADD | NM_001014336 | IL31 |
| NM_152666 | PLD5 | NM_019887 | DIABLO |
| NM_006642 | SDCCAG8 | NM_178314 | RILPL1 |
| NM_014812 | CEP170 | NR_002979 | SNORA49 |
| NM_031844 | HNRNPU | NM_175066 | DDX51 |
| NM_001004492 | OR2B11 | NM_001007537 | RP11-45B20.2 |
| NM_001005487 | OR13G1 | NM_002097 | GTF3A |
| NM_001005286 | OR6F1 | NM_145657 | GSX1 |
| NM_001005522 | OR2T8 | NM_178007 | STARD13 |
| NM_001004695 | OR2T33 | NM_005584 | MAB21L1 |
| NM_001004695 | OR2T10 | NM_001004127 | ALG11 |
| NM_001042521 | MGC13057 | NM_001005918 | ATP7B |
| NM_013388 | PREB | NM_001005501 | OR4K2 |
| NM_007266 | GPN1 | NM_001004480 | OR11H6 |
| NM_017910 | TRMT61B | NM_138376 | TTC5 |
| NM_005102 | FEZ2 | NM_017807 | OSGEP |
| NM_002759 | EIF2AK2 | NM_019852 | METTL3 |
| NM_148962 | OXER1 | NM_016609 | SLC22A17 |
| NM_001101330 | LOC728819 | NM_138460 | CMTM5 |
| NM_001042385 | PREPL | NM_006177 | NRL |
| NM_178313 | SPTBN1 | NM_006263 | PSME1 |
| NM_001039348 | EFEMP1 | NM_014169 | CHMP4A |
| NM_144709 | PUS10 | NM_203355 | CTAGE5 |
| NM_138458 | WDR92 | NM_020937 | FANCM |
| NM_006507 | REG1B | NM_018139 | C14orf104 |
| NM_017750 | RETSAT | NM_006832 | FERMT2 |
| NM_018271 | THNSL2 | NM_022571 | GPR135 |
| NM_020151 | STARD7 | NM_018373 | SYNJ2BP |
| NM_012214 | MGAT4A | NM_014982 | PCNX |
| NM_201557 | FHL2 | NM_001024674 | LIN52 |
| NM_032411 | C2orf40 | NM_004755 | RPS6KA5 |
| NM_032528 | ST6GAL2 | NM_000624 | SERPINA5 |
| NM_176825 | SULT1C2 | NM_152592 | C14orf49 |
| NM_000575 | IL1A | NR_003237 | SNORD113-9 |
| NM_025181 | SLC35F5 | NM_001311 | CRIP1 |
| NM_004805 | GLI2 | NM_144599 | NIPA1 |
| NM_004805 | POLR2D | NR_003317 | SNORD116-2 |
| NM_032357 | CCDC115 | NR_003298 | SNORD115-6 |
| NM_018328 | MBD5 | NR_003311 | SNORD115-17 |
| NM_004522 | KIF5C | NR_003314 | SNORD115-22 |
| NM_052917 | GALNT13 | NR_003495 | HBII-52-24 |
| NM_006593 | TBR1 | NR_003347 | SNORD115-32 |
| NM_004490 | GRB14 | NR_003498 | HBII-52-45 |
| NM_021193 | HOXD12 | NM_001042495 | SLC12A6 |
| NM_001077197 | PDE11A | NM_175741 | C15orf55 |
| NM_145739 | OSBPL6 | NM_207445 | C15orf54 |
| NM_000885 | ITGA4 | NM_001080791 | C15orf57 |
| NM_002500 | NEUROD1 | NM_015540 | RPAP1 |
| NM_005019 | PDE1A | NM_014994 | MAPKBP1 |
| NM_000090 | COL3A1 | NM_173088 | CAPN3 |
| NM_014585 | SLC40A1 | NM_016396 | CTDSPL2 |
| NM_144708 | ANKAR | NM_003758 | EIF3J |
| NM_022353 | OSGEPL1 | NM_152448 | C15orf43 |
| NM_016192 | TMEFF2 | NM_207581 | DUOXA2 |
| NM_138395 | MARS2 | NM_000338 | SLC12A1 |
| NM_014670 | BZW1 | NM_014701 | SECISBP2L |
| NM_006139 | CD28 | NM_153374 | LYSMD2 |
| NM_014929 | FASTKD2 | NM_001104554 | PAQR5 |
| NM_020989 | CRYGC | NM_201526 | ISLR |
| NM_000599 | IGFBP5 | NM_015162 | ACSBG1 |
| NM_001557 | IL8RB | NM_003847 | PEX11A |
| NM_005381 | NCL | NM_020211 | RGMA |
| NM_002601 | PDE6D | NM_152449 | LYSMD4 |
| NM_001631 | ALPI | NM_006453 | TBL3 |
| NM_017974 | ATG16L1 | NM_004209 | SYNGR3 |
| NR_003006 | SCARNA6 | NM_001103175 | CCDC64B |
| NM_021027 | UGT1A9 | NM_004220 | ZNF213 |
| NR_004428 | EGO | NM_016292 | TRAP1 |
| NM_015869 | PPARG | NM_004380 | CREBBP |
| NM_015199 | ANKRD28 | NM_001127448 | ABAT |
| NM_054110 | GALNTL2 | NM_002761 | PRM1 |
| NM_017897 | OXSM | NM_014153 | ZC3H7A |
| NM_001025068 | ARPP-21 | NM_015161 | ARL6IP1 |
| NM_175888 | ZNF620 | NM_001002911 | GPR139 |
| NM_016305 | SS18L2 | NM_003460 | ZP2 |
| NM_001295 | CCR1 | NM_013302 | EEF2K |
| NM_003965 | CCRL2 | NM_181078 | IL21R |
| NM_138615 | DHX30 | NM_024516 | C16orf53 |
| NM_005051 | QARS | NM_001114380 | ITGAL |
| NM_080865 | GPR62 | NR_002966 | SNORA30 |
| NM_018313 | PBRM1 | NM_033226 | ABCC12 |
| NM_015224 | C3orf63 | NM_001006610 | SIAH1 |
| NM_002841 | PTPRG | NM_144602 | C16orf78 |
| NM_182920 | ADAMTS9 | NM_031885 | BBS2 |
| NM_015123 | FRMD4B | NM_002990 | CCL22 |
| NM_001080393 | GLT8D4 | NR_002978 | SNORA46 |
| NM_001000448 | EPHA6 | NR_003079 | SNORD111 |
| NM_014648 | DZIP3 | NM_020995 | HPR |
| NM_005944 | CD200 | NM_001105663 | NUDT7 |
| NM_001085357 | BTLA | NM_021197 | WFDC1 |
| NM_173799 | TIGIT | NM_024735 | FBXO31 |
| NM_005694 | COX17 | NM_006822 | RAB40B |
| NM_016372 | GPR175 | NM_182705 | FAM101B |
| NM_007283 | MGLL | NM_022463 | NXN |
| NM_007354 | C3orf27 | NR_003073 | SNORD91B |
| NM_004164 | RBP2 | NM_018553 | C17orf85 |
| NM_152616 | TRIM42 | NM_198501 | SMTNL2 |
| NM_023915 | GPR87 | NM_001100812 | CXCL16 |
| NM_000902 | MME | NM_001024937 | MINK1 |
| NM_207015 | NAALADL2 | NM_019013 | FAM64A |
| NM_014693 | ECE2 | NM_003985 | TNK1 |
| NM_005787 | ALG3 | NM_152766 | C17orf61 |
| NM_004366 | CLCN2 | NM_032356 | LSMD1 |
| NM_006232 | POLR2H | NM_004217 | AURKB |
| NM_004443 | EPHB3 | NM_201432 | GAS7 |

TABLE 6-continued

List of genes with promoter γH2AX accumulation in SR or SEN cells.

| | | | |
|---|---|---|---|
| NM_018138 | TBCCD1 | NM_001372 | DNAH9 |
| NM_181573 | RFC4 | NM_016113 | TRPV2 |
| NM_001114980 | TP63 | NM_016078 | FAM18B |
| NM_178335 | CCDC50 | NM_016231 | NLK |
| NM_015274 | MAN2B2 | NM_015584 | POLDIP2 |
| NM_001105662 | USP17 | NM_144683 | DHRS13 |
| NM_031911 | C1QTNF7 | NM_005408 | CCL13 |
| NM_001775 | CD38 | NM_017559 | FNDC8 |
| NM_182592 | YIPF7 | NM_001104588 | SLFN11 |
| NM_173536 | GABRG1 | NM_032875 | FBXL20 |
| NM_006587 | CORIN | NM_199334 | THRA |
| NM_018475 | TMEM165 | NM_033187 | KRTAP4-3 |
| NM_002703 | PPAT | NM_033060 | KRTAP4-1 |
| NM_001012763 | GNRHR | NM_021013 | KRT34 |
| NM_016323 | HERC5 | NM_032387 | WNK4 |
| NM_145244 | DDIT4L | NM_001466 | FZD2 |
| NM_002006 | FGF2 | NM_152343 | C17orf46 |
| NM_007080 | LSM6 | NM_005486 | TOM1L1 |
| NM_183375 | ESSPL | NM_138363 | CCDC45 |
| NM_004564 | PET112L | NM_014960 | ARSG |
| NM_001013415 | FBXW7 | NM_139177 | SLC39A11 |
| NM_000824 | GLRB | NM_022036 | GPRCSC |
| NM_201592 | GPM6A | NM_178233 | OTOP3 |
| NM_138464 | LOC116349 | NR_004397 | SNORD1C |
| NM_004174 | SLC9A3 | NM_199167 | CLUL1 |
| NM_018140 | CEP72 | NM_005433 | YES1 |
| NM_007030 | TPPP | NM_173211 | TGIF1 |
| NM_182632 | SLC6A18 | NM_173464 | L3MBTL4 |
| NM_001001702 | FLJ33360 | NM_003826 | NAPG |
| NM_001369 | DNAH5 | NM_172241 | CTAGE1 |
| NR_003921 | PMCHL1 | NM_002647 | PIK3C3 |
| NM_178140 | PDZD2 | NR_002970 | SNORA37 |
| NM_001042625 | CAPSL | NM_005024 | SERPINB10 |
| NM_173489 | HEATR7B2 | NM_152721 | DOK6 |
| NM_001005473 | PLCXD3 | NM_006566 | CD226 |
| NM_175921 | C5orf51 | NM_130760 | MADCAM1 |
| NM_153361 | MGC42105 | NM_006830 | UQCR |
| NM_021147 | CCNO | NM_198532 | C19orf35 |
| NM_181523 | PIK3R1 | NM_024333 | FSD1 |
| NR_003014 | SNORA47 | NM_153359 | MGC24975 |
| NM_005779 | LHFPL2 | NM_174918 | C19orf59 |
| NM_005654 | NR2F1 | NR_002931 | CLEC4GP1 |
| NM_001002796 | MCTP1 | NM_012335 | MYO1F |
| NM_031952 | SPATA9 | NM_001004699 | OR2Z1 |
| NM_004772 | C5orf13 | NM_004461 | FARSA |
| NM_001077654 | TNFAIP8 | NM_080864 | RLN3 |
| NM_001048252 | CTXN3 | NM_032172 | C19orf44 |
| NM_002154 | HSPA4 | NM_145046 | CALR3 |
| NM_017415 | KLHL3 | NM_002248 | KCNN1 |
| NM_013983 | NRG2 | NM_025249 | KIAA1683 |
| NM_018931 | PCDHB11 | NM_001080409 | ZNF99 |
| NM_018929 | PCDHGC5 | NM_001105570 | NUDT19 |
| NM_001079812 | DIAPH1 | NM_019849 | SLC7A10 |
| NM_181677 | PPP2R2B | NM_021902 | FXYD1 |
| NM_054023 | SCGB3A2 | NM_207392 | KRTDAP |
| NM_133371 | MYOZ3 | NM_014364 | GAPDHS |
| NM_052860 | ZNF300 | NM_021232 | PRODH2 |
| NR_002168 | PPP1R2P3 | NM_144689 | ZNF420 |
| NM_021911 | GABRB2 | NM_003890 | FCGBP |
| NM_001129891 | LOC-100131897 | NM_198540 | B3GNT8 |
| NM_144769 | FOXI1 | NM_004363 | CEACAM5 |
| NM_001008220 | CPLX2 | NM_002780 | PSG4 |
| NM_016290 | UIMC1 | NM_001005376 | PLAUR |
| NM_197975 | BTNL3 | NM_001033719 | ZNF404 |
| NM_001085401 | C6orf201 | NM_001081563 | DMPK |
| NM_145649 | GCNT2 | NM_004943 | DMWD |
| NM_003529 | HIST1H3A | NM_001425 | EMP3 |
| NR_003504 | MGC22265 | NM_182575 | IZUMO1 |
| NM_003535 | HIST1H3J | NM_014475 | DHDH |
| NM_001509 | GPX5 | NM_001459 | FLT3LG |
| NM_006510 | TRIM27 | NM_001079907 | ZNF331 |
| NM_021904 | GABBR1 | NM_001037731 | DEFB116 |
| NM_001077511 | TCF19 | NM_153269 | C20orf96 |
| NM_001105564 | CCHCR1 | NM_080725 | SRXN1 |
| NM_005514 | HLA-B | NM_001083910 | SIRPB1 |
| NM_002904 | RDBP | NM_001039508 | SIRPG |
| NM_022107 | GPSM3 | NR_003684 | SNORD119 |
| NM_001077516 | SLC39A7 | NM_000490 | AVP |
| NM_002931 | RING1 | NM_198798 | ANKRD5 |
| NM_002263 | KIFC1 | NM_130811 | SNAP25 |
| NM_007104 | RPL10A | NM_001195 | BFSP1 |
| NM_032115 | KCNK16 | NM_002509 | NKX2-2 |
| NM_014623 | MEA1 | NM_178312 | GGTLC1 |
| NM_152882 | PTK7 | NM_024893 | C20orf39 |
| NM_170609 | CRISP1 | NR_004846 | LOC10013486 |
| NM_014464 | TINAG | NM_002110 | HCK |
| NM_019036 | HMGCLL1 | NM_031483 | ITCH |
| NM_183050 | BCKDHB | NM_006404 | PROCR |
| NR_003038 | SNHG5 | NM_080748 | ROMO1 |
| NM_018064 | AKIRIN2 | NM_213632 | C20orf132 |
| NM_002043 | GABRR2 | NR_003018 | SNORA71D |
| NM_015323 | KIAA0776 | NR_003239 | SNHG11 |
| NM_005190 | CCNC | NM_000022 | ADA |
| NM_014028 | OSTM1 | NM_198139 | SEMG1 |
| NM_006016 | CD164 | NM_001048226 | DBNDD2 |
| NM_153048 | FYN | NM_021035 | ZNFX1 |
| NM_002269 | KPNA5 | NM_080829 | FAM65C |
| NM_024581 | FAM184A | NM_173485 | TSHZ2 |
| NM_152730 | C6orf170 | NM_177980 | CDH26 |
| NM_001446 | FABP7 | NM_080606 | BHLHE23 |
| NM_030963 | RNF146 | NM_080823 | SRMS |
| NM_014702 | KIAA0408 | NM_017806 | LIME1 |
| NM_001079823 | LAMA2 | NM_003906 | MCM3AP |
| NM_005021 | ENPP3 | NM_058181 | C21orf57 |
| NM_053278 | TAAR8 | NM_021219 | JAM2 |
| NM_078488 | VNN2 | NM_181614 | KRTAP19-7 |
| NM_052831 | C6orf192 | NM_000454 | SOD1 |
| NM_005923 | MAP3K5 | NM_170737 | KCNJ15 |
| NM_001100166 | PHACTR2 | NM_004915 | ABCG1 |
| NM_001080951 | PLAGL1 | NM_198693 | KRTAP10-2 |
| NM_138785 | C6orf72 | NM_198690 | KRTAP10-9 |
| NM_017909 | RMND1 | NM_198692 | KRTAP10-11 |
| NM_001007466 | TULP4 | NM_197966 | BID |
| NM_020823 | TMEM181 | NM_002688 | 5-Sep |
| NM_003057 | SLC22A1 | NR_003714 | DKFZp434P21 |
| NM_021977 | SLC22A3 | NM_002430 | MN1 |
| NM_024492 | LPAL2 | NM_030641 | APOL6 |
| NM_000301 | PLG | NM_013356 | SLC16A8 |
| NM_031409 | CCR6 | NM_004810 | GRAP2 |
| NM_018974 | UNC93A | NM_024053 | CENPM |
| NM_144781 | PDCD2 | NM_058238 | WNT7B |
| NM_020144 | PAPOLB | NM_032257 | ZMYND12 |
| NM_032172 | USP2 | NM_002440 | MSH4 |
| NM_019005 | MIOS | NM_031936 | GPR61 |
| NM_019029 | CPVL | NM_001042552 | TATDN3 |
| NM_175887 | PRR15 | NM_007357 | COG2 |
| NM_032639 | PLEKHA8 | NM_001004698 | OR2W5 |
| NM_006774 | INMT | NM_175735 | LYG2 |
| NM_016489 | NT5C3 | NM_001106 | ACVR2B |
| NM_015283 | DPY19L1 | NM_007246 | KLHL2 |
| NM_002192 | INHBA | NM_016604 | JMJD1B |
| NM_015052 | HECW1 | NM_005565 | LCP2 |
| NM_001013398 | IGFBP3 | NM_014068 | PSORS1C1 |
| NR_003595 | MGC26484 | NM_004289 | NFE2L3 |
| NM_198570 | VWC2 | NM_018697 | LANCL2 |
| NM_030798 | WBSCR16 | NR_015374 | LOC401463 |
| NM_000927 | ABCB1 | NM_014637 | MTFR1 |
| NM_006980 | MTERF | NM_172060 | EYA1 |
| NM_001742 | CALCR | NM_199160 | LHX6 |
| NM_001099400 | SGCE | NM_012364 | OR1Q1 |
| NM_015395 | TECPR1 | NM_000216 | KAL1 |
| NM_015545 | PTCD1 | NM_001099857 | IKBKG |
| NM_000777 | CYP3A5 | NM_001002295 | GATA3 |
| NM_018275 | C7orf43 | NM_018294 | CWF19L1 |
| NM_013439 | PILRA | NM_003054 | SLC18A2 |
| NM_145030 | C7orf47 | NM_001128202 | C10orf122 |
| NM_022574 | GIGYF1 | NM_030754 | SAA2 |
| NM_021930 | RINT1 | NM_012194 | C11orf41 |
| NM_007356 | LAMB4 | NM_199418 | PRCP |
| NM_015723 | PNPLA8 | NM_145018 | C11orf32 |
| NM_182529 | THAP5 | NM_001009562 | LST-3TM12 |
| NM_001662 | ARF5 | NM_152590 | IFLTD1 |
| NM_012133 | COPG2 | NM_020782 | KLHDC5 |

TABLE 6-continued

List of genes with promoter γH2AX accumulation in SR or SEN cells.

| | | | |
|---|---|---|---|
| NM_012450 | SLC13A4 | NM_015319 | TENC1 |
| NM_003852 | TRIM24 | NM_201550 | LRRC10 |
| NM_130840 | ATP6V0A4 | NR_002801 | DKFZp686A1627 |
| NM_016019 | LUC7L2 | NM_016350 | NIN |
| NM_022750 | PARP12 | NM_001756 | SERPINA6 |
| NM_001080392 | KIAA1147 | NM_004918 | TCL1B |
| NM_018980 | TAS2R5 | NM_005926 | MFAP1 |
| NM_004668 | MGAM | NM_152450 | FAM81A |
| NR_002140 | OR6W1P | NM_002558 | P2RX1 |
| NM_001004685 | OR2F2 | NM_000442 | PECAM1 |
| NM_001001659 | OR2A14 | NM_001040185 | ZNF765 |
| NM_002889 | RARRES2 | | |
| NM_198285 | WDR86 | | |

Supplemental Table 7. Gene Ontology (GO) analysis of genes with promoter γH2AX accumulation in SEN cells.

| GO term | Name | P-value |
|---|---|---|
| GO: 0043170 | Biopolymer metabolic process | 2.83E−26 |
| GO: 0006139 | Nucleobase, nucleoside, nucleotide and nucleic acid metabolic process | 1.43E−21 |
| GO: 0007165 | Signal transduction | 4.91E−19 |
| GO: 0019538 | Protein metabolic process | 7.67E−17 |
| GO: 0019222 | Regulation of metabolic process | 1.25E−16 |
| GO: 0031323 | Regulation of cellular metabolic process | 3.47E−16 |
| GO: 0016070 | RNA metabolic process | 1.35E−14 |
| GO: 0010468 | Regulation of gene expression | 1.35E−14 |
| GO: 0044267 | Cellular protein metabolic process | 1.11E−13 |
| GO: 0044260 | Cellular macromolecule metabolic process | 1.14E−13 |
| GO: 0019219 | Regulation of nucleobase, nucleoside, nucleotide and nucleic acid metabolic process | 3.05E−13 |
| GO: 0006350 | transcription | 3.16E−13 |
| GO: 0045449 | Regulation of transcription | 1.15E−12 |
| GO: 0048522 | Positive regulation of cellular process | 1.78E−11 |
| GO: 0048518 | Positive regulation of biological process | 3.02E−11 |
| GO: 0032774 | RNA biosynthetic process | 5.03E−11 |
| GO: 0006351 | Transcription DNA dependent | 5.85E−11 |
| GO: 0007275 | Multicellular organismal development | 6.55E−11 |
| GO: 0051234 | Establishment of localization | 1.16E−10 |
| GO: 0048519 | Negative regulation of biological process | 3.29E−10 |
| GO: 0006355 | Regulation of transcription, DNA dependent | 3.35E−10 |
| GO: 0006810 | transport | 3.75E−10 |
| GO: 0048731 | System development | 5.44E−10 |
| GO: 0051252 | Regulation of RNA metabolic process | 6.32E−10 |
| GO: 0048523 | Negative regulation of cellular process | 9.86E−10 |
| GO: 0048856 | Anatomical structure development | 1.25E−09 |
| GO: 0051641 | Cellular localization | 4.91E−09 |
| GO: 0035556 | Intracellular signaling cascade | 1.35E−08 |
| GO: 0022607 | Cellular component assembly | 2.00E−08 |
| GO: 0051649 | Establishment of cellular localization | 2.15E−08 |
| GO: 0006366 | Transcription from RNA polymerase II promoter | 2.38E−08 |
| GO: 0007166 | Cell surface receptor linked signal transduction | 2.81E−08 |
| GO: 0009966 | Regulation of signal transduction | 4.65E−08 |
| GO: 0006464 | Protein modification process | 5.35E−08 |
| GO: 0006996 | Organelle organization and biogenesis | 7.78E−08 |
| GO: 0065003 | Macromolecular complex assembly | 9.38E−08 |
| GO: 0007049 | Cell cycle | 1.23E−07 |
| GO: 0009058 | Biosynthetic process | 3.04E−07 |
| GO: 0046907 | Intracellular transport | 4.31E−07 |
| GO: 0048468 | Cell development | 5.91E−07 |
| GO: | Macromolecule localization | 6.70E−07 |
| GO 0008283 | Cell proliferation | 8.91E−07 |
| GO: 0045934 | Negative regulation of nucleobase, nucleoside, nucleotide and nucleic acid metabolic process | 1.07E−06 |
| GO: 0009892 | Negative regulation of metabolic process | 1.99E−06 |
| GO: 0031324 | Negative regulation of cellular metabolic process | 2.53E−06 |
| GO: 0006950 | Response to stress | 2.98E−06 |
| GO: 0006357 | Regulation of transcription from RNA polymerase II promoter | 3.77E−06 |
| GO: 0008104 | Protein localization | 4.31E−06 |
| GO: 0016481 | Negative regulation of transcription | 7.94E−06 |

TABLE 8

Cell Cycle (GO: 0007049) and Cell Proliferation (GO: 0008283) genes with promoter γH2AX accumulation in SEN cells.

| GO term | Gene symbol | Gene name | Function* |
|---|---|---|---|
| GO: 0007049 | INHBA | inhibin, beta A (activin A, activin AB alpha polypeptide) | The inhibin beta A subunit joins the alpha subunit to form a pituitary FSH secretion inhibitor. Inhibin has been shown to regulate gonadal stromal cell proliferation negatively and to have tumor-suppressor activity. |
| GO: 0007049 | GFI1 | growth factor independent 1 | This gene encodes a nuclear zinc finger protein that functions as a transcriptional repressor. This protein plays a role in diverse developmental contexts, including hematopoiesis and oncogenesis. It functions as part of a complex along with other cofactors to control histone modifications that lead to silencing of the target gene promoters. |
| GO: 0007049 GO: 0008283 | CD28 | CD28 molecule | CD28 costimulation is essential for CD4 (MIM 186940)-positive T-cell proliferation, survival, interleukin-2 (IL2; MIM147680) production, and T-helper type-2 (Th2) development. |

TABLE 8-continued

Cell Cycle (GO: 0007049) and Cell Proliferation (GO: 0008283) genes with promoter γH2AX accumulation in SEN cells.

| GO term | Gene symbol | Gene name | Function* |
|---|---|---|---|
| GO: 0007049 | STMN1 | stathmin 1/oncoprotein 18 | This gene belongs to the stathmin family of genes. It encodes a ubiquitous cytosolic phosphoprotein proposed to function as an intracellular relay integrating regulatory signals of the cellular environment. The encoded protein is involved in the regulation of the microtubule filament system by destabilizing microtubules. |
| GO: 0007049 GO: 0008283 | CUL2 | cullin 2 | Core component of multiple cullin-RING-based ECS (ElonginB/C-CUL2/5-SOCS-box protein) E3 ubiquitin-protein ligase complexes, which mediate the ubiquitination of target proteins. May serve as a rigid scaffold in the complex and may contribute to catalysis through positioning of the substrate and the ubiquitin-conjugating enzyme. |
| GO: 0007049 | GAS7 | growth arrest-specific 7 | Growth arrest-specific 7 is expressed primarily in terminally differentiated brain cells and predominantly in mature cerebellar Purkinje neurons. GAS7 plays a putative role in neuronal development. |
| GO: 0007049 | HERC5 | hect domain and RLD 5 | This gene is a member of the HERC family of ubiquitin ligases and encodes a protein with a HECT domain and five RCC1 repeats. Pro-inflammatory cytokines upregulate expression of this gene in endothelial cells. The protein localizes to the cytoplasm and perinuclear region and functions as an interferon-induced E3 protein ligase that mediates ISGylation of protein targets. |
| GO: 0008283 | GLI2 | GLI-Kruppel family member GLI2 | This gene encodes a protein which belongs to the C2H2-type zinc finger protein subclass of the Gli family. Gli family zinc finger proteins are mediators of Sonic hedgehog (Shh) signaling and they are implicated as potent oncogenes in the embryonal carcinoma cell. The protein encoded by this gene localizes to the cytoplasm and activates patched Drosophila homolog (PTCH) gene expression. It is also thought to play a role during embryogenesis. The encoded protein is associated with several phenotypes - Greig cephalopolysyndactyly syndrome, Pallister-Hall syndrome, preaxial polydactyly type IV, postaxial polydactyly types A1 and B. |
| GO: 0008283 | TCF19 | transcription factor 19 (SC1) | Potential trans-activating factor that could play an important role in the transcription of genes required for the later stages of cell cycle progression. |
| GO: 0008283 | CD40LG | CD40 ligand (TNF superfamily, member 5, hyper-IgM syndrome) | The protein encoded by this gene is expressed on the surface of T cells. It regulates B cell function by engaging CD40 on the B cell surface. A defect in this gene results in an inability to undergo immunoglobulin class switch and is associated with hyper-IgM syndrome. |
| GO: 0008283 | CALCA | calcitonin/calcitonin-related polypeptide, alpha | This gene encodes the peptide hormones calcitonin, calcitonin gene-related peptide and katacalcin by tissue-specific alternative RNA splicing of the gene transcripts and cleavage of inactive precursor proteins. Calcitonin is involved in calcium regulation and acts to regulate phosphorus metabolism. |
| GO: 0008283 | TNFSF15 | tumor necrosis factor (ligand) superfamily, member 15 | The protein encoded by this gene is a cytokine that belongs to the tumor necrosis factor (TNF) ligand family. This cytokine is a ligand for receptor TNFRSF25 and decoy receptor TNFRSF21/DR6. It can activate NF-kappaB and MAP kinases, and acts as an autocrine factor to induce apoptosis in endothelial cells. This cytokine |

TABLE 8-continued

Cell Cycle (GO: 0007049) and Cell Proliferation (GO: 0008283) genes with promoter γH2AX accumulation in SEN cells.

| GO term | Gene symbol | Gene name | Function* |
|---|---|---|---|
| | | | is also found to inhibit endothelial cell proliferation, and thus may function as an angiogenesis inhibitor. |
| GO: 0008283 | ADRA2A | adrenergic, alpha-2A-, receptor | Alpha-2-adrenergic receptors are members of the G protein-coupled receptor superfamily. These receptors have a critical role in regulating neurotransmitter release from sympathetic nerves and from adrenergic neurons in the central nervous system. |
| GO: 0008283 | IL8RB | interleukin 8 receptor, beta | The protein encoded by this gene is a member of the G-protein-coupled receptor family. This protein is a receptor for interleukin 8 (IL8). It binds to IL8 with high affinity, and transduces the signal through a G-protein activated second messenger system. This receptor also binds to chemokine (C—X—C motif) ligand 1 (CXCL1/MGSA), a protein with melanoma growth stimulating activity, and has been shown to be a major component required for serum-dependent melanoma cell growth. This receptor mediates neutrophil migration to sites of inflammation. |
| GO: 0008283 | TNFSF8 | tumor necrosis factor (ligand) superfamily, member 8 | The protein encoded by this gene is a cytokine that belongs to the tumor necrosis factor (TNF) ligand family. This cytokine is a ligand for TNFRSF8/CD30, which is a cell surface antigen and a marker for Hodgkin lymphoma and related hematologic malignancies. This cytokine was shown to enhance cell proliferation of some lymphoma cell lines, while to induce cell death and reduce cell proliferation of other lymphoma cell lines. |
| GO: 0008283 | FLT3LG | fms-related tyrosine kinase 3 ligand | Stimulates the proliferation of early hematopoietic cells. Synergizes well with a number of other colony stimulating factors and interleukins. |
| GO: 0008283 | CD164 | CD164 molecule, sialomucin | CD164 is a type I integral transmembrane sialomucin that functions as an adhesion receptor. |
| GO: 0008283 | PLG | plasminogen | The protein encoded by this gene is a secreted blood zymogen that is activated by proteolysis and converted to plasmin and angiostatin. |
| GO: 0008283 | FABP7 | fatty acid binding protein 7, brain | The protein encoded by this gene is a brain fatty acid binding protein. |
| GO: 0008283 | EVI5 | ecotropic viral integration site 5 | Functions as a regulator of cell cycle progression by stabilizing the FBXO5 protein and promoting cyclin-A accumulation during interphase. May play a role in cytokinesis. |
| GO: 0008283 | IL1A | interleukin 1, alpha | The protein encoded by this gene is a member of the interleukin 1 cytokine family. This cytokine is a pleiotropic cytokine involved in various immune responses, inflammatory processes, and hematopoiesis. |
| GO: 0008283 | RERG | RAS-like, estrogen-regulated, growth inhibitor | RERG, a member of the RAS superfamily of GTPases, inhibits cell proliferation and tumor formation. |
| GO: 0008283 | EIF2AK2 | eukaryotic translation initiation factor 2-alpha kinase 2 | Following activation by double-stranded RNA in the presence of ATP, the kinase becomes autophosphorylated and can catalyze the phosphorylation of the translation initiation factor EIF2S1, which leads to an inhibition of the initiation of protein synthesis. |
| GO: 0008283 | EMP3 | epithelial membrane protein 3 | Probably involved in cell proliferation and cell-cell interactions. |
| GO: 0008283 | CRIP1 | cysteine-rich protein 1 (intestinal) | Cysteine-rich intestinal protein (CRIP) belongs to the LIM/double zinc finger protein family. CRIP may be involved in intestinal zinc transport. |

TABLE 8-continued

Cell Cycle (GO: 0007049) and Cell Proliferation (GO: 0008283) genes with promoter γH2AX accumulation in SEN cells.

| GO term | Gene symbol | Gene name | Function* |
|---|---|---|---|
| GO: 0008283 | REG1B | regenerating islet-derived 1 beta (pancreatic stone protein, pancreatic thread protein) | This gene encodes a protein secreted by the exocrine pancreas that is highly similar to the REG1A protein. |

SUPPLEMENTAL TABLE 9

RT-PCR and qPCR primers

| Primer | Sequence | | SEQ ID NO |
|---|---|---|---|
| MIRm | Forward: | 5'-AGGATTTAAAGCTCTCTCTGCAGG-3' | 14 |
|  | Reverse: | 5'-ATGACTGAACTCTAAGATAAAGATCACAGC-3' | 15 |
| Alu | Forward: | 5'-AGACAATCCTGGCCAACTTGG-3' | 16 |
|  | Reverse: | 5'-GCATTCCTGGACTGTGATGTGG-3' | 17 |
| AluJb | Forward: | 5'-TGTGTGCCTGTAGTCCTAGCTACTAGG-3' | 18 |
|  | Reverse: | 5'-TTCAGGTTAGAGCTCTGAAGTCACG-3' | 19 |
| AluSx | Forward: | 5'-TCTGCTCGGGAGGCTGAGG-3' | 20 |
|  | Reverse: | 5'-CCACCCACGAAGAATACATTTGC-3' | 21 |
| RPL13A | Forward: | 5'-AAGGTGTTTGACGGCATCC-3' | 22 |
|  | Reverse: | 5'-GTTCTTCTCGGCCTGTTTCC-3' | 23 |
| Oct4 | Forward: | 5'-CTTCGCAAGCCCTCATTTC-3' | 24 |
|  | Reverse: | 5'-GAGAAGGCGAAATCCGAAG-3' | 25 |
| Nanog | Forward: | 5'-CCCCAGCCTTTACTCTTCCT-3' | 26 |
|  | Reverse: | 5'-CTGGTTGCTCCAGGTTGAAT-3' | 27 |
| b-actin | Forward: | 5'-CAACTCCATCATGAAGTGTGAC-3' | 28 |
|  | Reverse: | 5'-GCCATGCCAATCTCATCTTG-3' | 29 |

Example 3

Protein Complex Assembled on piRNA Derived from Alu Retrotransposal Transcript Indicates Putative Participation of retroRNA in the Cell Cycle, DNA Repair and Chromatin Assembly Recent genome wide analysis indicates that thousands of short Interspersed elements (SINEs) are present in constrained non-exonic elements (Lowe and Haussler, PNAS 2007) suggesting that these repeated retrotransposal elements might play a unique and yet to be discovered role in shaping and/or specializing the genomic landscape as well as gene regulation during mammalian evolution. Here we report LC-MS/MS RNA-affinity complex isolation using piRNA derived from Alu retrotransposal RNA. Our data indicate the role of piAlu RNAs in DNA repair, cell cycle, and chromatin regulation.

Figure 21:
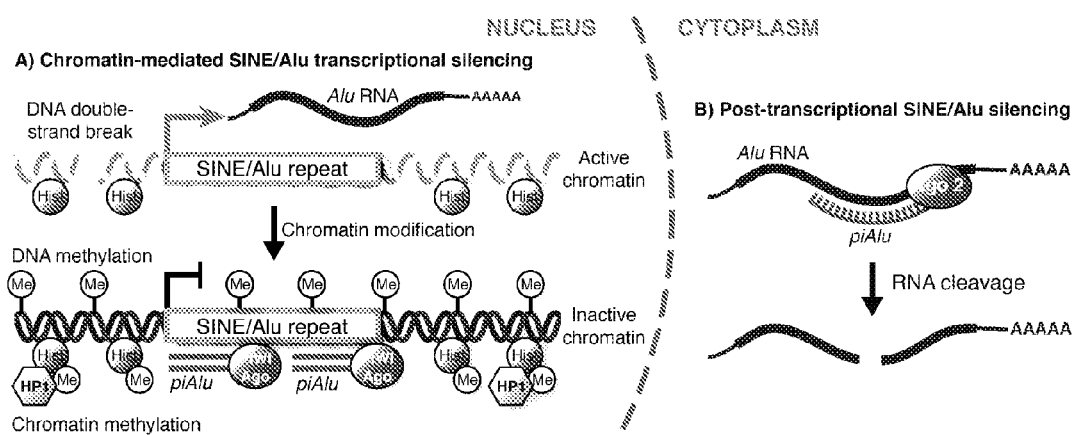
FIG. 21, panels A (left) and B (right), illustrate alternative models of Alu shRNA action. Panel A: shRNA against Alu forms a hairpin shRNA, which directs either nuclear PIWI or Dicer machinery to the genomic SINE/Alu repeat location, initiating transcriptional silencing via heterochromatinization involving both DNA methylation and histone modification. Panel B: shRNA against Alu activates the PTGS Dicer-dependent Ago2 pathway, leading to the cytoplasmic degradation of unprocessed Alu RNA transcripts.

Recently, we have demonstrated that a majority of the repairable DNA damage sites in self-renewing human adult stem cells is associated with the retrotransposal portion of the genome, in particular, with Alu retrotransposons (Wang et al. (2011) *Cell Cycle* 10: 3016-3030). Our group has shown that the up-regulation of transcriptional activity from Alu can be triggered by genotoxic stress-induced damage and can be recorded in human retinal pigment epithelium (RPE) and human adult stem cells (Id.) upon in-vivo and ex-vivo aging, respectively. Evidence indicates that increased accumulation of Alu RNA within cells is directly linked to Dicer-1 deficiency (Kaneko et al. (2011) *Nature* 471: 325-330), suggesting that Alu transcript accumulation might not necessarily be due to increased transcriptional activity from Alu retrotransposons, but rather may result from the absence of concomitant Alu transcript processing, leading to cytotoxicity. Our recent data indicates that the accumulation of unprocessed Alu transcripts triggers chromatin deterioration, loss of DNA repair in pericentromeric areas eliciting the persistent DNA damage response and, ultimately, cellular senescence. Our data also indicate that human adult stem cells stably expressing an shRNA against Alu transcripts override cellular senescence and reinstate their DNA repair capacity (Wang et al. (2011) *Cell Cycle* 10: 3016-3030), suggesting that RNA interference (RNAi) machinery is involved in these events. This data also suggests two equally possible mechanisms through which an shRNA against Alu might mediate the observed function: 1) through the PTGS Dicer-dependent pathway via the cytoplasmic degradation of unprocessed Alu RNA or 2) through facilitating transcriptional silencing by recruiting either the Dicer-dependent or Piwi-dependent arms of the RNAi pathway to act directly on the chromatin as shown in FIG. 21. Both of these pathways are plausible and either could depend on the assembly of single or multiple protein complexes that are capable of cross-talk with DNA-damagesensing/repair and chromatin and/or centromeric maintenance pathways. Interestingly, a recent study indicated that transcripts generated from telomere-repeat-encoded RNA (TERRA) interact with heterochromatin protein 1 (HP1), trimethlyated histone H3 Lysine 9 (H3K9me3), core components of the Shelterin complex as well as members of the DNA-damage-sensing pathway (Deng et al. (2009) *Mol. Cell*, 35: 403-413).

Similarly we believe that the portion of Alu RNA, which is functionally relevant to overriding the senescent phenotype of hADSCs (Wang et al. (2011) *Cell Cycle* 10: 3016-3030), can mediate a broad array of downstream effects associated with retrotransposal transcription. Since the cytoplasmic role of Alu RNA in the assembly of signal recognition particles has been previously reported (He et al. (1994) *J. Cell Sci.*, 107(Pt 4): 903-912), we have focused our efforts specifically on the elucidation of nuclear complexes assembled on Alu RNA. Using an unbiased RNA affinity assay coupled with mass spectrometry, we provide evidence for the composition of molecular complexes assembled on processed Alu RNA transcripts. Our data suggests the pathways and molecular processes through which processed intermediates of Alu RNA may participate in a multitude of nuclear regulations within human adult stem cells.

Results

Alu RNA and its Homology to Human PIWI-Interacting RNA (piRNA)

Figure 22A:
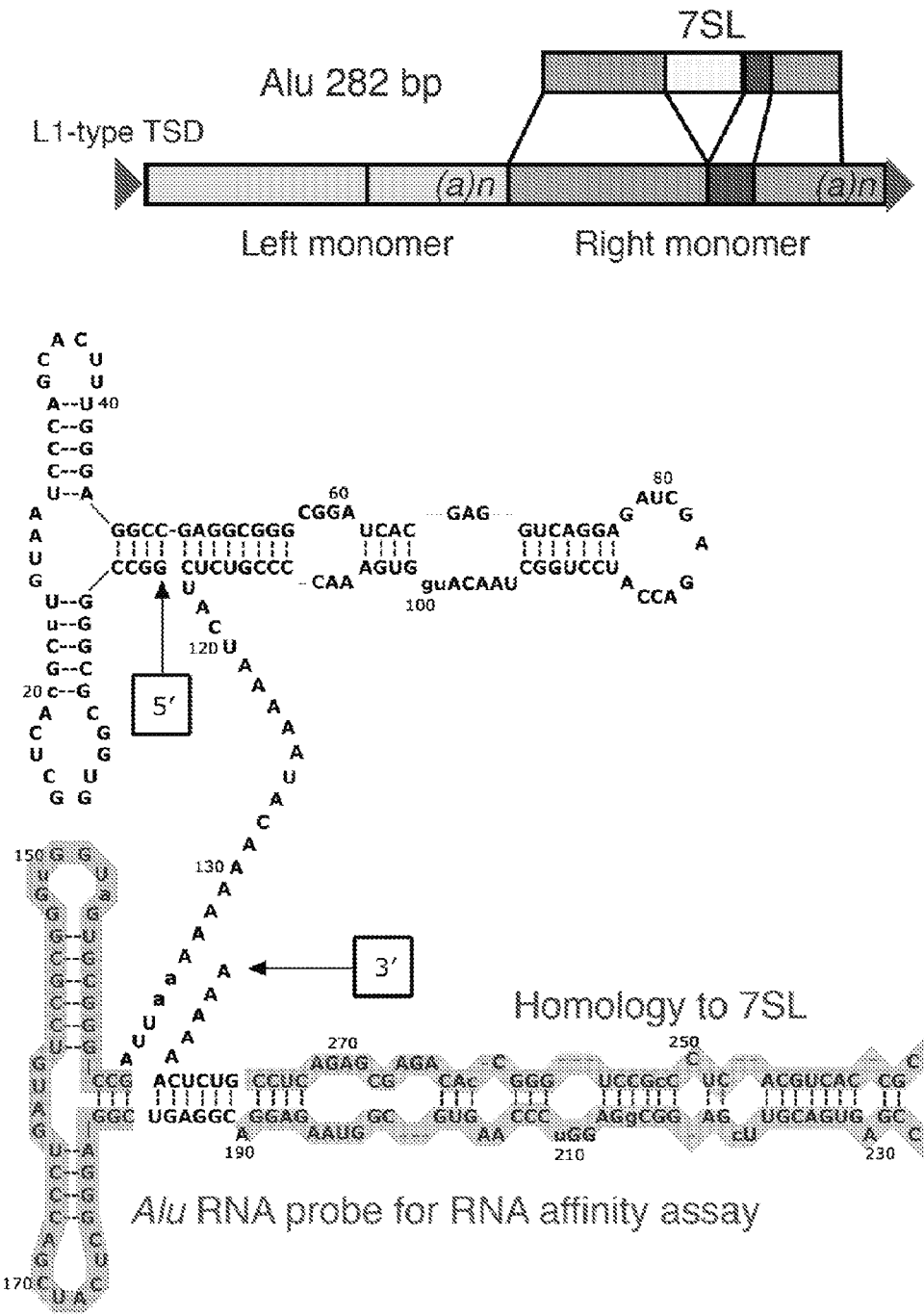
FIG. 22A (top) shows a representation of 7SL-conserved region within Alu full-length sequence.
Figure 22B:
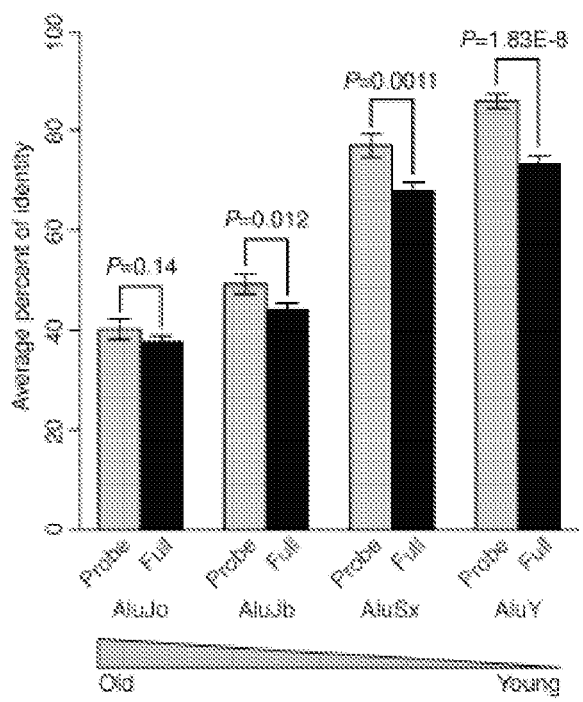
FIG. 22B shows sequence conservation of the Alu shRNA sequence compared to the rest of the element. Average percent identity levels among dispersed repeated element copies are compared for the shRNA Alu sequence regions versus other Alu sequence regions across four Alu subfamilies. Significance values for the differences are shown for each comparison.
Figure 22D:
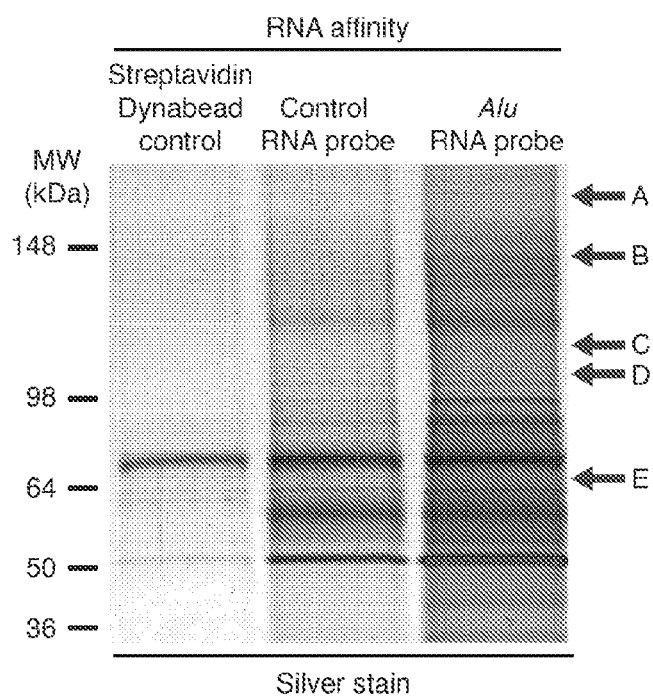
FIG. 22D shows silver-stained denaturing 4-12% NuPAGE Novex 4-12% Bis-Tris gel loaded with RNA affinity assay precipitants, with excised bands labeled A-E.

Previously it was reported that Alu RNA participates in the cytoplasmic assembly of the signal recognition particle (SRP) in mammalian cells (He et al. (1994) *J. Cell Sci.*, 107(Pt 4): 903-912). The mammalian SRP is composed of a single RNA, the 7SL RNA, and six proteins (Walter and Blobel (1981) *J. Cell Biol.*, 91: 557-561). SRP9 and SRP14 bind to the 5' end of the RNA (Alu-domain), which functions in translational arrest (Siegel and Walter (1988) *Trends Biochem. Sci.*, 13: 314-316; Siegel and Walter (1986) *Nature* 320:81-84). However, this functional shRNA reported in Wang et al. (2011) *Cell Cycle* 10: 3016-3030 has no complementarity to 7SL RNA. In addition, the region of Alu that corresponds to the shRNA is more highly conserved between repeats than the rest of the element (FIG. 22B). This conservation is consistent with the ability of the shRNA to effectively knock down transcription from multiple repeated Alu copies, including members of distinct subfamilies. Taken together, these data illuminate the functional relevance of the Alu shRNA sequence analyzed here, and indicate that this sequence may represent a processed Alu RNA species that functions in the nucleus. We queried the Alu shRNA sequence analyzed here against previously reported PIWI interacting RNA (piRNA) sequences previously reported in Girard et al. (2006) *Nature* 442: 199-202.

The exact sequence of the shRNA was identified as a PIWI-interacting RNA, pir-52207 and pir-57460 (Id.) (NCBI accession #DQ585095 (tgcctgtaat cccagctact caggaggctg, (SEQ ID NO:30)), and is referred to herein as piALU. This suggests that Alu RNA is subjected to processing by an analog of the human PIWI complex, the molecular function of which is unknown, but nevertheless indicates that this piAlu transcript, derived from processed Alu transcripts, might function in the nucleus.

Alu RNA Interaction with Nuclear Factors

We attempted to obtain a comprehensive list of proteins that interact, both directly and indirectly, with piALU. For this purpose, we engaged an unbiased RNA-affinity assay using synthetic biotinylated RNA oligos encompassing Alu nucleotides 140-183, shown in FIG. 22B, with nuclear extracts from self-renewing human adult stem cells. This portion of Alu is conserved among different types of Alu retrotransposons: AluSx, AluJb, AluJo, and AluY (FIG. 22B).

Figure 22C:
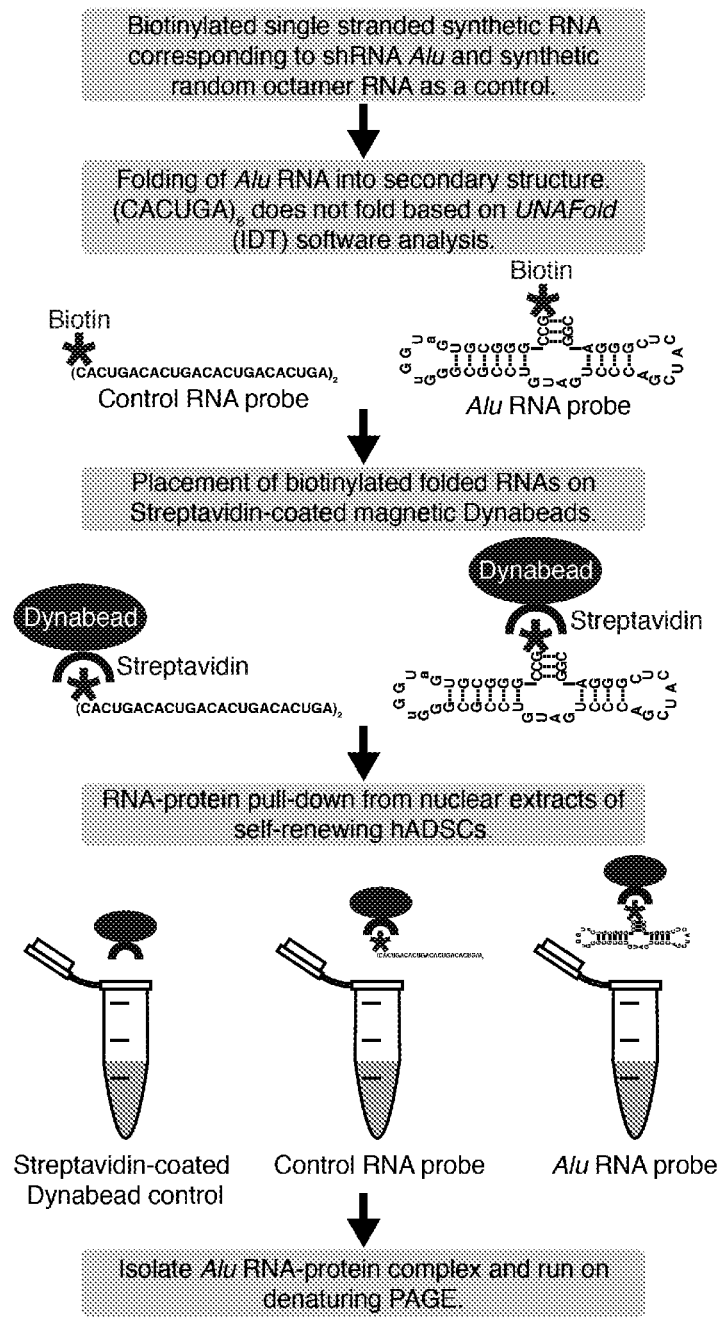
FIG. 22C shows a step-by-step schematic representation of unbiased RNA affinity assay.

Our piALU RNA affinity assay was combined with a comprehensive LC-MS/MS (Liquid Chromatography-Electrospray Tandem Mass Spectrometry) analysis of interacting proteins. Since a nuclear RNA surveillance pathway exists that protects from transcriptional noise, we added a control hexanucleotide repeat control RNA "bait", described in Materials and Methods, to avoid non-sequence-specific interactions. The experimental procedure was previously reported by Deng et al. (2009) *Mol. Cell*, 35: 403-413 and is outlined in FIG. 22B. Our comparative analysis of RNA-protein binding by PAGE depicted the presence of multiple piALU probe-specific bands (FIG. 22C) that were excised for LC-MS/MS identification. An exhaustive list of the proteins identified is shown in Supplementary Table 1.

Figure 23:
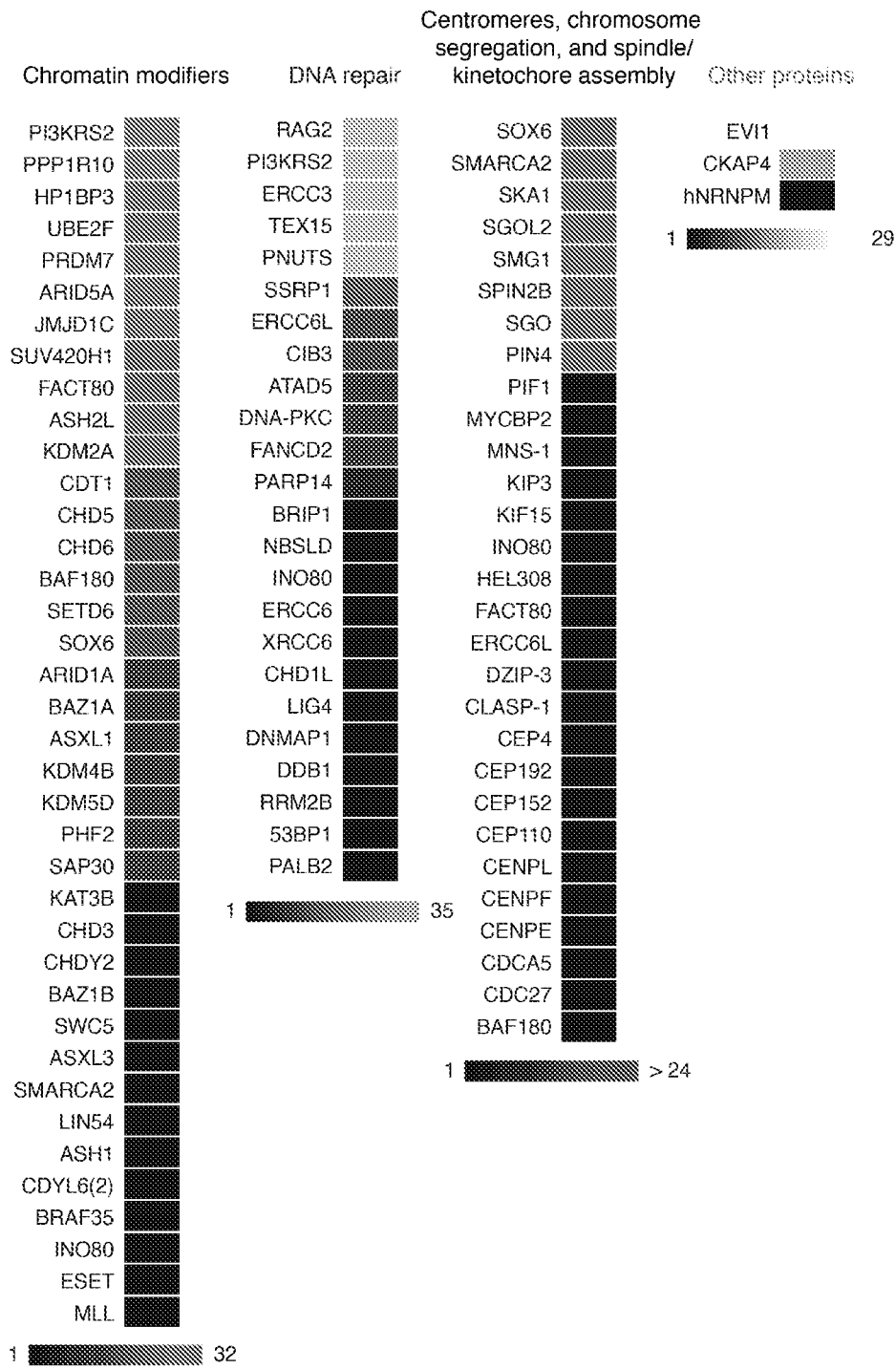
FIG. 23 shows a brightness-coded representation of abundance of members in major functional categories. Most abundant proteins within each group are depicted with the brightest color, fading to black for those with an abundance of only 1.

Alu RNA Interactions with Major Chromatin Modifiers, DNA Repair Complexes, Centromeric Chromatin/Kinetochore Assembly Factors and Transcriptional Factors Our mass spectrometry analysis of unbiased piALU RNA-affinity precipitants revealed the presence four major protein categories such as chromatin modifiers, DNA repair complexes, centromeric chromatin/kinetochore assembly and transcriptional factors (FIG. 23). The abundance of each component is represented as a color gradient fading from true hues to black for singly represented peptides. Similar to protein interactions with telomeric RNA repeats (TERRA) (Id.), piALU binding proteins include DNA damage response proteins DNA-PKC, PARP and hnRNPM, suggesting that piALU RNA may be integral to DNA repair complexes.

Figure 24A:
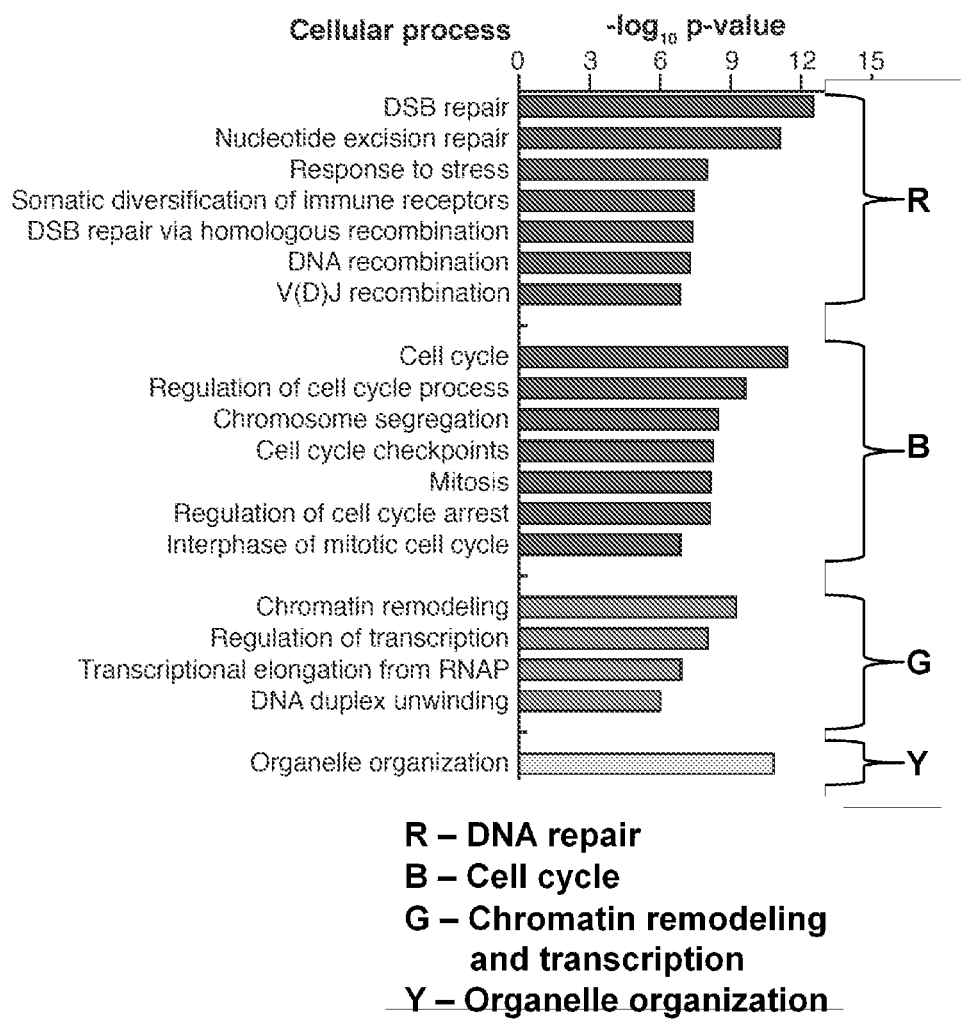
FIG. 24A shows confidence levels for the involvement of isolated complex proteins in various cellular processes, represented Gene Ontology (GO) terms as a $-\log_{10}$(p-value), using p-values calculated by DAVID software. 24B shows confidence levels for the presence of isolated complex proteins in various cellular components, represented as a $-\log_{10}$(p-value), as calculated using DAVID software.

To assess the relevance of piALU RNA to biological processes, we applied a Gene Ontology (GO) (The Gene Ontology Consortium (2010) *Nucleic Acids Res.*, 38(suppl 1): D331-D335; Barrell et al. (2009) *Nucleic Acids Res* 37:D396-D403) analysis to the list of interacting proteins. All together, 19 cellular processes were significantly ($3.12 \times 10^{-13} \leq P \leq 1.5 \times 10^{-3}$) enriched among Alu-interacting proteins including: DNA repair, organelle organization, cell cycle, chromatin remodeling and transcription (FIG. 24A). These broader categories encompass nucleotide excision repair, DSB repair via homologous recombination, DNA recombination, V(D)J recombination, response to stress, chromosome segregation, cell cycle check-points, regulation of cell cycle checkpoint arrest, interphase of mitotic cycle and mitosis (FIG. 24A). Complexes related to DNA duplex unwinding, regulation of transcription and transcriptional elongation from RNA polymerase II promoters were also significantly enriched.

Several nuclear proteins were associated with multiple GO terms (n=12) designated to cellular components including the centrosome, nucleoplasm, kinetochore, spindle, microtubule cytoskeleton, centromeric and telomeric regions of chromosomes, as well as the cohesin and DNA-directed RNA polymerase complexes (FIG. 24A).

These data suggest a possible role for Alu RNA in the regulation of chromatin organization in centromeric/pericentromeric regions as well as DNA repair processes and the transcriptional regulation of genes. All of these cellular processes have been proven to be indispensable to the regulation of cell cycle progression.

Protein-Protein Interaction Network of the piALU RNA-Affinity Complex

Figure 24B:
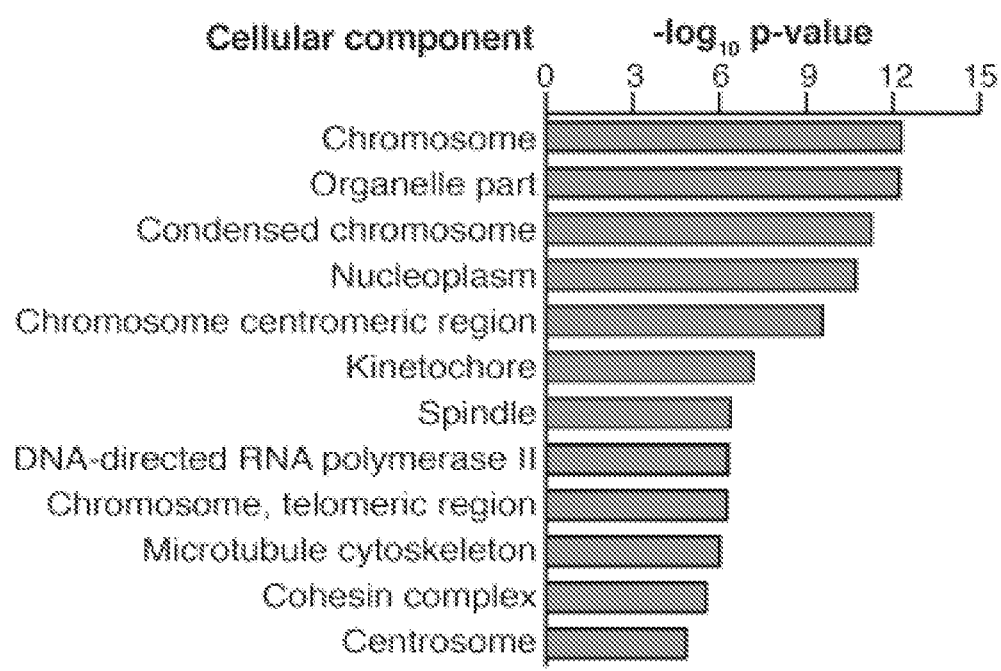
FIG. 24C shows an interaction web of isolated proteins produced in STRING 9.0 software. Thicker lines represent higher confidence (experimentally derived) interactions while dotted lines represent inferred (lower confidence) interactions.
Figure 24C:
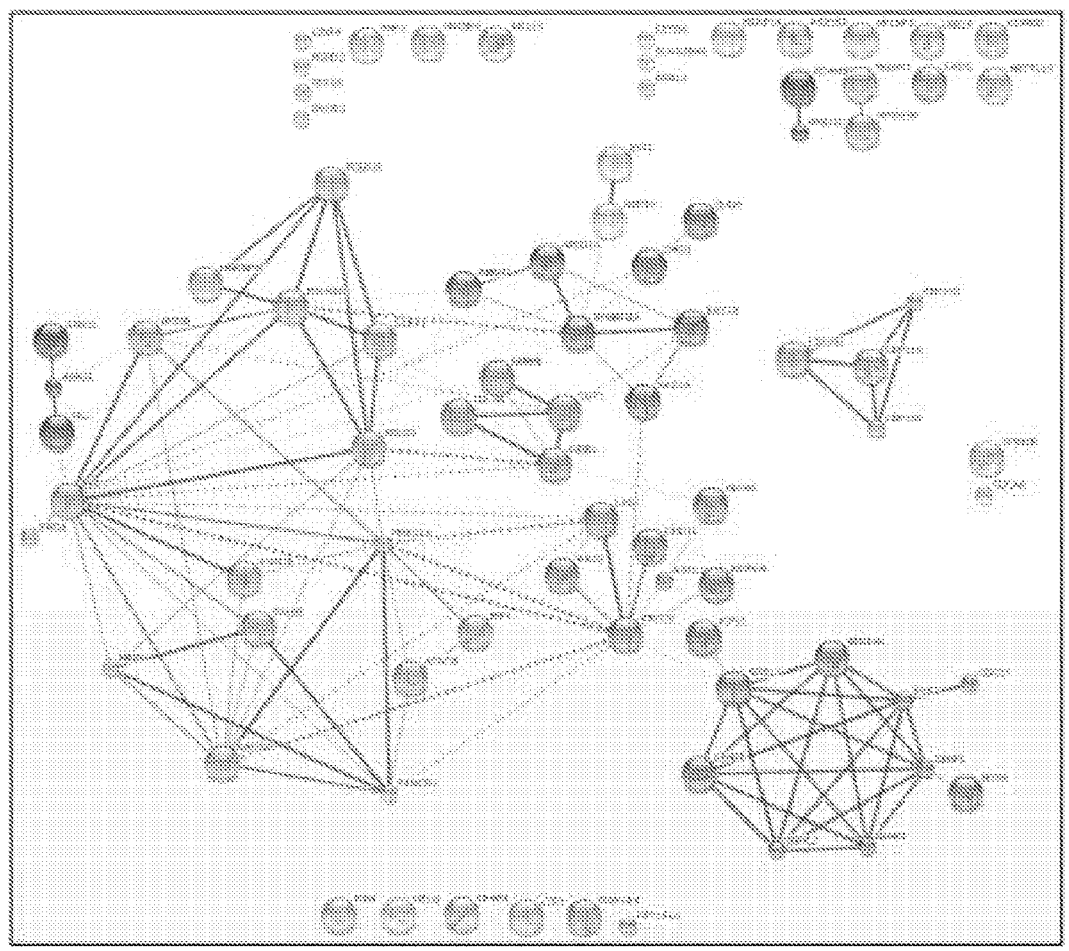

Understanding the cellular function(s) of an isolated protein complex(es) is facilitated by the ability to correctly uncover and annotate all functional interactions among LC-MS/MS identified proteins. To build a protein-protein interaction network among piALU RNA-affinity isolated proteins, we used the online database Search Tool for the Retrieval of Interacting Genes (STRING) version 9.0. This tool provides uniquely comprehensive coverage and ease of access to both experimental and predicted interaction information (Szklarczyk et al. (2011) *Nucleic Acids Res.,* 39: D561-D568). The STRING model of our LC-MS/MS data of nuclear piALU RNA-protein interactions is shown in FIG. 24B. Only high confidence level (experimentally reported) evidence of interactions/associations in curated databases in conjunction with the Markov clustering algorithm (MCL) were used to build the network and assign proteins into families (stronger associations are represented by thicker lines in FIG. 24B and FIG. 25) (Enright et al. (2002) *Nucleic Acids Res.,* 30: 1575-1584). Strikingly, 9 out of the 64 Alu RNA interacting partners are involved in chromosome segregation and include SGOL1, SGOL2, CENPE, CENPF, MRE11A, CDCA5 with 4 more (PBRM1, CENPL, CDC27 and MAP3K8) directly linked to mitosis, while the addition of PIN4 and KIF15 depicts a complex protein network regulating spindle assembly. This observation suggests that piALU transcripts might form a molecular connection between centromere cohesion and microtubule dynamics at the kinetochore. The previously reported loss of outer kinetochore proteins CENP-E and CENP-F upon knockdown of Sgo (Salic et al. (2004) *Cell* 118: 567-578), together with our recent observation that the accumulation of unprocessed Alu RNA blocks the recruitment the cohesin complex to centromeres and triggers cellular senescence in adult stem cells (Wang et al. (2011) *Cell Cycle* 10: 3016-3030), suggests that Alu RNA in its processed form may be an RNA adaptor in spindle microtubule dynamics.

Figure 25:
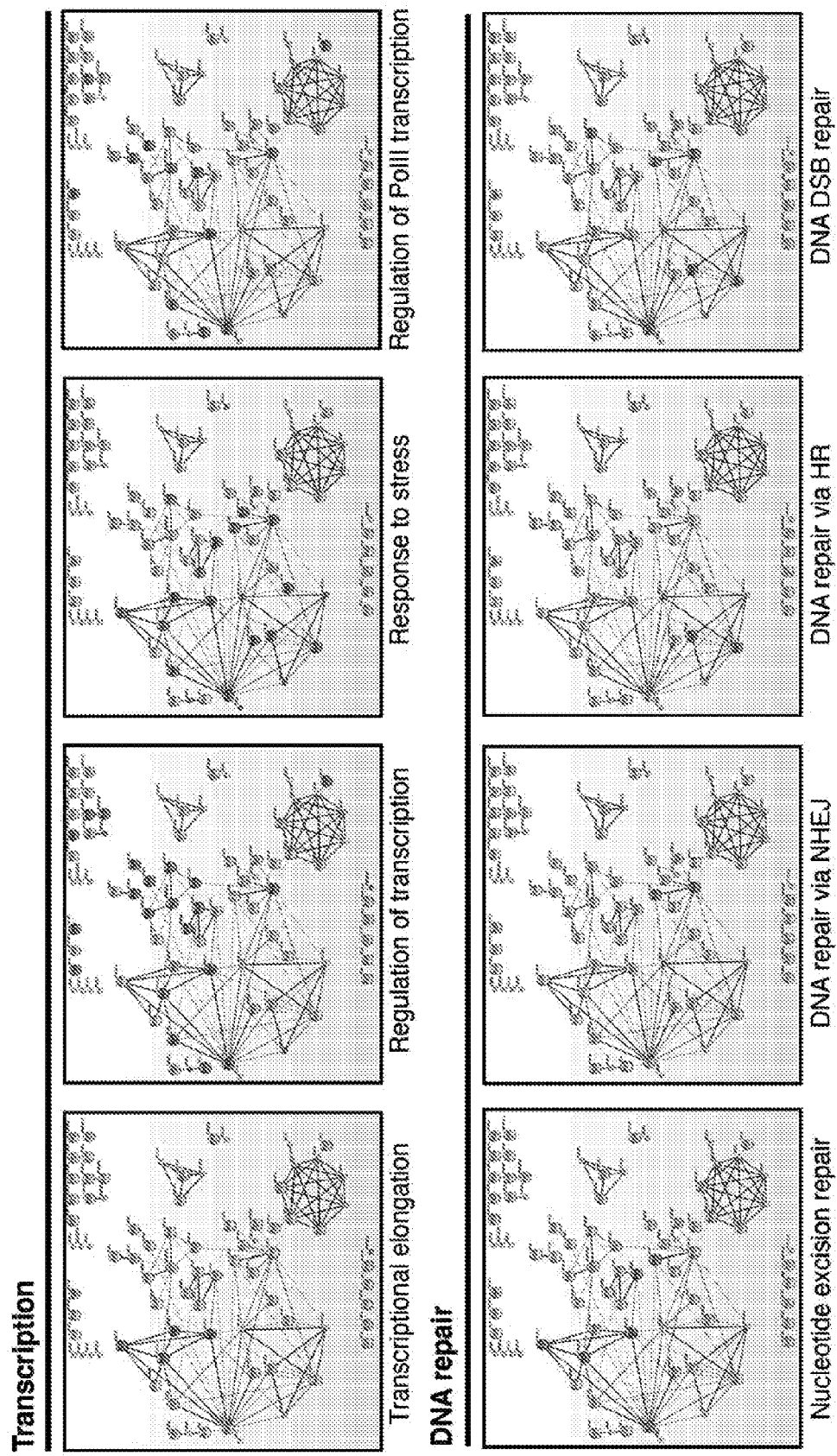
FIG. 25 shows a representation of protein complex using Gene Ontology (GO) terms in String 9.0. Each specific cellular process is grouped into one of the following 5 categories: transcription, DNA repair, chromatin modifications, cell cycle regulation, and others.

Data shown in FIG. 25 also indicate that 34 out of the 64 analyzed piALU RNA interacting partners are somehow involved in the regulation of the cell cycle. The presence of centrosomal proteins CEP192, CEP110, CEP152 and CEP135 points to the intriguing possibility that Alu RNA intermediates play a role in this cellular organelle and together with CUL4A, GMNN and CTD1 (FIG. 25), may participate in regulating interphase and the G/M phase transition.

Excitingly, piALU RNA also pulled down components of the nucleotide excision repair (ERCC3, DDB1, MRE11A), non-homologous end joining (LIG4, XRCC6) and homologous recombination (PALB2, RAD50) DNA repair pathways as well as the BAZ1B protein, suggesting a putative role for piALU RNA in double-strand break repair. The assembly of the DNA damage repair complexes described herein may be a critical event in adult stem cell aging (Kaneko et al. (2011) *Nature* 471: 325-330; Wang et al. (2011) *Cell Cycle* 10: 3016-3030). It is tempting to speculate that a lack of proper assembly/function of these complexes together or separately with chromatin remodeling components (CHD6, SMARCA2, BAZ1A, ARID1A, 1N080, ASXL1 and KDM2A) may explain the gradual loss of DNA damage repair triggering the persistent DNA damage response and cellular senescence (Rodier et al. (2009) *Nat. Cell Biol.,* 11: 973-979; Rodier et al. (2011) *J. Cell Sci.,* 124: 68-81).

Discussion

A recent genome-wide ChIP-RNA sequencing project revealed that over a third of all known large conserved ncRNAs can be pulled down with just four different chromatin modifying proteins (Khalil et al. (2009) *Proc. Natl. Acad. Sci. USA,* 106: 11667-11672), suggesting that most long ncRNAs associate with chromatin modifiers. The piALU RNA interactome presented herein also includes a variety of chromatin modifiers, possibly elucidating another level of complexity in ncRNA/chromatin modifier protein complexes that depend on the presence of a shorter, processed form of the Alu transcript. The full-length sequence of Alu RNA can form four distinct stem-loop structures, which may act as individual nucleating centers for the formation of distinct RNA-protein complexes (FIG. 22). Only one of the four stem-loops was used as a synthetic RNA "bait", since it encompasses the previously reported human PIWI-interacting RNA (Girard et al. (2006) *Nature* 442: 199-202) and is capable of nucleating protein complex(es) that are directly or indirectly responsible for reinstating self-renewal to senescent adult stem cells (Wang et al. (2011) *Cell Cycle* 10: 3016-3030).

Indeed, in accord with our previous data, the observed interactions supports the relevance of these nuclear piALU RNA-protein complex(es) to cell cycle control, DNA repair, chromatin maintenance, and the function of centromeres/pericentromeres in human adult stem cells. This data is currently lacking functional assessment, but nevertheless may hold the key to understanding how retrotransposal transcription/processing regulates human adult stem cell aging and senescence ex-vivo.

The data reported in this Example points to interesting possible involvements of short RNA species derived from Alu retrotransposons in the regulation of cell cycle control, RNA-pol II transcription and the maintenance of chromatin architecture. It appears that this participation is intimately linked to DNA repair processes.

Material and Methods

Human ADSC Isolation and Expansion

Human adipose derived stem cells (hADSCs) were isolated from human subcutaneous white adipose tissue collected during liposuction procedures. The lipoaspirate was suspended in Hank's Buffered Salt Solution (HBSS), 3.5% Bovine Serum Albumin (BSA), 1% Collagenase, type II (Sigma) in 1:3 w/v ratio and shaken at 37° C. for 50 min. The cells were filtered through a 70 µm mesh cell strainer (BD Falcon #352350), treated with Red Blood Cell Lysis buffer (150 mM $NH_4Cl$, 10 mM $KHCO_3$, 0.1 mM EDTA, pH 7.3), and expanded ex-vivo in DMEM/F12 complete medium (DMEM/F12, 10% FBS, 100 U/ml penicillin, 100 µg/ml streptomycin, 2.5 µg/ml amphotericin B; Invitrogen) in 10% $CO_2$ at 37° C. and passaged at 80% confluency, changing medium every 72-96 hours.

Nuclear Chromatin Extraction

Nuclear and cytoplasmic proteins were isolated from self-renewing hADSCs using the ProteoJET™ Cytoplasmic and Nuclear Protein Extraction Kit (Fermentas #K0311), according to the manufacturer's protocol.

RNA Secondary Structure Folding

5' biotinylated single stranded synthetic RNA probes corresponding to the 140-183 nucleotide region of full-length Alu, (5'-/Bio/-GCC GGG CG UG AUG GUG GGC GCC UGU AGU CCC AGC UAC UCG GGA GGC-3', SEQ ID NO:31) as well as a synthetic random octamer repeat 5'-/Bio/-$(CACUGA)_8$ (SEQ ID NO:32) as a linear control, were purchased from Integrated DNA Technologies (IDT). These oligos were purified via RNase-Free HPLC. 8 µg of each oligo were heated in a PCR tube with 15 ml of 2× Folding Buffer (40 mM HEPES pH 7.9, 0.4 mM EDTA, 2 M NaCl) and 9 ml DEPC water with 50 U/ml SUPERase-In RNAse inhibitor (Ambion, #AM2694). The RNA oligonucleotides were heated to 78° C. to induce a linear conformation, then the reaction temperature was reduced to and held at 54° C. to accommodate and retain desired secondary structure formation (mimicking the secondary stem-loop structure of the full length RNA), based on calculations by UNAFold software (IDT). The control repeat RNA 5'-/Bio/-(CACUGA)$_8$ (SEQ ID NO:32) is not capable of forming a secondary structure.

Protein Pulldown (Unbiased RNA Affinity Assay)

100 µl of streptavidin-coated Dynabeads (Dynabeads M-270 Streptavidin, #65306) per reaction were washed three times in 1×D150 buffer (20 mM HEPES pH 7.9, 20% glycerol, 0.2 mM EDTA, 150 mM NaCl, 0.05% NP-40, 1 mM PMSF, 10 mM β-mercaptoethanol) before a final high-salt wash with 1× Folding Buffer (containing 1 M NaCl). 30 µl of folded RNA solution was added to each reaction tube and incubated at RT for 15 min, then washed twice with 100 µl of low-salt Folding Buffer (containing 150 mM NaCl). Bead-bound RNA probes were incubated for 30 min at RT with nuclear extracts from self-renewing hADSCs, along with 1 µl of 0.01M PMSF and 3 µl SUPERase-In. After incubation, the Dynabeads were washed five times in 1×D150 buffer, leaving only directly and indirectly interacting partners attached to the beads. As a negative control, nuclear extracts were also incubated with Dynabeads alone to control for any interaction between nuclear molecules and the beads themselves.

Denaturing PAGE Analysis of Affinity Purified Protein Complexes.

XT Sample buffer 12 (BioRad #161-0791) and XT Reducing Agent (BioRad #161-0792) were added to 10 µg of protein. After denaturation for 5 min at 100° C., protein samples were loaded into a precast 4-12% NuPAGE Novex 4-12% Bis-Tris gel (Invitrogen, #NP0321BOX), and run out at 150 V for two hours. Gels were stained with ProteoSilver Plus Silver Stain Kit (Sigma, #Prot-SIL1). A SeeBlue Plus2 Pre-Stained Standard (Invitrogen, cat #LC5925) was used for visualization and approximation of molecular weights of protein samples. Bands unique to the Alu probe lane were excised and the analyzed by LC-MS/MS for protein content.

Sample Preparation for MS Analysis

The gel samples were first rinsed with acetonitrile, then reduced using DTT followed by alkylation using iodoacetamide. We rinsed gel samples with three alternating washes of 50 mM ammonium bicarbonate and acetonitrile, then cooled and resuspended each gel slice in trypsin (5.5 µg/mL in 50 mM ammonium bicarbonate/10% acetonitrile) and incubated at 37° C. for 24 hours for digestion of proteins. We extracted peptides with one rinse of 50 mM ammonium bicarbonate/10% acetonitrile followed by one rinse of 50% acetonitrile/0.1% formic acid, and prepared samples for mass spectrometry by lyophilization and rehydration in 20 µL 5% acetonitrile/0.2% formic acid.

Identification of Protein Partners by Mass Spectrometry
High Resolution LC-MS/MS High resolution LC-MS/MS analysis was carried out on an LTQ-Orbitrap XL mass spectrometer (Thermo Fisher Scientific) as previously described ENREF 45 (Lopez et al. (2011) *J. Proteome Res.*, 10: 133-142). Briefly, we loaded excised and digested samples into 96-well plates for mass spectrometry analysis on a LTQ-Orbitrap XL (Thermo Fisher Scientific) instrument as previously described (Lopez et al. (2011) *J. Proteome Res.*, 10: 133-142). We injected 10 µL of each re-constituted sample using a Thermo Scientific EASY-nLC Autosampler. Reverse phase chromatographic separations were carried out using Hypersil GOLD™ C18™ 3 µm media packed into a fused silica 75 µm inner diameter, 20 cm long column running at 250 nL/min. A gradient was produced using 5-40% acetonitrile, 0.2% formic acid over 150 minutes. The LTQ-Orbitrap was run in a top 8 configuration at 60K resolution for a full scan, with monoisotopic precursor selection enabled, and +1, and unassigned charge state rejected. The analysis on the LTQ-Orbitrap instrument was carried out with CID fragmentation.

LC-MS/MS Data Analysis and Protein Identification

LC-MS/MS data analysis, protein identification and peak-list generation were performed using Proteome Discoverer (Thermo Fisher Scientific) algorithm incorporating the SEQUEST® search engine and Percolator™ (Kall et al. (2007) *Nat, Methods*, 4: 923-925) as previously described (Lopez et al. (2011) *J. Proteome Res.*, 10: 133-142). MS/MS data were searched using 10 ppm mass accuracy on precursor m/z and a 0.5 Da window on fragment ions. Fully enzymatic tryptic searches with up to three missed cleavage sites were allowed. Oxidized methionines were searched as a variable modification and alkylated cysteines were searched as a fixed modification. Human databases were downloaded from NCBI and supplemented with common contaminants. We filtered peptides for each charge state to a false discovery rate (FDR) of 1%, and then grouped peptides into proteins using Occam's razor logic.

Protein Interaction Network Analysis

All highly represented members of the RNA-protein complex which were isolated were analyzed using STRING 9.0 software (Szklarczyk et al. (2011) *Nucleic Acids Res.*, 39: D561-D568). The obtained interaction network was subsequently analyzed with BINGO2 plug-in to determine statistical enrichments for 14 Gene Ontology (GO) categories (The Gene Ontology Consortium (2010) *Nucleic Acids Res.*, 38(suppl 1) D331-D335; Barrell et al. (2009) *Nucleic Acids Res* 37:D396-D403).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing or restoring or maintaining proliferative capacity in a mammalian mesenchymal stem cell in vitro, said method comprising:
reducing the level or activity of SINE/Alu retrotransposon transcripts in said mammalian mesenchymal stem cell in an amount sufficient to induce or restore or maintain proliferative capacity to said mammalian mesenchymal stem cell, wherein said reducing the level or activity of SINE/Alu transcripts comprises introducing into said mammalian mesenchymal stem cell a construct that comprises or encodes a small interfering RNA (siRNA) molecule or a piRNA molecule that targets a 7SL conserved region of a SINE/Alu retrotransposon transcript.

2. The method of claim 1, wherein said method comprises:
restoring proliferative capacity to said mammalian mesenchymal stem cell when said mesenchymal mammalian stem cell has reduced or lost proliferative capacity; or
inducing proliferative capacity to said mammalian stem cell when said mesenchymal mammalian stem cell lacks such capacity; or
maintaining proliferative capacity in said mammalian mesenchymal stem cell.

3. The method of claim 1, wherein said mammalian mesenchymal stem cell shows one or more indicators of senescence.

4. The method of claim 1, wherein said small interfering RNA comprises a molecule selected from the group consisting of a single strand RNA, a paired double strand RNA (dsRNA), and a small hairpin RNA (shRNA).

5. The method of claim 1, wherein said construct comprises a nucleic acid comprising the sequence 5'-GAT CCC CCC ACC ACG CCC GGC TAA TTT TCA AGA GAA ATT AGC CGG GCG TGG TGG TTT TTG GAA A-3' (SEQ ID NO:10).

6. The method of claim 1, wherein said construct produces a stable down regulation of SINE/Alu transcripts.

7. The method of claim 1, wherein said construct comprises a vector.

8. The method of claim 7, wherein the vector is a plasmid vector; or a viral vector.

9. The method of claim 8, wherein the vector is a viral vector selected from the group consisting of a retroviral vector, a lentiviral vector, an adenoviral vector, and an adeno-associated vector.

10. The method of claim 1, wherein said introducing is achieved via transformation, transduction, transfection, or infection.

11. The method of claim 1, wherein said introducing is achieved via a lipid or liposome.

12. The method of claim 1, wherein said method does not comprise targeted upregulation of a Oct3/4, and/or Sox2, and/or Klf4, and/or c-myc, or providing one or more heterologous constructs in said cell encoding Oct3/4, and/or Sox2, and/or Klf4, and/or c-myc.

13. The method of claim 1, wherein said construct comprises or encodes a PIWI RNA (piRNA).

* * * * *

SEQUENCE LISTING

```
<160> NUMBER OF SEQ ID NOS: 31

<210> SEQ ID NO 1
<211> LENGTH: 289
<212> TYPE: RNA
<213> ORGANISM: Homo sapiens

<400> SEQUENCE: 1
ggccgggcgc gguggcucac gcuuguaauc ccagcacuuu gggaggccga ggcgggcgga    60
```

```
ucacgagguc aggagaucga gaccauccug gcuaacaugg ugaaacccg ucucuacuaa    120 aaauacaaaa aaaauuagcc gggcgugaug ugggcgccu guagucccag cuacucggga    180
ggcugaggca ggagaauggc gugaacccug gaggcggagc uugcagugag ccgagauugc    240
gccacugcac ucccgccugg gccacagagc gagacuccgu ucaaaaaa                289

<210> SEQ ID NO 2
<211> LENGTH: 289
<212> TYPE: RNA
<213> ORGANISM: Homo sapiens

<400> SEQUENCE: 2
ggccgggcgc gguggcucac gcuuguaauc ccagcacuuu gggaggccga ggcgggcgga    60
ucacgagguc aggagaucga gaccauccug gcuaacaugg ugaaacccg ucucuacuaa    120 aaauacaaaa aaaauuagcc gggcgugaug ugggcgccu guagucccag cuacucggga    180
ggcugaggca ggagaauggc gugaacccug gaggcggagc uugcagugag ccgagauugc    240
gccacugcac ucccgccugg gccacagagc gagacuccgu ucaaaaaa                289

<210> SEQ ID NO 3
<211> LENGTH: 21
<212> TYPE: RNA
<213> ORGANISM: Artificial
<220> FEATURE:
<223> OTHER INFORMATION: Synthetic siRNA.
<220> FEATURE:
<221> NAME/KEY: misc_feature
<222> LOCATION: (3)..(21)
<223> OTHER INFORMATION: n is a, c, g, or u

<400> SEQUENCE: 3
aannnnnnnn nnnnnnnnnn n                                              21

<210> SEQ ID NO 4
<211> LENGTH: 23
<212> TYPE: RNA
<213> ORGANISM: Artificial
<220> FEATURE:
<223> OTHER INFORMATION: Synthetic siRNA.
<220> FEATURE:
<221> NAME/KEY: misc_feature
<222> LOCATION: (3)..(23)
<223> OTHER INFORMATION: n is a, c, g, or u

<400> SEQUENCE: 4
aannnnnnnn nnnnnnnnnn nnn                                            23

<210> SEQ ID NO 5
<211> LENGTH: 23
<212> TYPE: RNA
<213> ORGANISM: Artificial
<220> FEATURE:
<223> OTHER INFORMATION: Synthetic siRNA.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (3)..(23)
<223> OTHER INFORMATION: n is a, c, g, or u

<400> SEQUENCE: 5
nannnnnnnn nnnnnnnnnn nnn                                            23
```

```
<210> SEQ ID NO 6
<211> LENGTH: 19
<212> TYPE: RNA
<213> ORGANISM: Artificial
<220> FEATURE:
<223> OTHER INFORMATION: Synthetic siRNA.
<220> FEATURE:
<221> NAME/KEY: misc_feature
<222> LOCATION: (1)..(19)
<223> OTHER INFORMATION: n is a, c, g, or u

<400> SEQUENCE: 6
nnnnnnnnnn nnnnnnnnn                                              19

<210> SEQ ID NO 7
<211> LENGTH: 21
<212> TYPE: RNA
<213> ORGANISM: Artificial
<220> FEATURE:
<223> OTHER INFORMATION: Synthetic siRNA.
<220> FEATURE:
<221> NAME/KEY: misc_feature
<222> LOCATION: (1)..(21)
<223> OTHER INFORMATION: n is a, c, g, or u

<400> SEQUENCE: 7
nnnnnnnnnn nnnnnnnnnn n                                           21

<210> SEQ ID NO 8
<211> LENGTH: 23
<212> TYPE: RNA
<213> ORGANISM: Artificial
<220> FEATURE:
<223> OTHER INFORMATION: Synthetic siRNA.
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (22)..(23)
<223> OTHER INFORMATION: n is a, c, g, or u

<400> SEQUENCE: 8
narnnnnnnn nnnnnnnnnn ynn                                         23

<210> SEQ ID NO 9
<211> LENGTH: 9
<212> TYPE: RNA
<213> ORGANISM: Artificial
<220> FEATURE:
<223> OTHER INFORMATION: Synthetic or theroetical RNA motif.

<400> SEQUENCE: 9 agggaaccc                                                          9

<210> SEQ ID NO 10
<211> LENGTH: 64
<212> TYPE: DNA
<213> ORGANISM: Artificial
<220> FEATURE:
<223> OTHER INFORMATION: Synthetic oligonucleotide.

<400> SEQUENCE: 10
gatcccccca ccacgcccgg ctaatttca agagaaatta gccgggcgtg gtggttttg   60
```

```
gaaa                                                                    64

<210> SEQ ID NO 11
<211> LENGTH: 64
<212> TYPE: DNA
<213> ORGANISM: Artificial
<220> FEATURE:
<223> OTHER INFORMATION: Synthetic oligonucleotide.

<400> SEQUENCE: 11 gatcccccc gggttcaagc gattctttca agagaagaat cgcttgaacc cgggttttg       60 gaaa                                                                    64

<210> SEQ ID NO 12
<211> LENGTH: 20
<212> TYPE: DNA
<213> ORGANISM: Artificial
<220> FEATURE:
<223> OTHER INFORMATION: Synthetic oligonucleotide probe.

<400> SEQUENCE: 12
ccaccacgcc cggctaattt                                                   20

<210> SEQ ID NO 13
<211> LENGTH: 65
<212> TYPE: DNA
<213> ORGANISM: Artificial
<220> FEATURE:
<223> OTHER INFORMATION: Synthetic oligonucleotide probe.

<400> SEQUENCE: 13
cgcgcgccac cacgcccggc taattttgt atttttagta gagacggggt ttcaccatgt       60
tggcc                                                                   65

<210> SEQ ID NO 14
<211> LENGTH: 24
<212> TYPE: DNA
<213> ORGANISM: Artificial
<220> FEATURE:
<223> OTHER INFORMATION: Synthetic PCR primer.

<400> SEQUENCE: 14
aggatttaaa gctctctctg cagg                                              24

<210> SEQ ID NO 15
<211> LENGTH: 30
<212> TYPE: DNA
<213> ORGANISM: artificial
<220> FEATURE:
<223> OTHER INFORMATION: Synthetic PCR primer.

<400> SEQUENCE: 15
atgactgaac tctaagataa agatcacagc                                        30

<210> SEQ ID NO 16
<211> LENGTH: 21
<212> TYPE: DNA
<213> ORGANISM: artificial
<220> FEATURE:
<223> OTHER INFORMATION: Synthetic PCR primer.

<400> SEQUENCE: 16
agacaatcct ggccaacttg g                                                 21
```

```
<210> SEQ ID NO 17
<211> LENGTH: 22
<212> TYPE: DNA
<213> ORGANISM: artificial
<220> FEATURE:
<223> OTHER INFORMATION: Synthetic PCR primer.

<400> SEQUENCE: 17
gcattcctgg actgtgatgt gg                                              22

<210> SEQ ID NO 18
<211> LENGTH: 52
<212> TYPE: DNA
<213> ORGANISM: artificial
<220> FEATURE:
<223> OTHER INFORMATION: Synthetic PCR primer.

<400> SEQUENCE: 18
tgtgtgcctg tagtcctagc tactaggttc aggttagagc tctgaagtca cg            52

<210> SEQ ID NO 19
<211> LENGTH: 19
<212> TYPE: DNA
<213> ORGANISM: artificial
<220> FEATURE:
<223> OTHER INFORMATION: Synthetic PCR primer.

<400> SEQUENCE: 19
tctgctcggg aggctgagg                                                  19

<210> SEQ ID NO 20
<211> LENGTH: 23
<212> TYPE: DNA
<213> ORGANISM: artificial
<220> FEATURE:
<223> OTHER INFORMATION: Synthetic PCR primer.

<400> SEQUENCE: 20
ccacccacga agaatacatt tgc                                             23

<210> SEQ ID NO 21
<211> LENGTH: 19
<212> TYPE: DNA
<213> ORGANISM: artificial
<220> FEATURE:
<223> OTHER INFORMATION: Synthetic PCR primer.

<400> SEQUENCE: 21
aaggtgtttg acggcatcc                                                  19

<210> SEQ ID NO 22
<211> LENGTH: 20
<212> TYPE: DNA
<213> ORGANISM: artificial
<220> FEATURE:
<223> OTHER INFORMATION: Synthetic PCR primer.

<400> SEQUENCE: 22
gttcttctcg gcctgtttcc                                                 20

<210> SEQ ID NO 23
<211> LENGTH: 19
<212> TYPE: DNA
<213> ORGANISM: artificial
<220> FEATURE:
<223> OTHER INFORMATION: Synthetic PCR primer.
```

```
<400> SEQUENCE: 23
cttcgcaagc cctcatttc                                              19

<210> SEQ ID NO 24
<211> LENGTH: 19
<212> TYPE: DNA
<213> ORGANISM: artificial
<220> FEATURE:
<223> OTHER INFORMATION: Synthetic PCR primer.

<400> SEQUENCE: 24
gagaaggcga aatccgaag                                              19

<210> SEQ ID NO 25
<211> LENGTH: 20
<212> TYPE: DNA
<213> ORGANISM: artificial
<220> FEATURE:
<223> OTHER INFORMATION: Synthetic PCR primer.

<400> SEQUENCE: 25
ccccagcctt tactcttcct                                             20

<210> SEQ ID NO 26
<211> LENGTH: 20
<212> TYPE: DNA
<213> ORGANISM: artificial
<220> FEATURE:
<223> OTHER INFORMATION: Synthetic PCR primer.

<400> SEQUENCE: 26
ctggttgctc caggttgaat                                             20

<210> SEQ ID NO 27
<211> LENGTH: 22
<212> TYPE: DNA
<213> ORGANISM: artificial
<220> FEATURE:
<223> OTHER INFORMATION: Synthetic PCR primer.

<400> SEQUENCE: 27
caactccatc atgaagtgtg ac                                          22

<210> SEQ ID NO 28
<211> LENGTH: 20
<212> TYPE: DNA
<213> ORGANISM: artificial
<220> FEATURE:
<223> OTHER INFORMATION: Synthetic PCR primer.

<400> SEQUENCE: 28
gccatgccaa tctcatcttg                                             20

<210> SEQ ID NO 29
<211> LENGTH: 23
<212> TYPE: RNA
<213> ORGANISM: artificial
<220> FEATURE:
<223> OTHER INFORMATION: Synthetic shRNA

<400> SEQUENCE: 29
gccgaaccca gcaccaggag gcg                                         23

<210> SEQ ID NO 30
<211> LENGTH: 46
```

```
<212> TYPE: RNA
<213> ORGANISM: Homo sapiens

<400> SEQUENCE: 30
gccgggcgug auggugggcg ccuguagucc cagcuacucg ggaggc                      46

<210> SEQ ID NO 31
<211> LENGTH: 48
<212> TYPE: RNA
<213> ORGANISM: Artificial
<220> FEATURE:
<223> OTHER INFORMATION: Synthetic random RNA

<400> SEQUENCE: 31
cacugacacu gacacugaca cugacacuga cacugacacu gacacuga                    48
```